United States Patent
Tsutsumi et al.

(10) Patent No.: US 7,265,120 B2
(45) Date of Patent: Sep. 4, 2007

(54) PYRAZINE DERIVATIVES AND PHARMACEUTICAL USE THEREOF

(75) Inventors: Hideo Tsutsumi, Osaka (JP); Seiichiro Tabuchi, Osaka (JP); Masatoshi Minagawa, Osaka (JP); Atsushi Akahane, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 154 days.

(21) Appl. No.: 11/087,761

(22) Filed: Mar. 24, 2005

(65) Prior Publication Data

US 2005/0222159 A1 Oct. 6, 2005

(30) Foreign Application Priority Data

Apr. 1, 2004 (AU) .............................. 2004901772

(51) Int. Cl.
*C07D 403/04* (2006.01)
*C07D 403/14* (2006.01)
*A61K 31/497* (2006.01)
*A61P 25/24* (2006.01)

(52) U.S. Cl. .................. 514/252.02; 544/238
(58) Field of Classification Search ................ 544/238; 514/252.02
See application file for complete search history.

*Primary Examiner*—Kahsay Habte
(74) *Attorney, Agent, or Firm*—Oblon, Spivak, McClelland, Maier & Neustadt, P.C.

(57) ABSTRACT

A pyrazine derivative of the following formula (I):

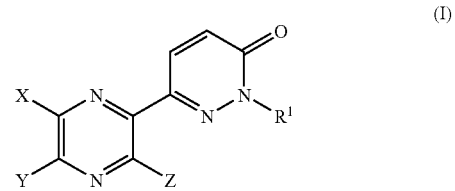

wherein
$R^1$ is hydrogen or optionally substituted lower alkyl;
X is hydrogen, halogen, hydroxy, cyano, acyl, or amino, aryl, heterocyclic group or the like;
Y is hydrogen, halogen, hydroxy, acyl, amino, or the like;
Z is aryl or heteroaryl, each of which is optionally substituted;
or a salt thereof.

The pyrazine compound (I) and a salt thereof of the present invention are adenosine antagonists and are useful for the prevention and/or treatment of depression, dementia (e.g. Alzheimer's disease, cerebrovascular dementia, dementia accompanying Parkinson's disease, etc.), Parkinson's disease, anxiety, pain, cerebrovascular disease (e.g. stroke, etc.), heart failure and the like.

15 Claims, No Drawings

PYRAZINE DERIVATIVES AND PHARMACEUTICAL USE THEREOF

TECHNICAL FIELD

The present invention relates to a novel pyrazine derivative and a salt thereof, which are useful as medicaments.

BACKGROUND ART

Adenosine is a ubiquitous biochemical messenger. Adenosine binds to and activates seven-transmembrane spanning G-protein coupled receptors, eliciting a variety of physiological responses. Adenosine receptors are divided into four known subtypes (i.e., $A_1$, $A_{2a}$, $A_{2b}$, and $A_3$). These receptor subtypes mediate different, and sometimes opposing, effects. Activation of the adenosine $A_1$ receptor, for example, elicits an increase in renal vascular resistance, while activation of the adenosine $A_{2a}$ receptor elicits a decrease in renal vascular resistance. Accordingly, adenosine antagonists are useful in the prevention and/or treatment of numerous diseases, including cardiac and circulatory disorders, degenerative disorders of the central nervous system, respiratory disorders, and many diseases for which diuretic treatment is suitable.

Some 2-aminopyridine compounds to exhibit adenosine receptor antagonism are known (WO 02/14282, WO 01/25210, etc.), and some 2-aminopyrimidine compounds are also known (WO 03/035639, U.S. 2001/0027196, etc.).

However, it is generally difficult to produce a pyrazine which is substituted by four different substituents, and for example the synthesis of a pyrazine compound of the formula A:

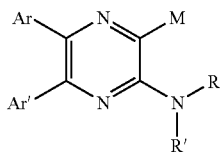

(A)

wherein Ar and Ar' are independently same or different aryl; and

R, R' and M are independently hydrogen or suitable substituent;

is reported (e.g. (1) J.Org. Chem., 40, 2341 (1975), (2) J.Heterocyclic Chem., 15, 665 (1978), (3) J.Chem.Soc.Perkin Trans.1, 1994, 885, (4) Synthesis, 1994, 931, (5) WO-02/088084, etc.), however practically, the Ar and Ar' thereof are same, and the selective synthesis of a pyrazine compound A wherein Ar and Ar' are different is not shown as far as we know, and 6-aryl-5-(6-oxo-1,6-dihydro-pyridazin-3-yl)-pyrazine compounds and derivatives thereof are novel, so there has been no knowledge about these compounds, so far. In addition, any pyrazine derivatives having both of adenosine $A_1$ and $A_{2a}$ inhibitory activities are not known.

DISCLOSURE OF INVENTION

The present invention relates to a novel pyrazine derivative and a pharmaceutically acceptable salt thereof, which are useful as medicaments; processes for preparing the preparation of pyrazine derivative and a salt thereof; a pharmaceutical composition comprising, as an active ingredient, said pyrazine derivative or a pharmaceutically acceptable salt thereof; a use of said pyrazine derivative or a pharmaceutically acceptable salt thereof as a medicament; and a method for using said pyrazine derivative or a pharmaceutically acceptable salt thereof for therapeutic purposes, which comprises administering said pyrazine derivative or a pharmaceutically acceptable salt thereof to a human being or an animal.

The pyrazine derivatives and a salt thereof are adenosine antagonists (especially, $A_1$ receptor and $A_2$ (particularly $A_{2a}$) receptor dual antagonists) and possess various pharmacological actions such as anticatalepsy action, cognitive enhancing action, analgesic action, locomotor action, antidepressant action, diuretic action, cardioprotective action, cardiotonic action, vasodilating action (e.g. cerebral vasodilating action, etc.), the action of increasing the renal blood flow, renal protective action, improvement action of renal function, enhancing action of lipolysis, inhibition action of anaphylactic bronchoconstriction, acceleration action of the insulin release, the action of increasing the production of erythropoietin, inhibiting action of platelet aggregation, or the like.

They are useful as cognitive enhancer, antianxiety drug, antidementia drug, psychostimulant, analgesic, cardioprotective agent, antidepressant, ameliorants of cerebral circulation, tranquilizer, drug for heart failure, cardiotonic agent, antihypertensive agent, drug for renal failure (renal insufficiency), drug for renal toxicity, renal protective agent, drug for improvement of renal function, diuretic, drug for edema, antiobesity, antiasthmatic, bronchodilator, drug for apnea, drug for gout, drug for hyperuricemia, drug for sudden infant death syndrome (SIDS), ameliorants of immunosuppressive action of adenosine, antidiabetic agent, drug for ulcer, drug for pancreatitis, drug for Meniere's syndrome, drug for anemia; drug for thrombosis, drug for myocardial infarction, drug for obstruction, drug for arteriosclerosis obliterans, drug for thrombophlebitis, drug for cerebral infarction, drug for transient ischemic attack, drug for angina pectoris, or the like; and useful for the prevention and/or treatment of depression, dementia (e.g. Alzheimer's disease, cerebrovascular dementia, dementia accompanying Parkinson's disease, etc.), Parkinson's disease, anxiety, pain, cerebrovascular disease (e.g. stroke, etc.), heart failure; hypertension (e.g. essential hypertension, nephrogenous hypertension, etc.); circulatory insufficiency (acute circulatory insufficiency) caused by, for example, ischemia/reperfusion injury (e.g. myocardial ischemia/reperfusion injury, cerebral ischemia/reperfusion injury, peripheral ischemia/reperfusion injury, etc.), shock (e.g. endotoxin shock, hemorrhagic shock, etc.), surgical procedure, or the like; post-resuscitation asystole; bradyarrhythmia; electromechanical dissociation; hemodynamic collapse; SIRS (systemic inflammatory response syndrome); multiple organ failure; renal failure (renal insufficiency) (e.g. acute renal failure, etc.), renal toxicity [e.g. renal toxicity induced by a drug such as cisplatins, gentamicin, FR-900506 (disclosed in EP-0184162), cyclosporine (e.g. cyclosporin A) or the like; glycerol, etc.], nephrosis, nephritis, edema (e.g. cardiac edema, nephrotic edema, hepatic edema, idiopathic edema, drug edema, acute angioneurotic edema, hereditary angioneurotic edema, carcinomatous ascites, gestational edema, etc.); obesity, bronchial asthma, gout, hyperuricemia, sudden infant death syndrome, immunosuppression, diabetes, ulcer such as peptic ulcer (e.g. gastric ulcer, duodenal ulcer, etc.), pancreatitis, Meniere's syndrome, anemia, dialysis-induced hypotension, constipation, ischemic bowel disease, ileus (e.g. mechanical ileus, adynamic ileus, etc.); and myocardial infarction, thrombosis (e.g. arterial thrombosis, cerebral thrombosis, etc.), obstruction, arteriosclerosis obliterans, thrombophlebitis, cerebral infarction, transient ischemic attack, angina pectoris, or the like.

The novel pyrazine derivative or a salt thereof of the present invention can be shown by the following formula (I):

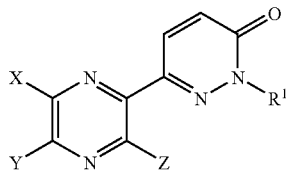

(I)

wherein $R^1$ is hydrogen or optionally substituted lower alkyl;

X is hydrogen, halogen, hydroxy, mercapto, cyano or, acyl; or lower alkyl, lower alkenyl, lower alkynyl, lower alkoxy, cyclo(lower)alkoxy, lower alkylthio, aryloxy, arylthio, amino, aryl, heterocyclic group or heterocyclyloxy, each of which is optionally substituted;

Y is hydrogen, halogen, hydroxy, mercapto, cyano or acyl; or lower alkyl, lower alkoxy, lower alkylthio, amino, aryl or heteroaryl, each of which is optionally substituted; and Z is aryl or heteroaryl, each of which is optionally substituted;

or a salt thereof.

The preferred embodiments of the pyrazine compound of the present invention are as follows.

(1) The pyrazine compound of the general formula (I) wherein $R^1$ is hydrogen or lower alkyl; and Y is hydrogen, hydroxy, lower alkoxy, cyano, acyl or optionally substituted amino;

or a salt thereof.

(2) The pyrazine compound of (1) wherein $R^1$ is lower alkyl;

Y is hydrogen, amino or dimethylsulfanylideneamino; and

Z is phenyl, pyridyl or thienyl, each of which is optionally substituted;

or a salt thereof.

(3) The pyrazine compound of (2) wherein

X is hydrogen, halogen, hydroxy, cyano, carboxy, lower alkyl carbonyl, lower alkoxy carbonyl, lower alkyl sulfinyl, lower alkyl sulfonyl;

or a salt thereof.

(4) The pyrazine compound of (2) wherein

X is lower alkyl, lower alkenyl, lower alkynyl, lower alkoxy, cyclo(lower)alkoxy, lower alkylthio, carbamoyl, thiocarbamoyl, aryloxy, arylthio, amino, aryl, heterocyclic group or heterocyclyloxy, each of which is optionally substituted;

or a salt thereof.

(5) The pyrazine compound of (2) wherein

Y is hydrogen or amino; and

Z is phenyl or thienyl which is optionally substituted;

or a salt thereof.

(6) The pyrazine compound of (5) wherein

X is hydrogen, chloro, bromo, hydroxy, cyano, methylcarbonyl, methylthio, carbamoyl, furyl, thienyl, pyrrolyl, pyrazolyl, triazolyl, phenoxy, fluorophenoxy, pyrrolidinyloxy, benzylpyrrolidinyloxy, thiazolyl, methylthiazolyl or phenylthiazolyl;

or a salt thereof.

(7) The pyrazine compound of (5) wherein

X is amino, vinyl, ethynyl or lower alkoxy, each of which is optionally substituted;

or a salt thereof.

(8) The pyrazine compound of (1) wherein $R^1$ is methyl, ethyl or isopropyl;

X is hydrogen, chloro, bromo, hydroxy, cyano, methylcarbonyl, carbamoyl, pyrazolyl, triazolyl, methylthiazolyl, pyridylmethylamino, methoxyethylamino, furylmethylamino, cyclohexylethynyl, trifluoromethylmethoxy or butoxy;

Y is amino; and

Z is phenyl or fluorophenyl;

or a salt thereof.

The object compound (I) and a salt thereof of the present invention can be prepared by the following processes.

Process 1

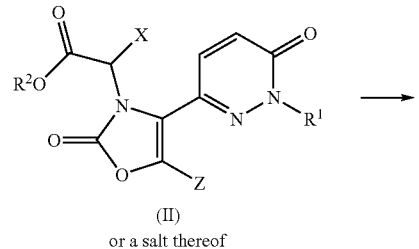

(II)
or a salt thereof

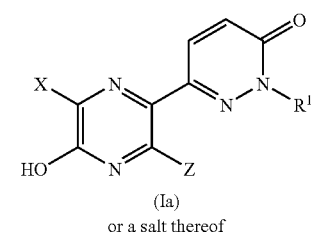

(Ia)
or a salt thereof

Process 2

(III) or a salt thereof → (Ib) or a salt thereof

Process 3

(Ia) or a salt thereof → (Ic) or a salt thereof

Process 4

(Id) or a salt thereof + (IV) or a salt thereof → (Ie) or a salt thereof

Process 5

(V) or a salt thereof → (If) or a salt thereof

Process 6

(Ig) or a salt thereof → (Ic) or a salt thereof

Process 7

(Ig) or a salt thereof + (VI) or a salt thereof → (Ih) or a salt thereof

Process 8

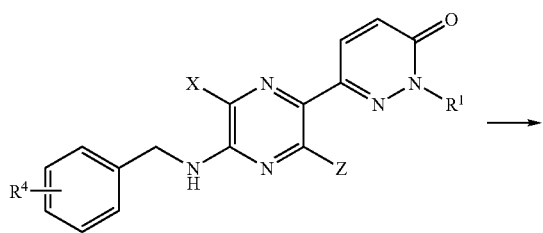

(Ih)
or a salt thereof

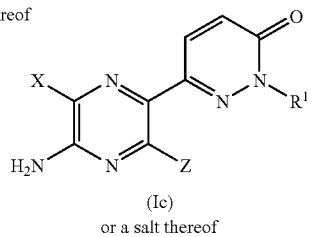

(Ic)
or a salt thereof

Process 9

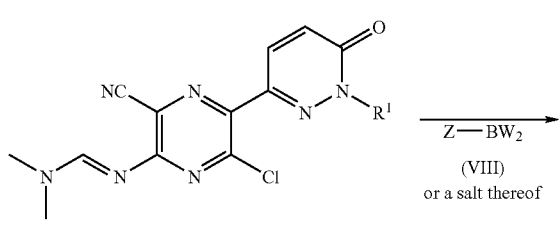

(VII)
or a salt thereof

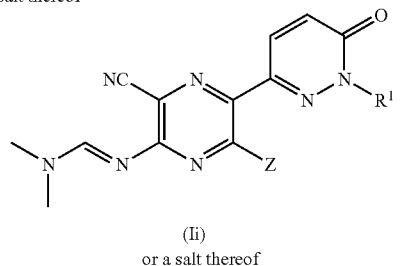

(Ii)
or a salt thereof

Process 10

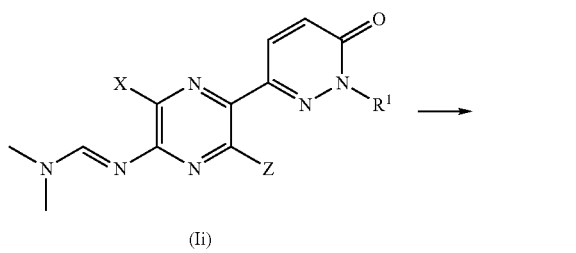

(Ii)
or a salt thereof

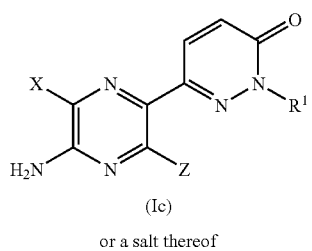

(Ic)
or a salt thereof

Process 11

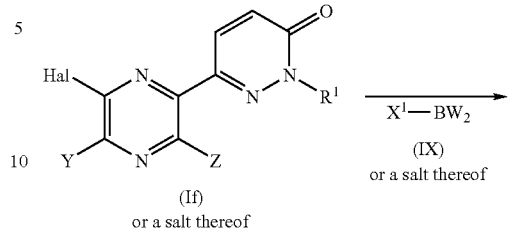

(If)
or a salt thereof

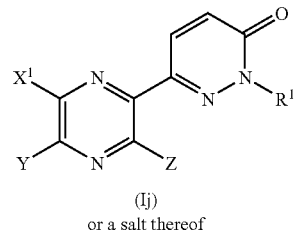

(Ij)
or a salt thereof

Process 12

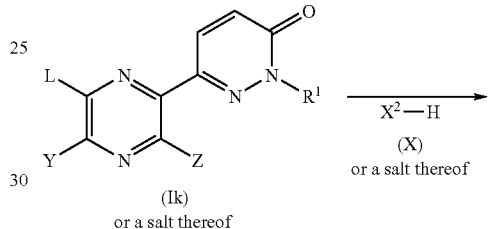

(Ik)
or a salt thereof

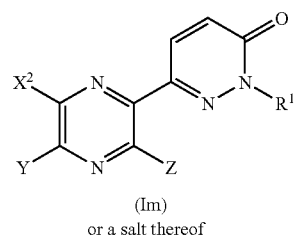

(Im)
or a salt thereof

[wherein $R^1$, X, Y and Z are defined above, $R^2$ is hydrogen or lower alkyl;

$R^3$ is lower alkyl;

$R^4$ is lower alkoxy;

$X^1$ is aryl or heteroaryl, each of which is optionally substituted;

$X^2$ is lower alkenyl, lower alkynyl, lower alkoxy, cyclo(lower)alkoxy, lower alkylthio, aryloxy, arylthio, $NR^5R^6$ (wherein $R^5$ and $R^6$ are each hydrogen, lower alkyl, cyclo(lower)alkyl, aryl, heterocyclic group, or $R^5$, $R^6$ and nitrogen atom to which they are attached form a N-containing heterocyclic group) or heterocyclyloxy, each of which is optionally substituted, or hydroxy;

Hal is a halogen atom;

L is a leaving group; and $BW_2$ is a constituent of boronic acid such as $B(OH)_2$, tetramethyl-1,3,2-dioxaborolan-2-yl, $B(CHCH_3CH(CH_3)_2)_2$, or 9-borabicyclo[3.3.1]nonanyl.]

The starting compounds or a salt thereof is novel and can be prepared, for example, by the following reaction schemes.

Process A
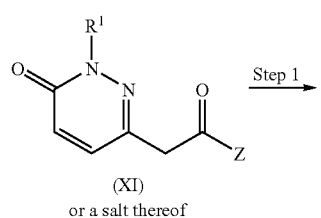
(XI)
or a salt thereof
Step 1
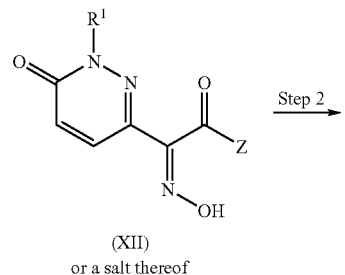
(XII)
or a salt thereof
Step 2
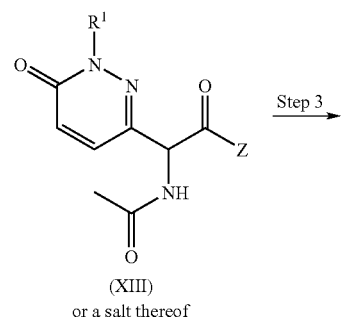
(XIII)
or a salt thereof
Step 3
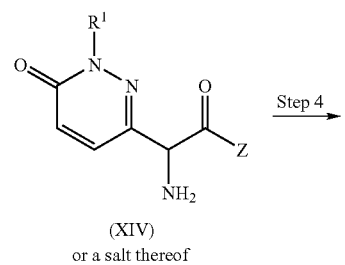
(XIV)
or a salt thereof
Step 4
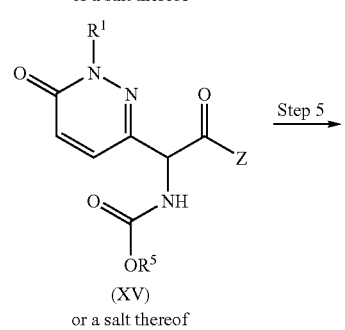
(XV)
or a salt thereof
Step 5
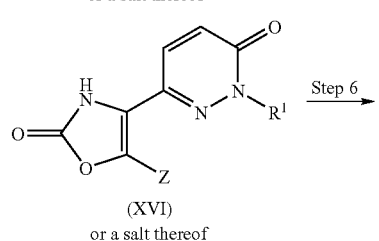
(XVI)
or a salt thereof
Step 6
-continued
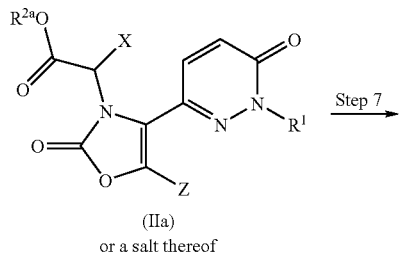
(IIa)
or a salt thereof
Step 7
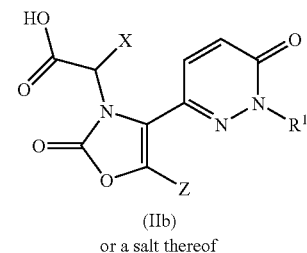
(IIb)
or a salt thereof
Process B
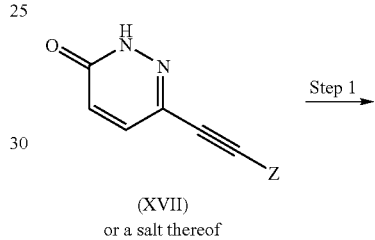
(XVII)
or a salt thereof
Step 1
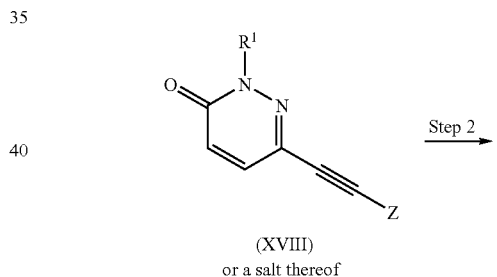
(XVIII)
or a salt thereof
Step 2
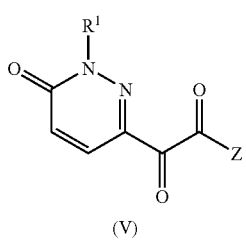
(V)
or a salt thereof
Process C
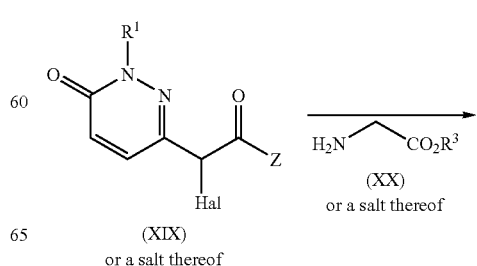
(XIX)
or a salt thereof -continued

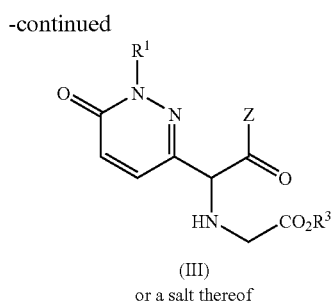

(III)
or a salt thereof

Process D

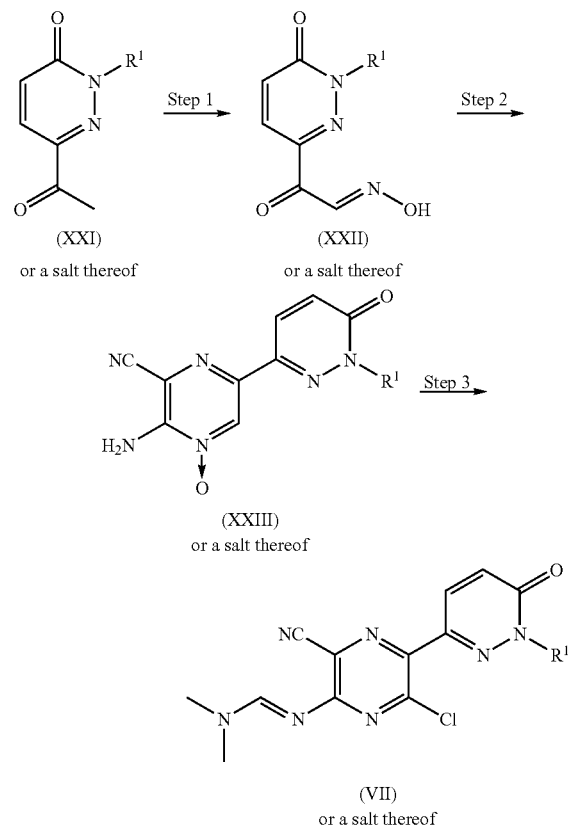

[wherein $R^1$, $R^3$, Z and Hal are defined above; and $R^{2a}$ and $R^5$ are each lower alkyl.]

In addition to the processes as mentioned above, the object compound (I) and a salt thereof can be prepared, for example, according to the procedures as illustrated in Examples in the present specification or in a manner similar thereto.

The starting compounds can be prepared, for example, according to the procedures as illustrated in Preparations in the present specification or in a manner similar thereto.

The object compound (I) and a salt thereof can be prepared according to the methods as shown in Preparations or Examples, or in a manner similar thereto.

It is also to be noted that the solvating form of the compound (I) (e.g. hydrate, etc.) and any form of the crystal of the compound (I) are included within the scope of the present invention.

It is also to be noted that radiolabelled derivatives of compound (I), which are suitable for biological studies, are included within the scope of the present invention.

Suitable salts of the object compound (I) are conventional pharmaceutically acceptable ones and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, fumarate, methanesulfonate, benzenesulfonate, formate, toluenesulfonate, etc.), an inorganic acid salt (e.g. hydrochloride, hydrobromide, hydriodide, sulfate, phosphate, etc.), a salt with an amino acid (e.g. arginine, aspartic acid, glutamic acid, etc.), and the like.

Suitable examples and illustrations of the various definitions which the present invention includes within the scope thereof and which appear in the above and following description in the present specification are explained in detail as follows.

The term "lower" is intended to mean 1 to 6 carbon atom(s) unless otherwise indicated.

Suitable "lower alkyl" and "lower alkyl" moiety in the term of "lower alkylthio" and "mono- or di-(lower) alkylamino" may include straight or branched ones such as methyl, ethyl, propyl, isopropyl, butyl, tert-butyl, pentyl, hexyl or the like, in which the preferred one may be methyl, ethyl or isopropyl.

Suitable "optionally substituted lower alkyl" may include lower alkyl which is optionally substituted by suitable substituent(s) such as halogen, lower alkenyl, lower alkoxy, hydroxy, cyclo(lower)alkyl, optionally substituted amino, acylamino, aryl, heterocyclic group, acyl or the like, in which the preferred one may be hydroxymethyl, hydroxyethyl, aminoethyl, benzyl or pyridylmethyl.

Suitable "lower alkenyl" may include straight or branched ones such as vinyl, propenyl, allyl, isopropenyl, butenyl, pentenyl, hexenyl or the like, in which the preferred one may be vinyl.

Suitable "optionally substituted lower alkenyl" may include lower alkenyl which is optionally substituted by suitable substituent(s) such as lower alkoxy, hydroxy, cyclo(lower)alkyl, amino, aryl, heterocyclic group, acyl or the like.

Suitable "lower alkynyl" may include straight or branched ones such as ethynyl, propynyl, butynyl, pentynyl, hexynyl or the like, in which the preferred one may be ethynyl.

Suitable "optionally substituted lower alkynyl" may include lower alkynyl which is optionally substituted by suitable substituent(s) such as lower alkoxy, hydroxy, cyclo(lower)alkyl, amino, aryl, heterocyclic group, acyl or the like.

Suitable "lower alkoxy" may include straight or branched ones such as methoxy, ethoxy, propoxy, isopropoxy, butoxy, tert-butoxy, pentyloxy, hexyloxy or the like, in which the preferred one may be $(C_1-C_4)$alkoxy and the more preferred one may be methoxy or ethoxy.

Suitable "optionally substituted lower alkoxy" may include lower alkoxy which is optionally substituted by suitable substituent(s) such as hydroxy, halogen, cyclo(lower)alkyl, lower alkoxy, optionally substituted amino, optionally substituted aryl, heterocyclic group, acyl or the like.

Suitable "cyclo(lower)alkyl" may be cyclo$(C_3-C_8)$alkyl such as cyclopropyl, cyclobutyl, cyclopentyl, cyclohexyl, cycloheptyl, cyclooctyl or the like, in which the preferred one may be cyclohexyl.

Suitable "aryl" and "aryl" moiety in the terms of "aryloxy" and "arylthio" may include phenyl, naphthyl, indenyl, anthryl, or the like, in which the preferred one may be ($C_6$-$C_{10}$) aryl, and the more preferred one may be phenyl.

Suitable "optionally substituted aryl" may include aryl which is optionally substituted by suitable substituent(s), preferably 1 to 3 substituent(s), such as lower alkyl, lower alkoxy, hydroxy, halogen, etc. Suitable examples of optionally substituted aryl include lower alkylphenyl, lower alkoxyphenyl and halophenyl, in which more preferred one is methoxyphenyl or fluorophenyl.

Suitable "heterocyclic group" may be saturated or unsaturated monocyclic or polycyclic heterocyclic groups containing at least one heteroatom selected from among oxygen, sulfur and nitrogen.

The particularly preferred example of said heterocyclic group may include 3- through 8-membered unsaturated heteromonocyclic groups containing 1 through 4 nitrogen atom(s), such as pyrrolyl, pyrrolinyl, imidazolyl, pyrazolyl, pyridyl and its N-oxide, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), dihydrotriazinyl (e.g. 4,5-dihydro-1,2,4-triazinyl, 2,5-dihydro-1,2,4-triazinyl, etc.), etc.;

3- through 8-membered saturated heteromonocyclic groups containing 1 through 4 nitrogen atom(s), such as azetidinyl, pyrrolidinyl, imidazolidinyl, piperidyl (e.g. piperidino, etc.), piperazinyl, etc.;

unsaturated condensed heterocyclic groups containing 1 through 5 nitrogen atom(s), such as indolyl, isoindolyl, indolizinyl, indolinyl, isoindolinyl, benzimidazolyl, quinolyl, isoquinolyl, indazolyl, benzotriazolyl, tetrazolopyridyl, tetrazolopyridazinyl (e.g. tetrazolo[1,5-b]pyridazinyl etc.), dihydrotriazolopyridazinyl, etc.;

saturated condensed heterocyclic groups containing 1 through 5 nitrogen atom(s), such as hexahydropyrrolopyrazinyl, etc.;

3- through 8-membered unsaturated heteromonocyclic groups containing 1 or 2 oxygen atoms and 1 through 3 nitrogen atom(s), such as oxazolyl, isoxazolyl, oxadiazolyl (e.g. 1,2,4-oxadiazolyl, 1,3,4-oxadiazolyl, 1,2,5-oxadiazolyl, etc.), etc.;

3- through 8-membered saturated heteromonocyclic groups containing 1 or 2 oxygen atom(s) and 1 through 3 nitrogen atoms, such as morpholinyl, oxazolidinyl (e.g. 1,3-oxazolidinyl etc.), etc.;

unsaturated condensed heterocyclic groups containing 1 or 2 oxygen atom(s) and 1 through 3 nitrogen atom(s), such as benzoxazolyl, benzoxadiazolyl, etc.;

saturated condensed heterocyclic groups containing 1 or 2 oxygen atom(s) and 1 through 3 nitrogen atom(s), such as 8-oxa-3-azabicyclo[3.2.1]octyl, etc.;

3- through 8-membered unsaturated heteromonocyclic groups containing 1 or 2 sulfur atom(s) and 1 through 3 nitrogen atom(s), such as thiazolyl, isothiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl), etc.;

3- through 8-membered saturated heteromonocyclic groups containing 1 or 2 sulfur atom(s) and 1 through 3 nitrogen atom(s), such as thiazolidinyl etc.;

3- through 8-membered unsaturated heteromonocyclic groups containing 1 sulfur atom, such as thienyl etc.;

unsaturated condensed heterocyclic groups containing 1 or 2 sulfur atoms and 1 through 3 nitrogen atom(s), such as benzothiazolyl, benzothiadiazolyl, etc.;

3- through 8-membered unsaturated heteromonocyclic groups containing 1 or 2 oxygen atom(s), such as furyl, pyranyl, dioxolyl, etc.;

3- through 8-membered saturated heteromonocyclic groups containing 1 or 2 oxygen atom(s), such as oxolanyl, tetrahydropyranyl (e.g. tetrahydro-2H-pyran-2-yl etc.), dioxolanyl, etc.; and unsaturated condensed heterocyclic groups containing 1 or 2 oxygen atom(s), such as isobenzofuranyl, chromenyl (e.g. 2H-chromen-3-yl etc.), dihydrochromenyl (e.g. 3,4-dihydro-2H-chromen-4-yl etc.), etc.

Suitable "optionally substituted heterocyclic group" may include heterocyclic group which is optionally substituted by suitable substituent(s), preferably 1 to 3 substituent (s), such as lower alkyl, lower alkoxy, hydroxy, oxo, halogen, benzyl, optionally substituted amino, aryl, or the like.

Suitable "heteroaryl" and "heteroaryl" moiety in the term of "heteroaryl(lower)alkyl" may be aforesaid "heterocyclic group", in which those categorized as an aromatic heterocyclic group, such as pyrrolyl, pyrrolinyl, imidazolyl, pyrazolyl, pyridyl, pyrimidinyl, pyrazinyl, pyridazinyl, triazolyl, tetrazolyl, dihydrotriazinyl, indolyl, isoindolyl, indolizinyl, benzimidazolyl, quinolyl, isoquinolyl, indazolyl, benzotriazolyl, tetrazolopyridyl, tetrazolopyridazinyl, dihydrotriazolopyridazinyl, oxazolyl, isoxazolyl, oxadiazolyl, benzoxazolyl, benzoxadiazolyl, thiazolyl, isothiazolyl, thiazolinyl, thiadiazolyl, thienyl, benzothiazolyl, benzothiadiazolyl, furyl, pyranyl, dioxolyl, isobenzofuranyl, chromenyl, dihydrochromenyl, etc.

Suitable "acyl" may include lower alkanoyl, aroyl, carboxy, protected carboxy, and the like.

Suitable examples of aforesaid "lower alkanoyl" may be formyl, acetyl, propionyl, butyryl, isobutyryl, pivaloyl, hexanoyl, lower(alkyl)sulfinyl (e.g., ethylsulfinyl, etc.), or the like, in which the preferred one may be ($C_1$-$C_4$)alkanoyl.

Suitable examples of aforesaid "aroyl" may be benzoyl, toluoyl, or the like.

Suitable examples of aforesaid "protected carboxy" may be
  i) esterified carboxy, in which suitable esterified carboxy may include lower alkoxycarbonyl (e.g. methoxycarbonyl, ethoxycarbonyl, propoxycarbonyl, butoxycarbonyl, t-butoxycarbonyl, pentyloxycarbonyl, hexyloxycarbonyl, etc.), aryl(lower)alkoxycarbonyl (e.g. benzyloxycarbonyl, phenethyloxycarbonyl, 2-phenylpropoxycarbonyl, 4-phenylbutoxycarbonyl, 4-phenylpentyloxycarbonyl, 1,3-diphenylhexyloxycarbonyl, etc.), lower(alkyl)sulfonyl(e.g. methylsulfonyl, etc.), and the like;
  ii) amidated carboxy, in which suitable amidated carboxy may include carbamoyl, N-(lower)alkylcarbamoyl (e.g. N-methylcarbamoyl, N-ethylcarbamoyl, N-isopropylcarbamoyl, N-butylcarbamoyl, N-pentylcarbamoyl, N-hexylcarbamoyl, etc.), N,N-di(lower)alkylcarbamoyl [e.g. N,N-dimethylcarbamoyl, N,N-diethylcarbamoyl, N-methyl-N-ethylcarbamoyl, N,N-dipropylcarbamoyl, N,N-di(t-butyl)carbamoyl, N-pentyl-N-hexylcarbamoyl, etc.], N-lower alkyl-N-ar(lower) alkylcarbamoyl (e.g. N-methyl-N-benzylcarbamoyl, etc), thiocarbamoyl, and the like.

Suitable "halogen" may be fluoro, chloro, bromo and iodo.

Suitable "a leaving group" may include halogen, hydroxy, acyloxy such as alkanoyloxy (e.g. acetoxy, propionyloxy, etc.) or sulfonyloxy (e.g. mesyloxy, tosyloxy, etc.), or the like.

Suitable "optionally substituted amino" may include amino, mono- or di-(lower)alkylamino (e.g. methylamino, dimethylamino, methylethylamino, etc.), optionally substituted lower alkyl amino (e.g. methoxyethylamino, dimethylaminoethylamino, benzylamino, morphorinoethylamino, pyridylmethylamino, furylmethylamino, etc.) acylamino (e.g. formylamino, lower alkoxycarbonylamino (e.g. methoxycarbonylamino, ethoxycarbonylamino, etc.), sulfonylamino (e.g. mesylamino, etc.), ureido, etc.), methyleneamino, (dimethylamino)methyleneamino, dimethylsulfanylideneamino, or the like.

The processes for preparing the object pyrazine compound (I) are explained in detail in the following.

Process 1

The compound (Ia) or a salt thereof can be prepared by subjecting the compound (II) or a salt thereof to re-ring-conformation with ammonium acetate following the ring-opening reaction with an acid.

This reaction is usually carried out in a conventional solvent such as water, acetone, dioxane, acetonitrile, 1,2-dimethoxyethane, chloroform, methylene chloride, ethylene chloride, tetrahydrofuran, N,N-dimethylformamide, methanol, ethanol, dimethyl sulfoxide, diethyl ether, ethyl acetate, a mixture thereof or any other organic solvent which does not adversely affect the reaction.

The reaction temperature is not critical, and the reaction is usually carried out at ambient temperature, under warming or heating.

Process 2

The compound (Ib) or a salt thereof can be prepared by subjecting the compound (III) or a salt thereof to ring-conformation with ammonium acetate.

The reaction may be carried out in a conventional solvent such as water, alcohol (e.g. methanol, ethanol, etc.), acetone, dioxane, acetonitrile, chloroform, methylene chloride, ethylene dichloride, tetrahydrofuran, ethyl acetate, N,N-dimethylformamide, pyridine or any other organic solvent which does not adversely affect the reaction. These conventional solvents may also be used in a mixture with water.

The reaction temperature is not critical, and the reaction is usually carried out at ambient temperature, under warming or under heating.

Process 3

The compound (Ic) or a salt thereof can be prepared by one pot reaction consisting of in situ rearrangement-amination following the alkylation of hydroxyl-oxygen atom of the compound (Ia) or a salt thereof with iodoacetamide.

The present reaction may be carried out in a solvent such as water, phosphate buffer, acetone, chloroform, acetonitrile, nitrobenzene, methylene chloride, ethylene dichloride, formamide, N,N-dimethylformamide, methanol, ethanol, sec-butanol, amyl alcohol, diethyl ether, dioxane, tetrahydrofuran, dimethyl sulfoxide, or any other organic solvent, which does not adversely affect the reaction, preferably in ones having strong polarities. Among the solvents, hydrophilic solvents may used in a mixture with water. The reaction is preferably conducted in the presence of base, for example, inorganic base such as alkali metal hydroxide, alkalimetal carbonate, alkalimetal bicarbonate, alkali metal hydride (e.g. sodium hydride, etc.), organic base such as trialkylamine, and the like.

The reaction temperature is not critical, and the reaction is usually carried out at ambient temperature, under warming or under heating.

The present reaction is preferably carried out in the presence of alkali metal halide (e.g. sodium iodide, potassium iodide, etc.), alkali metal thiocyanate (e.g. sodium thiocyanate, potassium thiocyanate, etc.), di(lower)alkyl azodicarboxylate (e.g. diethyl azodicarboxylate, diisopropyl azodicarboxylate, etc.) or the like.

This reaction can be carried out by the method disclosed in Example 3 and 31, etc. mentioned later or the similar manners thereto.

Process 4

The compound (Ie) or a salt thereof can be prepared by reacting the compound (Id) or a salt thereof with the compound (IV) or a salt thereof.

This reaction can be carried out by the method disclosed in Example 32, etc. mentioned later or the similar manners thereto.

Process 5

The compound (If) or a salt thereof can be prepared by subjecting the compound (V) or a salt thereof to pyrazine ring-formation with 2,3-diamino-2-butenedinitrile.

The reactions may be carried out in a conventional solvent such as water, alcohol (e.g. methanol, ethanol, etc.), acetone, dioxane, acetonitrile, chloroform, methylene chloride, ethylene dichloride, tetrahydrofuran, ethyl acetate, toluene, N,N-dimethylformamide, dimethyl sulfoxide, pyridine or any other organic solvent which does not adversely affect the reaction. These conventional solvents may also be used in a mixture with water.

The reaction is preferably conducted in the presence of a base or an acid.

Suitable base includes an inorganic base and organic base such as an alkali metal (e.g. sodium, potassium, etc.), an alkaline earth metal (e.g. magnesium, calcium, etc.), the hydroxide or carbonate or bicarbonate or hydride or alkoxide thereof, trialkylamine (e.g. trimethylamine, triethylamine, etc.), hydrazine, picoline, or the like.

Suitable acid includes an inorganic acid and organic acid such as hydrochloric acid, hydrobromic acid, sulfuric acid, hydrogen chloride, hydrogen bromide, formic acid, acetic acid, propionic acid, trichloroacetic acid, trifluoroacetic acid, or the like.

The reaction temperature is not critical, and the reaction is usually carried out at ambient temperature, under warming or under heating.

This reaction can be carried out by the method disclosed in Example 4, etc. mentioned later or the similar manners thereto.

Process 6

The compound (Ic) or a salt thereof can be prepared by subjecting the compound (Ig) to substitution with aqueous ammonia.

The reactions may be carried out in a conventional solvent such as water, alcohol (e.g. methanol, ethanol, etc.), acetone, N,N-dimethylformamide, tetrahydrofuran, acetonitrile, dioxane, or any other solvent which is easy to mix with water and does not adversely affect the reaction.

The reaction temperature is not critical, and the reaction is usually carried out at ambient temperature, under warming or under heating.

This reaction can be carried out by the method disclosed in Example 21 mentioned later or the similar manners thereto.

Process 7

The compound (Ih) or a salt thereof can be prepared by subjecting the compound (Ig) or a salt thereof to nucleophilic substitution with an amine such as the compound (VI) or a salt thereof.

The reactions may be carried out in a conventional solvent such as water, alcohol (e.g. methanol, ethanol, etc.), acetamide, dimethyl acetamide, N,N-dimethylformamide, tetrahydrofuran, acetonitrile, dioxane, or any other solvent which does not adversely affect the reaction.

A liquid amine can be also used as the solvent.

The reaction temperature is not critical, and the reaction is usually carried out at ambient temperature, under warming or under heating.

This reaction can be carried out by the method disclosed in Example 5 mentioned later or the similar manners thereto.

Process 8

The compound (Ic) or a salt thereof can be prepared by subjecting the compound (Ih) or a salt thereof to deprotection of amino using 2,3-dichloro-5,6-dicyano-1,4-benzoquinone.

The reaction is usually carried out in a solvent such as water, an alcohol (e.g. methanol, ethanol, isopropyl alcohol, etc.), tetrahydrofuran, dioxane, toluene, methylene chloride, ethylene dichloride, chloroform, N,N-dimethylformamide, N,N-dimethylacetamide, or any other organic solvent which does not adversely affect the reaction, or a mixture thereof.

The reaction temperature is not critical and the reaction is usually carried out under cooling to heating.

This reaction can be carried out by the method disclosed in Example 6 mentioned later or the similar manners thereto.

Process 9

The compound (Ii) or a salt thereof can be prepared by subjecting the compound (VII) or a salt thereof coupling reaction with the organoboron compound (VIII) or a salt thereof. The present reaction is preferably carried out by the method disclosed in Example 200 and 201 mentioned later or the similar manner thereto.

Process 10

The compound (Ic) or a salt thereof can be prepared from the compound (Ii) by hydrolysis.

The hydrolysis is preferably carried out in the presence of a base or an acid including Lewis acid.

Suitable base includes an inorganic base and organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), hydrazine, picoline, 1,5-diazabicyclo[4.3.0]non-5-ene, 4,4-diazabicyclo[2.2.2]octane, 1,8-diazabicyclo[5.4.0]undec-7-ene, or the like.

Suitable acid includes an organic acid (e.g. formic acid, acetic acid, propionic acid, trichloroacetic acid, trifluoroacetic acid, etc.), an inorganic acid (e.g. hydrochloric acid, hydrobromic acid, sulfuric acid, hydrogen chloride, hydrogen bromide, etc.) and Lewis acid (e.g. boron tribromide, boron trichloride, boron trifluoride, aluminum chloride, titanium trichloride, etc.).

The reaction is usually carried out in a solvent such as water, an alcohol (e.g. methanol, ethanol, isopropyl alcohol, etc.), tetrahydrofuran, dioxane, toluene, methylene chloride, ethylene dichloride, chloroform, N,N-dimethylformamide, N,N-dimethylacetamide, or any other organic solvent which does not adversely affect the reaction, or a mixture thereof.

A liquid base or acid can be also used as the solvent.

The reaction temperature is not critical and the reaction is usually carried out under cooling to heating.

This reaction can be carried out by the method disclosed in Example 41 mentioned later or the similar manners thereto.

Process 11

The compound (Ij) or a salt thereof can be prepared by subjecting the compound (If) or a salt thereof coupling reaction with the organoboron compound (IX) or a salt thereof. The present reaction is preferably carried out by the method disclosed in Example 78 mentioned later or the similar manner thereto.

Process 12

The compound (Im) or a salt thereof can be prepared by subjecting the compound (Ik) or a salt thereof coupling reaction with the compound (X) or a salt thereof. The present reaction is preferably carried out by the method disclosed in Examination 69 mentioned later or the similar manner thereto.

Process A

The compound (XII) or a salt thereof can be prepared by subjecting the compound (XI) to the oxime-formation reaction (exemplified by Step 1) by the methods disclosed in Preparation 1 and 2 mentioned later or the similar manners thereto.

Then the compound (XV) can be synthesized by functional trans-formation reaction of the oxime, which is the method disclosed in Preparation 3, 4, 5 and 6 mentioned later or the similar manners thereto that is obvious to the person skilled in the organic chemistry, from the compound (XII).

And then the ring-formation reaction exemplified by Step 5 of this process can be carried out by the method disclosed in Preparation 7 mentioned later or the similar manners thereto.

The object compound (IIa) or a salt thereof can be prepared by subjecting the compound (XVI) or a salt thereof to the alkylation (exemplified by Step 6). This reaction is carried out in the method disclosed in Preparation 8 and 9 mentioned later or the similar manners thereto.

And the another object compound (IIb) can be prepared by subjecting the compound (IIa) to the hydrolysis (exemplified by Step 7) that is disclosed in Preparation 10 mentioned later or the similar manners thereto.

Process B

The compound (XVIII) or a salt thereof can be prepared by subjecting the compound (XVII) or a salt thereof to the alkylation (exemplified by Step 1). This reaction is carried out in the method disclosed in Preparation 12 and 14 mentioned later or the similar manners thereto.

And the object compound (V) or a salt thereof can be prepared by subjecting the compound (XVIII) to oxidation (exemplified by Step 2), which is disclosed in Preparation 11, for example, mentioned later or the similar manners thereto.

Process C

The compound (III) or a salt thereof can be prepared by reacting the compound (XIX) or a salt thereof with the compound (XX) or a salt thereof. This reaction can be carried out by the method disclosed in Preparation 17 mentioned later or the similar manners thereto.

Process D

The compound (XXII) can be prepared by subjecting the compound (XXI) to the oxime-formation reaction (exemplified by Step 1) that disclosed in Preparation 20 mentioned later or the similar manners thereto.

And the compound (XXIII) or a salt thereof can be prepared by reacting the compound (XXII) or a salt thereof with aminomalonitrile. The present reaction is preferably carried out by the method disclosed in Preparation 21 mentioned later or the similar manner thereto.

The object compound (VII) or a salt thereof can be carried out by reacting the compound (XXIII) or a salt thereof with phosphorus oxychloride. This reaction can be carried out by the method disclosed in Preparation 22 mentioned later or the similar manner thereto.

Above processes, all starting materials and product compounds may be salts. The compounds of above processes can be converted to salts according to a conventional method.

The object compound (I) of the present invention is an adenosine antagonist and possesses the various pharmacological actions as stated before.

In order to show the usefulness of the compound (I) of the present invention, the pharmacological test result of the representative compound of the present invention is shown in the following.

[Test Compounds]

3-amino-6-(1-methyl-6-oxo-1,6-dihydro-3-pyridazinyl)-5-phenyl-2-pyrazinecarbonitrile (Example 17)

6-[5-amino-3-(4-fluorophenyl)-2-pyrazinyl]-2-isopropyl-3(2H)-pyridazinone (Example 36)

6-[5-amino-6-chloro-3-(4-fluorophenyl)-2-pyrazinyl]-2-isopropyl-3(2H)-pyridazinone (Example 37)

6-{6-bromo-5-[(dimethyl-lambda~4~-sulfanylidene)amino]-3-phenyl-2-pyrazinyl}-2-isopropyl-3(2H)-pyridazinone (Example 66)

6-[5-amino-3-phenyl-6-(phenylethynyl)-2-pyrazinyl]-2-isopropyl-3(2H)-pyridazinone (Example 70)

6-{5-amino-6-[(1-methyl-1H-imidazol-5-yl)ethynyl]-3-phenyl-2-pyrazinyl}-2-isopropyl-3(2H)-pyridazinone (Example 75)

6-{5-amino-6-[(2-furylmethyl)amino]-3-phenyl-2-pyrazinyl}-2-isopropyl-3(2H)-pyridazinone (Example 134)

6-[5-amino-3-phenyl-6-(1H-pyrazol-1-yl)-2-pyrazinyl]-2-methyl-3(2H)-pyridazinone (Example 153)

6-[5-amino-3-phenyl-6-(2-pyridylmethoxy)-2-pyrazinyl]-2-isopropyl-3(2H)-pyridazinone (Example 163)

6-(5-amino-6-butoxy-3-phenyl-2-pyrazinyl)-2-methyl-3(2H)-pyridazinone (Example 179)

6-[5-amino-6-(2-furylmethoxy)-3-phenyl-2-pyrazinyl]-2-methyl-3(2H)-pyridazinone (Example 184)

Test 1: Adenosine Antagonistic Activity

[I] Test Method

The adenosine antagonistic activity [Ki (nM)] of the test compound was examined by radioligand binding techniques using 8-cyclopentyl-1,3-dipropylxanthine, [dipropyl-2,3-$^3$H(N)] ([$^3$H]DPCPX, 4.5 nM) for human $A_1$ receptor and [$^3$H]CGS 21680 (20 nM) for human $A_{2a}$ receptor.

[II] Test Result

TABLE 1

| Test compound | Adenosine receptor binding (Ki:nM) | |
|---|---|---|
| (Example No.) | $A_1$ | $A_{2a}$ |
| 17 | 11.23 | 1.72 |
| 36 | 23.01 | 6.89 |
| 37 | 15.88 | 2.65 |
| 66 | 16.01 | 6.79 |
| 70 | 0.88 | 0.29 |
| 75 | 0.72 | 0.25 |
| 134 | 6.66 | 2.60 |
| 153 | 18.88 | 4.95 |
| 163 | 1.35 | 0.42 |
| 179 | 16.36 | 1.57 |
| 184 | 13.22 | 1.49 |

Test 2: Anticatalepsy Activity in Mouse

[I] Test Method

The test compound (3.2 mg/kg) was administered orally with ddY mice (n=7). Then, haloperidol (0.32 mg/kg) was injected intraperitoneally 30 min. after the administration of the compound. Thirty min. after the injection, the cataleptic responses of mice were measured. The forelimbs of each mouse were placed on a 3 cm high, 3 mm wide horizontal bar, and the duration of cataleptic posture was measured for up to 30 sec.

[II] Test Result

TABLE 2

| Test compound (Example No.) | Manifestation rate of Catalepsy (number of mouse) |
|---|---|
| 17 | 0/7 |
| 36 | 0/7 |
| 37 | 0/7 |
| 66 | 1/7 |
| 70 | 0/7 |
| 75 | 0/7 |
| 134 | 1/7 |
| 153 | 2/7 |
| 163 | 2/7 |
| 179 | 1/7 |
| 184 | 2/7 |

The pyrazine compound (I) and a salt thereof of this invention are useful as adenosine antagonists (especially, $A_1$ receptor and $A_2$ (particularly $A_{2a}$) receptor dual antagonists) and for the prevention and/or the treatment of depression, dementia (e.g. Alzheimer's disease, cerebrovascular dementia, dementia accompanying Parkinson's disease, etc.), Parkinson's disease, anxiety, pain, cerebrovascular disease, heart failure, hypertension, circulatory insufficiency, post-resuscitation, asystole, bradyarrhythmia, electro-mechanical dissociation, hemodynamic collapse, SIRS (systemic inflammatory response syndrome), multiple organ failure, renal failure (renal insufficiency), renal toxicity, nephrosis, nephritis, edema, obesity, bronchial asthma, gout, hyperuricemia, sudden infant death syndrome, immunosuppression, diabetes, ulcer, pancreatitis, Meniere's syndrome, anemia, dialysis-induced hypotension, constipation, ischemic bowel disease, ileus, myocardial infarction, thrombosis, obstruction, arteriosclerosis obliterans, thrombophlebitis, cerebral infarction, transient ischemic attack, angina pectoris, and the like.

Adenosine antagonists can be useful for Parkinson's disease by co-administrating with L-3,4-dihidroxy-phenylalanine (L-DOPA), which is the most popular drug for Parkinson's disease (R. Grondin et. al, *Neurology*, 52, 1673-1677 (1999)). So the combination use of the pyrazine compound (I) and a salt thereof of this invention with L-DOPA may be also useful for treatment and/or prevention of Parkinson's disease with decreasing or reducing the side effect such as the onset of dyskinesia eliciting by the long-team application of L-DOPA, and so on.

Further, in view of the field using these compounds for as a medicament, these compounds should be durable to some degree. And the duration time of the pyrazine compound (I) or a salt thereof of this invention are expected to be long-lasting.

The pharmaceutical composition of this invention can be used in the form of a pharmaceutical preparation, for example, in a solid, semisolid or liquid form, which contains the pyrazine compound (I) or a pharmaceutically acceptable salt thereof as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation. The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. In addition, auxiliary, stabilizing agents, thickening agents, coloring agents and perfumes may be used where necessary. The pyrazine compound (I) or a pharmaceutically acceptable salt thereof is included in a pharmaceutical composition in an amount sufficient to produce the desired aforesaid pharmaceutical effect upon the process or condition of diseases.

For applying the composition to a human being or an animal, it is preferable to apply it by intravenous, intramuscular, pulmonary or oral administration, or insufflation. While the dosage of therapeutically effective amount of the pyrazine compound (I) varies depending on the age and condition of each individual patient to be treated, in the case of intravenous administration, a daily dose of 0.01-100 mg of the pyrazine compound (I) per kg weight of a human being or an animal, in the case of intramuscular administration, a daily dose of 0.1-100 mg of the pyrazine compound (I) per kg weight of a human being or an animal, and in case of oral administration, a daily dose of 0.1-100 mg of the pyrazine compound (I) per kg weight of a human being or an animal is generally given for the prevention and/or treatment of the aforesaid diseases.

The following Preparation and Examples are given for the purpose of illustrating the present invention in more detail.

The abbreviations, symbols and terms used in the Preparations and Examples have the following meanings.

| | |
|---|---|
| AcOH | acetic acid |
| $CHCl_3$ | chloroform |
| $CDCl_3$ | chloroform-d |
| $CH_2Cl_2$ | dichloromethane |
| DMA | N,N-dimethylacetamide |
| DMF | N,N-dimethylformamide |
| DMSO | dimethyl sulfoxide |
| EtOAc | ethyl acetate |
| EtOH | ethanol |
| IPE | diisopropyl ether |
| MeOH | methanol |
| THF | tetrahydrofuran |
| HCl | hydrochloric acid |
| $MgSO_4$ | magnesium sulfate |
| $Na_2CO_3$ | sodium carbonate |
| NaH | sodium hydride |
| $NaHCO_3$ | sodium hydrogen carbonate |
| NaOH | sodium hydroxide |
| $Na_2SO_4$ | sodium sulfate |
| aq. | aqueous |
| conc. | concentrated |
| sat. | saturated |

Preparation 1

Under nitrogen atmosphere, 2-isopropyl-6-(2-oxo-2-phenylethyl)-3(2H)-pyridazinone (513 mg) was added to a suspension of NaH (60% dispersion in mineral oil) (84 mg) in THF (5 ml) and the mixture was stirred at 45-50° C. for 30 minutes. After addition of isoamyl nitrite (0.27 ml), the mixture was stirred at the same temperature for 8 hours. The mixture was dissolved in EtOAc, washed with 1N HCl and brine and dried over $MgSO_4$. The mixture was concentrated under reduced pressure and subjected to column chromatography on silica gel eluting with a mixture of n-hexane and EtOAc (50:50 v/v) to give 1-(1-isopropyl-6-oxo-1,6-dihydro-3-pyridazinyl)-2-phenyl-1,2-ethanedione 1-oxime as a solid (185 mg).

m.p.: 173-175° C. (IPE)

IR (KBr): 3153, 3024, 2854, 1691, 1647, 1576 $cm^{-1}$

Mass (ESI): 593 $(2M+Na)^+$, 308 $(M+Na)^+$ $^1$H NMR ($CDCl_3$, δ): 1.01 (6H, d, J=6.60 Hz), 5.13 (1H, 7-plet, J=6.60 Hz), 7.01 (1H, d, J=9.62 Hz), 7.45-7.63 (3H, m), 7.81 (1H, d, J=9.62 Hz), 7.87-7.93 (2H, m), 9.03 (1H, s)

Preparation 2

A solution of sodium nitrite (1.725 g) of water (5.42 ml) was added in portions to a solution of 2-isopropyl-6-(2-oxo-2-phenylethyl)-3(2H)-pyridazinone (2.57 g) in a mixture of AcOH (2 ml) and EtOAc (8 ml) at 20-25° C. and the mixture was stirred at the same temperature for 8 hours. EtOAc was added to the mixture, washed with sat. aq. $NaHCO_3$ solution and brine, dried over $MgSO_4$ and concentrated under reduced pressure to give a solid. The solid was triturated with IPE and collected by filtration to give 1-(1-isopropyl-6-oxo-1,6-dihydro-3-pyridazinyl)-2-phenyl-1,2-ethanedione 1-oxime as a solid (1.71 g), which was identical to the authentic sample (the product of Preparation 1) by melting point and IR, MS and NMR spectra.

Preparation 3

Zinc dust (1.57 g) was added in portions to a suspension of 1-(1-isopropyl-6-oxo-1,6-dihydro-3-pyridazinyl)-2-phenyl-1,2-ethanedione 1-oxime (856 mg) in a mixture acetic anhydride (1.7 ml) and AcOH (10 ml) under ambient temperature and the mixture was stirred at the same temperature for 4 hours. An insoluble material was filtered off and a filtrate was concentrated under reduced pressure to give a residue. The residue was dissolved in EtOAc, washed with sat. aq. $NaHCO_3$ solution, dried over $MgSO_4$ and subjected to column chromatography on silica gel eluting with a mixture of MeOH and EtOAc (2:98 v/v) to give N-[1-(1-isopropyl-6-oxo-1,6-dihydro-3-pyridazinyl)-2-oxo-2-phenylethyl]acetamide as a solid (724 mg).

m.p.: 65-66° C. (acetone-IPE)

IR (KBr): 3494, 3303, 1657, 1583, 1514 $cm^{-1}$

Mass (ESI): 336 $(2M+Na)^+$ $^1$H NMR ($CDCl_3$, δ): 0.96 (3H, d, J=6.60 Hz), 1.16 (3H, d, J=6.60 Hz), 2.16 (3H, s), 5.11 (1H, 7-plet, J=6.60 Hz), 6.56 (1H, d, J=7.02 Hz), 6.86 (1H, d, J=9.54 Hz), 7.10 (1H, d, J=7.02 Hz), 7.39-7.59 (4H, m), 7.94-8.01 (2H, m)

Preparation 4

A solution of N-[1-(1-isopropyl-6-oxo-1,6-dihydro-3-pyridazinyl)-2-oxo-2-phenylethyl]acetamide (1.00 g) in 10% hydrogen chloride solution of MeOH (10 ml) was refluxed for 24 hours. After cooling, a precipitate was collected by filtration to give 6-(1-amino-2-oxo-2-phenylethyl)-2-isopropyl-3(2H)-pyridazinone hydrochloride as a solid (534 mg). A filtrate was concentrated under reduced pressure, triturated with IPE and collected by filtration to give the same compound as a solid (333 mg).

m.p.: 145° C. (dec.) (MeOH)

IR (KBr): 3425, 3037-2939, 1697, 1664, 1576 $cm^{-1}$

Mass (ESI): 294 $(M+Na)^+$, 272 $(M+H)^+$ $^1$H NMR (DMSO-$d_6$, δ): 0.79 (3H, d, J=6.60 Hz), 1.11 (3H, d, J=6.60 Hz), 4.94 (1H, 7-plet, J=6.60 Hz), 6.45 (1H, s), 7.04 (1H, d, J=9.64 Hz), 7.49-7.71 (3H, m), 7.80 (1H, d, J=9.64 Hz), 7.97-8.02 (2H, m), 9.11 (3H, brs)

Preparation 5

Under ice-cooling, triethylamine (2.79 ml) was added dropwise to a suspension of 6-(1-amino-2-oxo-2-phenylethyl)-2-isopropyl-3(2H)-pyridazinone hydrochloride (3.08 g) and dimethyl dicarbonate (2.01 g) in CH$_2$Cl$_2$ (30 ml) and stirred at the same temperature for 40 minutes. The mixture was washed with 1N HCl and sat. aq. NaHCO$_3$ solution, dried over MgSO$_4$ and concentrated under reduced pressure to give a residue. The residue was subjected to column chromatography on silica gel eluting with a mixture of n-hexane and EtOAc (30:70 v/v) to give methyl [1-(1-isopropyl-6-oxo-1,6-dihydro-3-pyridazinyl)-2-oxo-2-phenylethyl]carbamate as a syrup (2.96 g).

IR (Neat): 6329, 1734-1651, 1595 cm$^{-1}$
Mass (ESI): 681 (2M+Na)$^+$, 352 (M+Na)$^+$, 330 (M+H)$^+$
$^1$H NMR (CDCl$_3$, δ): 1.06 (3H, d, J=6.60 Hz), 1.19 (3H, d, J=6.60 Hz), 3.73 (3H, s), 5.14 (1H, 7-plet, J=6.60 Hz), 6.33 (2H, brs), 6.86 (1H, d, J=9.56 Hz), 7.31-7.62 (4H, m), 7.98-8.03 (2H, m)

Preparation 6

Under ice-cooling, a solution of triethylamine (16.8 ml) of CH$_2$Cl$_2$ (30 ml) was added dropwise to a suspension of 6-(1-amino-2-oxo-2-phenylethyl)-2-isopropyl-3(2H)-pyridazinone hydrochloride (15.42 g) and methyl chloroformate (4.65 ml) in CH$_2$Cl$_2$ (155 ml) and stirred at the same temperature for 30 minutes. The mixture was washed with water, 1N HCl and sat. aq. NaHCO$_3$ solution, dried over MgSO$_4$ and concentrated under reduced pressure to give a residue. The residue was subjected to column chromatography on silica gel eluting with a mixture of n-hexane and EtOAc (30:70 v/v) to give methyl [1-(1-isopropyl-6-oxo-1,6-dihydro-3-pyridazinyl)-2-oxo-2-phenylethyl]carbamate as a syrup (15.78 g), which was identical to the authentic sample (the product of Preparation 5) by IR, MS and NMR spectra.

Preparation 7

A solution of methyl [1-(1-isopropyl-6-oxo-1,6-dihydro-3-pyridazinyl)-2-oxo-2-phenylethyl]carbamate (2.46 g) in DMF (10 ml) was added to a suspension of NaH (60% dispersion in mineral oil) (314 mg) in DMF (15 ml) and the mixture was heated at 70-75° C. for 3 hours. A mixture of AcOH (0.5 ml) and water (75 ml) was added to the mixture to give a precipitate. The precipitate was collected by filtration and dried under reduced pressure to give 2-isopropyl-6-(2-oxo-5-phenyl-2,3-dihydro-oxazol-4-yl)-3(2H)-pyridazinone as a solid (1.56 g).

m.p.: 238-239.5° C. (acetone-n-hexane)
IR (KBr): 1753, 1664, 1591 cm$^{-1}$
Mass (ESI): 617 (2M+Na)$^+$, 320 (M+Na)$^+$, 298 (M+H)$^+$
$^1$H NMR (CDCl$_3$, δ): 1.43 (6H, d, J=6.60 Hz), 5.36 (1H, 7-plet, J=6.60 Hz), 6.83 (1H, d, J=9.60 Hz), 7.27 (1H, d, J=9.60 Hz), 7.45-7.59 (5H, m), 9.25 (1H, brs)

Preparation 8

Under nitrogen atmosphere, 2-isopropyl-6-(2-oxo-5-phenyl-2,3-dihydro-oxazol-4-yl)-3(2H)-pyridazinone (100 mg) was added to a suspension of NaH (60% dispersion in mineral oil) (14 mg) in DMF (0.3 ml) at 20-25° C. and the mixture was stirred at the same temperature for 30 minutes. Methyl bromoacetate (0.0035 ml) was added to the mixture and stirred at 70-75° C. for 7 hours. After an addition of water (5 ml), an aqueous solution was removed by decantation to give a residue. The residue was dissolved in CHCl$_3$, dried over MgSO$_4$, concentrated under reduced pressure and subjected to column chromatography on silica gel eluting with a mixture of n-hexane and EtOAc (40:60 v/v) to give methyl [4-(1-isopropyl-6-oxo-1,6-dihydro-3-pyridazinyl)-2-oxo-5-phenyl-oxazol-3(2H)-yl]-acetate as a solid (64 mg).

m.p.: 109.5-111° C. (acetone-n-hexane)
IR (KBr): 1765, 1670, 1593 cm$^{-1}$
Mass (ESI): 392 (M+Na)$^+$
$^1$H NMR (CDCl$_3$, δ): 1.38 (6H, d, J=6.65 Hz), 3.70 (3H, s), 4.73 (2H, s), 5.37 (1H, 7-plet, J=6.65 Hz), 6.82 (1H, d, J=9.63 Hz), 7.10 (1H, d, J=9.63 Hz), 7.37-7.47 (5H, m)

Preparation 9

Ethyl 2-[4-(1-isopropyl-6-oxo-1,6-dihydro-3-pyridazinyl)-2-oxo-5-phenyl-oxazol-3(2H)-yl]propanoate The title compound was obtained in a similar manner to that of Preparation 8.

IR (Neat): 1770, 1670, 1589 cm$^{-1}$
Mass (ESI): 420 (M+Na)$^+$
$^1$H NMR (CDCl$_3$, δ): 1.25 (3H, t, J=7.10 Hz), 1.40 (6H, d, J=6.66 Hz), 1.77 (3H, d, J=7.25 Hz), 4.19 (2H, q, J=7.10 Hz), 4.89 (1H, q, J=7.25 Hz), 5.38 (1H, 7-plet, J=6.66 Hz), 6.87 (1H, d, J=9.66 Hz), 7.11 (1H, d, J=9.66 Hz), 7.36-7.41 (5H, m)

Preparation 10

A solution of ethyl 2-[4-(1-isopropyl-6-oxo-1,6-dihydro-3-pyridazinyl)-2-oxo-5-phenyl-oxazol-3(2H)-yl]-propanoate (3.32 g) in a mixture of 1N aq. NaOH (25 ml) and THF (25 ml) was heated at 50-55° C. for 2 hours. After removal of THF, the mixture was acidified with 1N aq. HCl, extracted with EtOAc, dried over MgSO$_4$ and concentrated under reduced pressure to give a residue. The residue was recrystallized from a mixture of CHCl$_3$ and n-hexane to give 2-[4-(1-isopropyl-6-oxo-1,6-dihydro-3-pyridazinyl)-2-oxo-5-phenyl-oxazol-3(2H)-yl]propanoic acid as a solid (2.53 g).

m.p.: 173-175° C. (CHCl$_3$-n-hexane)
IR (KBr): 2989, 1765-1747, 1630, 1568 cm$^{-1}$
Mass (ESI, Neg) 368 (M−H)$^-$
$^1$H NMR (CDCl$_3$, δ): 1.42 (6H, d, J=6.61 Hz), 1.78 (3H, d, J=7.20 Hz), 4.99 (1H, q, J=7.20 Hz), 5.34 (1H, 7-plet, J=6.61 Hz), 7.01 (1H, d, J=9.58 Hz), 7.13 (1H, d, J=9.58 Hz), 7.34 (5H, s)

Preparation 11

In the presence of palladium chloride (3.72 g), a solution of 2-isopropyl-6-(phenylethynyl)-3(2H)-pyridazinone (50.13 g) in DMSO (125 ml) was heated at 140-145° C. for 3 hours. After cooling, water (500 ml) was added and the mixture was extracted with EtOAc. An organic solution was dried over MgSO$_4$, concentrated under reduced pressure and subjected to column chromatography on silica gel eluting with a mixture of n-hexane and EtOAc (20:80 v/v) to give 1-(1-isopropyl-6-oxo-1,6-dihydro-3-pyridazinyl)-2-phenyl-1,2-ethanedione as a solid (44.98 g).

m.p.: 71-73° C. (IPE-n-hexane)
IR (KBr): 1682, 1666 cm$^{-1}$
Mass (ESI): 271 (M+Na)$^+$, 293 (M+H)$^+$
$^1$H NMR (CDCl$_3$, δ): 1.13 (6H, d, J=6.58 Hz), 5.21 (1H, 7-plet, J=6.58 Hz), 7.00 (1H, d, J=9.58 Hz), 7.26-7.57 (2H, m), 7.62-7.71 (1H, m), 7.86-7.95 (3H, m)

Preparation 12

Under nitrogen atmosphere, 6-(phenylethynyl)-3(2H)-pyridazinone (15.54 g) was added to a suspension of NaH (60% in oil suspension) (3.33 g) in DMF (90 ml) and the mixture was stirred at 50-55° C. for 30 minutes. Under ice-cooling, iodoethane (6.97 ml) was added to the mixture and the mixture was stirred at 50-55° C. for 3 hours. After addition of water, the reaction mixture was extracted with EtOAc, dried over MgSO$_4$ and concentrated under reduced pressure to give a residue. The residue was subjected to column chromatography on silica gel eluting with a mixture of n-hexane and EtOAc (70:30 v/v) to give 2-ethyl-6-(phenylethynyl)-3(2H)-pyridazinone as a solid (14.06 g).

m.p.: 74-75° C. (acetone-n-hexane)
IR (KBr): 2214, 1674, 1587 cm$^{-1}$
Mass (ESI): 471 (2M+Na)$^+$, 247 (M+Na)$^+$, 225 (M+H)$^+$
$^1$H NMR (CDCl$_3$, δ): 1.41 (3H, t, J=7.21 Hz), 4.25 (2H, q, J=7.21 Hz), 6.90 (1H, d, J=9.54 Hz), 7.33 (1H, d, J=9.54 Hz), 7.36-7.43 (3H, m), 7.53-7.60 (2H, m)

Preparation 13

1-(1-Ethyl-6-oxo-1,6-dihydro-3-pyridazinyl)-2-phenyl-1,2-ethanedione

The title compound was obtained in a similar manner to that of Preparation 11.

IR (Neat): 1697-1662, 1595 cm$^{-1}$
Mass (ESI): 279 (M+Na)$^+$, 257 (M+H)$^+$
$^1$H NMR (CDCl$_3$, δ): 1.23 (3H, t, J=7.22 Hz), 4.14 (2H, q, J=7.22 Hz), 7.02 (1H, d, J=9.64 Hz), 7.48-7.57 (2H, m), 7.63-7.72 (1H, m), 7.87-7.98 (3H, m)

Preparation 14

2-Methyl-6-(phenylethynyl)-3(2H)-pyridazinone

The title compound was obtained in a similar manner to that of Preparation 12.

m.p.: 118-120° C. (acetone-n-hexane)
IR (KBr): 2214, 1668, 1583 cm$^{-1}$
Mass (ESI): 443 (2M+Na)$^+$, 233 (M+Na)$^+$, 211 (M+H)$^+$
$^1$H NMR (CDCl$_3$, δ): 3.83 (3H, s), 6.92 (1H, d, J=9.60 Hz), 7.32-7.43 (4H, m), 7.53-7.59 (2H, m)

Preparation 15

1-(1-Methyl-6-oxo-1,6-dihydro-3-pyridazinyl)-2-phenyl-1,2-ethanedione

The title compound was obtained in a similar manner to that of Preparation 11.

m.p.: 89-92° C. (acetone-n-hexane)
IR (KBr): 1685, 1676, 1664, 1599 cm$^{-1}$
Mass (ESI): 265 (M+Na)$^+$, 243 (M+H)$^+$
$^1$H NMR (CDCl$_3$, δ): 3.74 (3H, s), 7.04 (1H, d, J=9.84 Hz), 7.49-7.58 (2H, m), 7.65-7.71 (1H, m), 7.88-8.01 (3H, m)

Preparation 16

A mixture of 2-isopropyl-6-(2-oxo-2-phenylethyl)-3(2H)-pyridazinone (100 g) and sulfurylchloride (32.9 ml) in CH$_2$Cl$_2$ (200 ml) was refluxed with stirring for 5 hours. Water and EtOAc were added to the reaction mixture. The organic layer was separated, and dried over MgSO$_4$. The solvent was removed in vacuo. The residue was purified by silica gel column chromatography eluted with a mixture of n-hexane and EtOAc. The fractions were concentrated in vacuo to obtain 6-(1-chloro-2-oxo-2-phenylethyl)-2-isopropyl-3(2H)-pyridazinone (100 g) as white powder.

$^1$H NMR (CDCl$_3$, δ): 1.2-1.4 (6H, m), 5.26 (1H, 7-plet, J=6.6 Hz), 6.25 (1H, s), 6.94 (1H, d, J=9.6 Hz), 7.4-7.7 (4H, m), 8.0-8.15 (2H, m)
Mass (ESI): 291 (M+H)$^+$, 313 (M+Na)$^+$ Preparation 17

A mixture of 6-(1-chloro-2-oxo-2-phenylethyl)-2-isopropyl-3(2H)-pyridazinone (500 mg), glysine ethyl ester (264 mg) and pottasium carbonate (523 mg) in DMF (5 ml) was stirred at room temperature for 2 hours, then at 50° C. for 1.5 hours. To the mixture was added water (30 ml) and the mixture was extracted with EtOAc (20 ml×2), then the combined organic layers was washed with water (30 ml×2) and brine (20 ml), dried over MgSO$_4$, filtered and evaporated. The residue was purified by silica gel column chromatography eluted with a mixture of n-hexane and EtOAc. The fractions were concentrated in vacuo to obtain ethyl {[1-(1-isopropyl-6-oxo-1,6-dihydro-3-pyridazinyl)-2-oxo-2-phenylethyl]amino}acetate (437.7 mg) as white powder.

$^1$H NMR (CDCl$_3$, δ): 1.1-1.4 (9H, m), 3.46 (2H, s), 4.0-4.3 (2H, m), 5.22 (1H, 7-plet, J=6.6 Hz), 5.39 (1H, s), 6.83 (1H, d, J=9.5 Hz), 7.2-7.7 (4H, m), 7.9-8.1 (2H, m)
Mass (ESI): 380 (M+Na)$^+$ Preparation 18

6-[1-Chloro-2-(4-fluorophenyl)-2-oxoethyl]-2-isopropyl-3(2H)-pyridazinone

The title compound was obtained in a similar manner to that of Preparation 16.

$^1$H NMR (DMSO-d$_6$, δ): 1.2-1.4 (6H, m), 5.26 (1H, 7-plet, J=6.6 Hz), 6.18 (1H, s), 6.95 (1H, d, J=9.6 Hz), 7.1-7.3 (2H, m), 7.50 (1H, d, J=9.6 Hz), 8.0-8.2 (2H, m)
Mass (ESI): 309 (M+H)$^+$, 331 (M+Na)$^+$ Preparation 19

Ethyl {[2-(4-fluorophenyl)-1-(1-isopropyl-6-oxo-1,6-dihydro-3-pyridazinyl)-2-oxoethyl]amino}acetate The title compound was obtained in a similar manner to that of Preparation 17.

$^1$H NMR (CDCl$_3$, δ): 1.1-1.4 (9H, m), 3.45 (2H, s), 4.0-4.3 (2H, m), 5.23 (1H, 7-plet, J=6.6 Hz), 5.35 (1H, s), 6.84 (1H, d, J=9.6 Hz), 7.0-7.2 (4H, m), 7.2-7.4 (1H, m), 7.9-8.15 (2H, m)
Mass (ESI): 376 (M+H)$^+$, 398 (M+Na)$^+$ Preparation 20

A mixture of 6-acetyl-2-isopropyl-3(2H)-pyridazinone (74.0 g) and t-butylnitrite (73.3 ml) in THF (740 ml) was stirred at 0° C. Pottasium t-butoxide (55.3 g) was added to the reaction mixture. Then the reaction mixture was stirred at 25° C. for 1 hour. Water, 1N HCl and EtOAc were added to the reaction mixture. The organic layer was washed with 1N HCl, aq. NaHCO$_3$ and brine. The organic layer was separated, and dried over MgSO$_4$. The solvent was removed in vacuo. The residue was purified by silica gel column chromatography eluted with a mixture of n-hexane and EtOAc. The fractions were concentrated in vacuo to obtain (1-isopropyl-6-oxo-1,6-dihydro-3-pyridazinyl)(oxo)-acetaldehyde oxime (15.0 g) as white powder.

$^1$H NMR (DMSO-d$_6$, δ): 1.44 (6H, d, J=6.6 Hz), 5.37 (1H, 7-plet, J=6.6 Hz), 7.02 (1H, d, J=9.6 Hz), 7.93 (1H, d, J=9.6 Hz), 8.82 (1H, s), 9.7-10.5 (1H, br)
Mass (ESI): 210 (M+H)$^+$, 232 (M+Na)$^+$ Preparation 21

A mixture of (1-isopropyl-6-oxo-1,6-dihydro-3-pyridazinyl) (oxo)acetaldehyde oxime (11.16 g), aminomalononitrile (13.6 g) and p-toluenesulfonic acid (10.2 g) in 2-propanol (200 ml) was stirred at 50° C. for 3 hours. Water, aq. NaHCO$_3$ and EtOAc were added to the reaction mixture to give a pale yellow precipitate. The precipitate was collected by filtration to obtain 3-amino-6-(1-isopropyl-6-oxo-1,6-dihydro-3-pyridazinyl)-2-pyrazinecarbonitrile 4-oxide (3.84 g) as white powder.

$^1$H NMR (DMSO-d$_6$, δ): 1.36 (6H, d, J=6.6 Hz), 5.18 (1H, 7-plet, J=6.6 Hz), 7.03 (1H, d, J=9.6 Hz), 8.02 (1H, d, J=9.6 Hz), 8.33 (2H, br), 8.94 (1H, s)
Mass (ESI): 273 (M+H)$^+$, 295 (M+Na)$^+$ Preparation 22

A solution of 3-amino-6-(1-isopropyl-6-oxo-1,6-dihydro-3-pyridazinyl)-2-pyrazinecarbonitrile 4-oxide (1.54 g) in DMF (30 ml) was stirred at 0° C. Phosphorous oxychloride (1.58 ml) was dropped to the solution and the reaction mixture was stirred under same condition for 3 hours. Water was added to the reaction mixture. The reaction mixture was stirred at 20° C. for 20 hours to give a yellow precipitate. The precipitate was collected by filtration to obtain yellow powder. The residue was purified by silica gel column chromatography eluted with a mixture of n-hexane and EtOAc. The fractions were concentrated in vacuo to obtain N'-[6-chloro-3-cyano-5-(1-isopropyl-6-oxo-1,6-dihydro-3-pyridazinyl)-2-pyrazinyl]-N,N-dimethylimidoformamide (1.0 g) as white powder.

$^1$H NMR (DMSO-d$_6$, δ): 1.42 (6H, d, J=6.6 Hz), 3.26 (3H, s), 3.27 (3H, s), 5.40 (1H, 7-plet, J=6.6 Hz), 6.99 (1H, d, J=9.6 Hz), 7.86 (1H, d, J=9.6 Hz), 8.68 (1H, s)

Mass (ESI): 346 (M+H)$^+$, 368 (M+Na)$^+$

Preparation 23

Under ice-cooling, to a suspension of 6-(1-amino-2-oxo-2-phenylethyl)-2-isopropyl-3(2H)-pyridazinone hydrochloride (1.00 g) and tert-butyl {2-[(2,5-dioxo-1-pyrrolidinyl)oxy]-2-oxoethyl}carbamate (973 mg) in CH$_2$Cl$_2$ (10 ml) was added ethyl(diisopropyl)amine (0.651 ml) and stirred at the same temperature for 2 hours and at 20-25° C. for 18 hours. The mixture was washed with water, dried over MgSO$_4$ and concentrated under reduced pressure to give syrup. The syrup was purified by column chromatography on silica gel (EtOAc only) to give tert-butyl (2-{[1-(1-isopropyl-6-oxo-1,6-dihydro-3-pyridazinyl)-2-oxo-2-phenylethyl]amino}-2-oxoethyl)carbamate as an amorphous solid (1.13 g).

IR (KBr): 3370-3290, 2978, 1714-1649, 1589, 1516 cm$^{-1}$

Mass (ESI): 879 (2M+Na)$^+$, 451 (M+Na)$^+$, 429 (M+H)$^+$ $^1$H NMR (CDCl$_3$, δ): 1.00 (3H, d, J=6.60 Hz), 1.16 (3H, d, J=6.60 Hz), 1.47 (9H, s), 3.88-3.93 (2H, m), 5.03-5.21 (2H, m), 6.54 (1H, d, J=6.98 Hz), 6.87 (1H, d, J=9.56 Hz), 7.35-7.69 (5H, m), 7.95-8.01 (2H, m)

Preparation 24

In a sealed tube, iodomethane (0.6 ml) was added to a solution of 6-[5-amino-3-phenyl-6-(4-pyridyl)-2-pyrazinyl]-2-isopropyl-3(2H)-pyridazinone (120 mg) in THF (3 ml) and the mixture was stirred at 25-35° C. for 18 hours. A precipitate was collected by filtration to give 4-[3-amino-6-(1-isopropyl-6-oxo-1,6-dihydro-3-pyridazinyl)-5-phenyl-2-pyrazinyl]-1-methylpyridinium iodide (152 mg).

m.p.: 166-168° C.

IR (KBr): 3495-3338, 3207, 1643, 1576, 1530 cm$^{-1}$

Mass (ESI): 399 (M–I)$^+$ $^1$H NMR (DMSO-d$_6$, δ): 0.74 (6H, d, J=6.60 Hz), 4.39 (3H, s), 4.90 (1H, 7-plet, J=6.60 Hz), 7.02 (1H, d, J=9.56 Hz), 7.38-7.48 (7H, m), 7.97 (1H, d, J=9.56 Hz), 8.56 (2H, d, J=6.80 Hz), 9.01 (2H, d, J=6.80 Hz)

Preparation 25

3-[3-amino-6-(1-isopropyl-6-oxo-1,6-dihydro-3-pyridazinyl)-5-phenyl-2-pyrazinyl]-1-methylpyridinium iodide The title compound was obtained in a similar manner to that of Preparation 26.

m.p. 250-253° C.

IR (KBr): 3495-3323, 3190, 1643, 1581, 1541, 1504 cm$^{-1}$

Mass (ESI): 399 (M–I)$^+$ $^1$H NMR (DMSO-d$_6$, δ): 0.74 (6H, d, J=6.60 Hz), 4.43 (3H, s), 4.90 (1H, 7-plet, J=6.60 Hz), 7.01 (1H, d, J=9.60 Hz), 7.23 (2H, brs), 7.38-7.45 (5H, m), 7.92 (1H, d, J=9.60 Hz), 8.25 (1H, dd, J=6.08, 8.12 Hz), 8.93 (1H, d, J=8.12 Hz), 9.02 (1H, d, J=6.08 Hz), 9.43 (1H, s)

Preparation 26

A suspension of 3-amino-6-(1-isopropyl-6-oxo-1,6-dihydro-3-pyridazinyl)-2-pyrazinecarbonitrile 4-oxide (500 mg) in 25% hydrogen bromide in AcOH (3 ml) was stirred at 20-25° C. for 4 hours. After addition of dioxane (9 ml), a precipitate was collected by filtration. The precipitate was added in water (3 ml) and adjusted to pH 8 with 1N aq. NaOH solution. The solid was collected by filtration and dried under reduced pressure to give 3-amino-6-(1-isopropyl-6-oxo-1,6-dihydro-3-pyridazinyl)-2-pyrazinecarboxamide 4-oxide (366 mg).

m.p.: >250° C.

IR (KBr): 3533-3386, 2233, 1651, 1641, 1587 cm$^{-1}$

Mass (ESI): 603 (2M+Na)$^+$, 313 (M+Na)$^+$, 291 (M+H)$^+$ $^1$H NMR (DMSO-d$_6$, δ): 1.34 (6H, d, J=6.60 Hz), 5.19 (1H, 7-plet, J=6.60 Hz), 7.05 (1H, d, J=9.65 Hz), 7.93 (1H, brs), 7.9-8.6 (2H, br), 8.63 (1H, brs), 8.66 (1H, d, J=9.65 Hz), 8.89 (1H, s)

Preparation 27

To a suspension 3-amino-6-(1-isopropyl-6-oxo-1,6-dihydro-3-pyridazinyl)-2-pyrazinecarboxamide 4-oxide (1.65 g) in DMF (33 ml), phosphorous oxychloride (1.59 ml) was added below –30° C. and the mixture was stirred at 0-5° C. for one hour. The reaction mixture was poured into ice-water (132 ml), stirred at 40-50° C. for 2 hours, adjusted to pH 8 with 30% aq. NaOH solution under ice-cooling and a precipitate was collected by filtration. The precipitate was purified by column chromatography on silica gel eluting with a mixture of MeOH and EtOAc (2:98 v/v) to give 3-amino-5-chloro-6-(1-isopropyl-6-oxo-1,6-dihydro-3-pyridazinyl)-2-pyrazinecarboxamide as a solid (682 mg).

m.p.: >250° C.

IR (KBr): 3458, 3400, 3278, 3145, 1684, 1664, 1616, 1593, 1523, 1514 cm$^{-1}$

Mass (ESI): 641 and 639 (2M+Na)$^+$, 333 and 331 (M+Na)$^+$, 311 and 309 (M+H)$^+$ $^1$H NMR (DMSO-d$_6$, δ): 1.33 (6H, d, J=6.62 Hz), 5.23 (1H, 7-plet, J=6.62 Hz), 6.99 (1H, d, J=9.67 Hz), 7.79 (1H, brs), 8.0-8.3 (4H, m)

EXAMPLE 1

A solution of methyl [4-(1-isopropyl-6-oxo-1,6-dihydro-3-pyridazinyl)-2-oxo-5-phenyloxazol-3(2H)-yl]acetate (100 mg) in a mixture of conc. HCl (1.5 ml) and AcOH (3.5 ml) was heated at 95-100° C. for 10 hours. The reaction mixture was concentrated under reduced pressure, dissolved in 5% hydrogen chloride solution of MeOH (5 ml) and heated under reflux for 5 hours. After concentration, the residue was dissolved in DMSO (0.5 ml). Ammonium acetate (209 mg) was added to the mixture and heated at 120-125° C. for 10 hours. The reaction mixture was suspended in CHCl$_3$, washed with water, dried over MgSO$_4$ and concentrated under reduced pressure to give a residue. The residue was purified by preparative thin layer chromatography on silica gel (EtOAc) to give 6-(5-hydroxy-3-phenyl-2-pyrazinyl)-2-isopropyl-3(2H)-pyridazinone as a solid (14 mg).

m.p.: 225-227° C. (acetone)

IR (KBr): 1649, 1589 cm$^{-1}$

Mass (ESI): 331 (M+Na)$^+$ $^1$H NMR (CDCl$_3$, δ): 0.80 (6H, d, J=6.60 Hz), 5.05 (1H, 7-plet, J=6.60 Hz), 6.94 (1H, d, J=9.60 Hz), 7.32-7.50 (5H, m), 7.73 (1H, d, J=9.60 Hz), 8.19 (1H, s)

EXAMPLE 2

6-(5-Hydroxy-6-methyl-3-phenyl-2-pyrazinyl)-2-isopropyl-3(2H)-pyridazinone

The title compound was obtained in a similar manner to that of Example 1.

m.p.: >250° C. (acetone-n-hexane)
IR (KBr): 3087-2917, 1678, 1651, 1575 cm$^{-1}$
Mass (ESI): 667 (2M+Na)$^+$, 345 (M+Na)$^+$, 323 (M+H)$^+$
$^1$H NMR (CDCl$_3$, δ): 0.80 (6H, d, J=6.62 Hz), 2.50 (3H, s), 5.04 (1H, 7-plet, J=6.62 Hz), 6.94 (1H, d, J=9.58 Hz), 7.28-7.47 (5H, m), 7.77 (1H, s), 10.7 (1H, brs)

EXAMPLE 3

Potassium carbonate (77 mg) was added to a solution of 6-(5-hydroxy-6-methyl-3-phenyl-2-pyrazinyl)-2-isopropyl-3(2H)-pyridazinone (150 mg) and iodoacetamide (95 mg) in DMA (1 ml) and the mixture was stirred at 20-25° C. for 2 hours. To the reaction mixture, potassium carbonate (235 mg) was added and heated at 150-155° C. for 2 hours. After addition of water, the mixture was extracted with CHCl$_3$, washed with brine, dried over MgSO$_4$ and concentrated under reduced pressure to give a residue. The residue was subjected to column chromatography on silica gel eluting with a mixture of n-hexane and EtOAc (20:80 v/v) to give 6-(5-amino-6-methyl-3-phenyl-2-pyrazinyl)-2-isopropyl-3(2H)-pyridazinone as a solid (97 mg).

m.p.: 208-209.5° C. (MeOH)
IR (KBr): 3284, 3155, 1657, 1616, 1585 cm$^{-1}$
Mass (ESI): 665 (2M+Na)$^+$, 344 (M+Na)$^+$, 322 (M+H)$^+$
$^1$H NMR (CDCl$_3$, δ): 0.84 (6H, d, J=6.60 Hz), 2.50 (3H, s), 4.78 (2H, brs), 5.07 (1H, 7-plet, J=6.60 Hz), 6.94 (1H, d, J=9.55 Hz), 7.26-7.38 (5H, m), 7.76 (1H, d, J=9.55 Hz)

EXAMPLE 4

A mixture of 1-(1-isopropyl-6-oxo-1,6-dihydro-3-pyridazinyl)-2-phenyl-1,2-ethanedione (1.15 g) and 2,3-diamino-2-butenedinitrile (0.46 g) in acetonitrile (6 ml) was heated at 70-75° C. for 3 hours. A reaction mixture was concentrated under reduced pressure and subjected to column chromatography on silica gel eluting with a mixture of n-hexane and EtOAc (60:40 v/v) to give 5-(1-isopropyl-6-oxo-1,6-dihydro-3-pyridazinyl)-6-phenyl-2,3-pyrazinedicarbonitrile as a solid (1.30 g).

m.p.: 201-202° C. (acetone-n-hexane)
IR (KBr): 2247, 1660, 1593, 1518 cm$^{-1}$
Mass (ESI): 365 (M+Na)$^+$
$^1$H NMR (CDCl$_3$, δ): 0.81 (6H, d, J=6.60 Hz), 5.07 (1H, 7-plet, J=6.60 Hz), 7.06 (1H, d, J=9.80 Hz), 7.42-7.57 (5H, m), 7.99 (1H, d, J=9.80 Hz)
$^1$H NMR (DMSO-d$_6$, δ): 0.73 (6H, d, J=6.60 Hz), 4.90 (1H, 7-plet, J=6.60 Hz), 7.11 (1H, d, J=9.85 Hz), 7.47-7.63 (5H, m), 8.03 (1H, d, J=9.85 Hz)

EXAMPLE 5

A mixture of 5-(1-isopropyl-6-oxo-1,6-dihydro-3-pyridazinyl)-6-phenyl-2,3-pyrazinedicarbonitrile (343 mg) and (4-methoxybenzyl)amine (0.137 ml) in DMA (1 ml) was heated at 80-85° C. for 25 hours. After addition of water, a precipitate was collected by filtration, dissolved in CHCl$_3$, dried over MgSO$_4$ and concentrated under reduced pressure to give a residue. The residue was subjected to column chromatography on silica gel eluting with a mixture of n-hexane and EtOAc (60:40 v/v) to give 6-(1-isopropyl-6-oxo-1,6-dihydro-3-pyridazinyl)-3-[(4-methoxybenzyl)amino]-5-phenyl-2-pyrazinecarbonitrile as an amorphous solid (227 mg).

IR (KBr): 2220, 1655, 1562, 1510 cm$^{-1}$
Mass (ESI): 927 (2M+Na)$^+$, 475 (M+Na)$^+$
$^1$H NMR (CDCl$_3$, δ): 0.82 (6H, d, J=6.60 Hz), 3.82 (3H, s), 4.72 (2H, d, J=5.42 Hz), 5.06 (1H, 7-plet, J=6.60 Hz), 5.70 (1H, t, J=5.42 Hz), 6.89-7.00 (3H, m), 7.26-7.43 (7H, m), 7.76 (1H, d, J=9.70 Hz)

EXAMPLE 6

To a solution of 6-(1-isopropyl-6-oxo-1,6-dihydro-3-pyridazinyl)-3-[(4-methoxybenzyl)amino]-5-phenyl-2-pyrazinecarbonitrile (590 mg) in a mixture of water (1.5 ml) and CHCl$_3$ (30 ml) was added 4,5-dichloro-3,6-dioxo-1,4-cyclohexadiene-1,2-dicarbonitrile (888 mg). The reaction mixture was stirred at 25-30° C. for 10 hours, washed with 1N aq. NaOH solution, dried over MgSO$_4$ and concentrated under reduced pressure to give a residue. The residue was subjected to column chromatography on silica gel eluting with a mixture of n-hexane and EtOAc (60:40 v/v) to give 3-amino-6-(1-isopropyl-6-oxo-1,6-dihydro-3-pyridazinyl)-5-phenyl-2-pyrazinecarbonitrile as a solid (335 mg).

m.p.: 231-233° C. (acetone-n-hexane)
IR (KBr): 3410, 3325, 3305, 2227, 1639, 1583, 1543, 1525 cm$^{-1}$
Mass (ESI): 355 (M+Na)$^+$
$^1$H NMR (CDCl$_3$, δ): 0.81 (6H, d, J=6.60 Hz), 5.06 (1H, 7-plet, J=6.60 Hz), 5.46 (2H, brs), 6.98 (1H, d, J=9.58 Hz), 7.39 (5H, s), 7.78 (1H, d, J=9.58 Hz)
$^1$H NMR (DMSO-d$_6$, δ): 0.72 (6H, d, J=6.62 Hz), 4.89 (1H, 7-plet, J=6.62 Hz), 6.98 (1H, d, J=9.65 Hz), 7.39 (5H, s), 7.73 (2H, brs), 7.80 (1H, d, J=9.65 Hz)

EXAMPLE 7

A suspension of 3-amino-6-(1-isopropyl-6-oxo-1,6-dihydro-3-pyridazinyl)-5-phenyl-2-pyrazinecarbonitrile (143 mg) in 25% hydrogen bromide solution of AcOH (1.5 ml) was stirred at 25-30° C. for 2 hours. The reaction mixture was poured into a mixture of Na$_2$CO$_3$ (2 g) and ice-water (30 g), extracted with CHCl$_3$, dried over MgSO$_4$ and concentrated under reduced pressure to give a residue. The residue was subjected to column chromatography on silica gel eluting with a mixture of n-hexane and EtOAc (60:40 v/v) to give 3-amino-6-(1-isopropyl-6-oxo-1,6-dihydro-3-pyridazinyl)-5-phenyl-2-pyrazinecarboxamide as a solid (136 mg).

m.p.: 224-226° C. (MeOH)
IR (KBr): 3411, 3338, 3273, 1657, 1585 cm$^{-1}$
Mass (ESI): 373 (M+Na)$^+$
$^1$H NMR (CDCl$_3$, δ): 0.85 (6H, d, J=6.60 Hz), 5.08 (1H, 7-plet, J=6.60 Hz), 5.58 (1H, brs), 6.97 (1H, d, J=9.60 Hz), 7.33-7.41 (5H, m), 7.61 (1H, brs), 7.68 (1H, d)
$^1$H NMR (DMSO-d$_6$, δ): 0.71 (6H, d, J=6.60 Hz), 4.87 (1H, 7-plet, J=6.60 Hz), 6.97 (1H, d, J=9.70 Hz), 7.39 (5H, s), 7.72 (1H, brs), 7.88 (2H, brs), 8.26 (1H, d, J=9.70 Hz), 8.29 (1H, brs)

EXAMPLE 8

A suspension of 3-amino-6-(1-isopropyl-6-oxo-1,6-dihydro-3-pyridazinyl)-5-phenyl-2-pyrazinecarboxamide (1.02 g) in a mixture of conc. HCl (40 ml) and dioxane (10 ml) was heated at 90-95° C. for 20 hours. Under ice-cooling, the reaction mixture was adjusted to pH 4 with 4N aq. NaOH solution to yield a precipitate. The precipitate was collected by filtration and dried at 60° C. under reduced pressure to give 3-amino-6-(1-isopropyl-6-oxo-1,6-dihydro-3-pyridazinyl)-5-phenyl-2-pyrazinecarboxylic acid as a solid (878 mg).

m.p.: 233-235° C. (water)

IR (KBr): 3433, 3303, 1711, 1649, 1639, 1595, 1581 cm$^{-1}$

Mass (ESI): 374 (M+Na)$^+$, 352 (M+H)$^+$, 330 (M+Na-CO$_2$)$^+$ $^1$H NMR (DMSO-d$_6$, δ): 0.72 (6H, d, J=6.60 Hz), 4.88 (1H, 7-plet, J=6.60 Hz), 7.01 (1H, d, J=9.63 Hz), 7.36-7.43 (5H, m), 7.72 (2H, brs), 8.00 (1H, d, J=9.63 Hz), 13.17 (1H, brs)

EXAMPLE 9

A suspension of 3-amino-6-(1-isopropyl-6-oxo-1,6-dihydro-3-pyridazinyl)-5-phenyl-2-pyrazinecarboxylic acid (250 mg) in o-dichlorobenzene (1.25 ml) was refluxed for 2 hours. After cooling, IPE (2.5 ml) was added to the reaction mixture to yield a precipitate. The precipitate was collected by filtration to give 6-(5-amino-3-phenyl-2-pyrazinyl)-2-isopropyl-3(2H)-pyridazinone as a solid (205 mg).

m.p.: 204-206° C. (EtOAc)

IR (KBr): 3406, 3294, 3176, 1649, 1587, 1564, 1537 cm$^{-1}$

Mass (ESI): 637 (2M+Na)$^+$, 330 (M+Na)$^+$, 308 (M+H)$^+$ $^1$H NMR (CDCl$_3$, δ): 0.85 (6H, d, J=6.60 Hz), 4.94 (2H, brs), 5.08 (1H, 7-plet, J=6.60 Hz), 6.94 (1H, d, J=9.60 Hz), 7.27-7.40 (5H, m), 7.73 (1H, d, J=9.60 Hz), 7.98 (1H, s)

EXAMPLE 10

A suspension of 3-amino-6-(1-isopropyl-6-oxo-1,6-dihydro-3-pyridazinyl)-5-phenyl-2-pyrazinecarbonitrile (1.00 g) in a mixture of 2N aq. NaOH solution (20 ml) and dioxane (2 ml) was refluxed for 3 hours. The reaction mixture was adjusted to pH 5 with conc. HCl to yield a precipitate. The precipitate was collected by filtration and dried at 60° C. under reduced pressure to give 3-amino-6-(1-isopropyl-6-oxo-1,6-dihydro-3-pyridazinyl)-5-phenyl-2-pyrazinecarboxylic acid as a solid (1.01 g).

m.p.: 233-235° C. (water)

IR (KBr): 3433, 3303, 1711, 1649, 1639, 1595, 1581 cm$^{-1}$

Mass (ESI): 374 (M+Na)$^+$, 352 (M+H)$^+$, 330 (M+Na-CO$_2$)$^+$ $^1$H NMR (DMSO-d$_6$, δ): 0.72 (6H, d, J=6.60 Hz), 4.88 (1H, 7-plet, J=6.60 Hz), 7.01 (1H, d, J=9.63 Hz), 7.36-7.43 (5H, m), 7.72 (2H, brs), 8.00 (1H, d, J=9.63 Hz), 13.17 (1H, brs)

EXAMPLE 11

5-(1-Ethyl-6-oxo-1,6-dihydro-3-pyridazinyl)-6-phenyl-2,3-pyrazinedicarbonitrile

The title compound was obtained in a similar manner to that of Example 4.

m.p.: 201-203° C. (acetone suspension)

IR (KBr): 2247, 1668, 1512 cm$^{-1}$

Mass (ESI): 351 (M+Na)$^+$, 329 (M+H)$^+$ $^1$HNMR (DMSO-d$_6$, δ): 0.78 (3H, t, J=7.20 Hz), 3.76 (2H, q, J=7.20 Hz), 7.09 (1H, d, J=9.71 Hz), 7.43-7.62 (5H, m), 7.94 (1H, d, J=9.71 Hz)

EXAMPLE 12

6-(1-Ethyl-6-oxo-1,6-dihydro-3-pyridazinyl)-3-[(4-methoxybenzyl)amino]-5-phenyl-2-pyrazinecarbonitrile The title compound was obtained in a similar manner to that of Example 5.

m.p.: 165.5-167.5° C. (acetone-n-hexane)

IR (KBr): 3365, 2220, 1669, 1666, 1570 cm$^{-1}$

Mass (ESI): 461 (M+Na)$^+$, 439 (M+H)$^+$ $^1$H NMR (CDCl$_3$, δ): 0.95 (3H, t, J=7.22 Hz), 3.82 (3H, s), 3.90 (2H, q, J=7.22 Hz), 4.72 (2H, d, J=5.50 Hz), 5.78 (1H, t, J=5.50 Hz), 6.88-6.96 (3H, m), 7.27-7.46 (7H, m), 7.63 (1H, d, J=9.60 Hz)

EXAMPLE 13

3-Amino-6-(1-ethyl-6-oxo-1,6-dihydro-3-pyridazinyl)-5-phenyl-2-pyrazinecarbonitrile The title compound was obtained in a similar manner to that of Example 6.

m.p.: >250° C. (acetone suspension)

IR (KBr): 3406, 3170, 2227, 1643, 1583, 1547 cm$^{-1}$

Mass (ESI): 659 (2M+Na)$^+$, 341 (M+Na)$^+$, 319 (M+H)$^+$ $^1$H NMR (DMSO-d$_6$, δ): 0.77 (3H, t, J=7.17 Hz), 3.74 (2H, q, J=7.17 Hz), 6.97 (1H, d, J=9.63 Hz), 7.40 (5H, s), 7.71 (1H, d), 7.74 (2H, s)

EXAMPLE 14

3-Amino-6-(1-ethyl-6-oxo-1,6-dihydro-3-pyridazinyl)-5-phenyl-2-pyrazinecarboxamide The title compound was obtained in a similar manner to that of Example 7.

m.p.: >250° C. (acetone suspension)

IR (KBr): 3448, 3408, 3261, 3161, 1682, 1653, 1616, 1587 cm$^{-1}$

Mass (ESI): 359 (M+Na)$^+$ $^1$H NMR (DMSO-d$_6$, δ): 0.74 (3H, t, J=7.15 Hz), 3.67 (2H, q, J=7.15 Hz), 6.97 (1H, d, J=9.64 Hz), 7.39 (5H, s), 7.7-8.1 (2H, br-peak), 7.72 (1H, brs), 8.21 (1H, d, J=9.64 Hz), 8.27 (1H, brs)

EXAMPLE 15

5-(1-Methyl-6-oxo-1,6-dihydro-3-pyridazinyl)-6-phenyl-2,3-pyrazinedicarbonitrile The title compound was obtained in a similar manner to that of Example 4.

m.p.: 210-212° C. (acetone suspension)

IR (KBr): 2247, 1672, 1591, 1514 cm$^{-1}$

Mass (ESI): 315 (M+H)$^+$ $^1$H NMR (DMSO-d$_6$, δ): 3.39 (3H, s), 7.04 (1H, d, J=9.68 Hz), 7.44-7.61 (5H, m), 7.78 (1H, d, J=9.68 Hz)

EXAMPLE 16

3-[(4-Methoxybenzyl)amino]-6-(1-methyl-6-oxo-1,6-dihydro-3-pyridazinyl)-5-phenyl-2-pyrazinecarbonitrile The title compound was obtained in a similar manner to that of Example 5.

m.p.: 166.5-168° C. (acetone-n-hexane)

IR (KBr): 3361, 2218, 1672, 1574 cm$^{-1}$

Mass (ESI): 871 (2M+Na)$^+$, 447 (M+Na)$^+$, 425 (M+H)$^+$

¹H NMR (CDCl₃, δ): 3.54 (3H, s), 3.82 (3H, s), 4.72 (2H, d, J=5.42 Hz), 5.75 (1H, t, J=5.42 Hz), 6.85-6.93 (3H, m), 7.26-7.49 (8H, m)

EXAMPLE 17

3-Amino-6-(1-methyl-6-oxo-1,6-dihydro-3-pyridazinyl)-5-phenyl-2-pyrazinecarbonitrile The title compound was obtained in a similar manner to that of Example 6.
m.p.: >250° C. (acetone suspension)
IR (KBr): 3330, 3172, 2222, 1649, 1626, 1579, 1531 cm⁻¹
Mass (ESI): 631 (2M+Na)⁺, 327 (M+Na)⁺, 305 (M+H)⁺
¹H NMR (DMSO-d₆, δ): 3.33 (3H, s), 6.91 (1H, d, J=9.62 Hz), 7.41 (5H, s), 7.55 (1H, d, J=9.62 Hz), 7.75 (2H, brs)

EXAMPLE 18

3-Amino-6-(1-methyl-6-oxo-1,6-dihydro-3-pyridazinyl)-5-phenyl-2-pyrazinecarboxamide The title compound was obtained in a similar manner to that of Example 7.
m.p.: >250° C. (acetone suspension)
IR (KBr): 3367, 3269, 3219, 1658, 1591 cm⁻¹
Mass (ESI): 345 (M+Na)⁺, 323 (M+H)⁺
¹H NMR (DMSO-d₆, δ): 3.33 (3H, s), 6.94 (1H, d, J=9.70 Hz), 7.39 (5H, s), 7.7-8.1 (2H, br-peak), 7.73 (1H, brs), 8.14(1H, d, J=9.70 Hz), 8.26 (1H, brs)

EXAMPLE 19

3-Amino-6-(1-methyl-6-oxo-1,6-dihydro-3-pyridazinyl)-5-phenyl-2-pyrazinecarboxylic acid The title compound was obtained in a similar manner to that of Example 10.
m.p.: 238° C. (dec.) (water)
IR (KBr): 3417, 3275, 3178, 1693, 1643, 1624, 1572, 1545, 1512 cm⁻¹
Mass (ESI, Neg): 322 (M−H)⁻
¹H NMR (DMSO-d₆, δ): 3.32 (3H, s), 6.95 (1H, d, J=9.62 Hz), 7.41 (5H, s), 7.73 (2H, brs), 7.78 (1H, d, J=9.62 Hz), 13.21 (1H, brs)

EXAMPLE 20

6-(5-Amino-3-phenyl-2-pyrazinyl)-2-methyl-3(2H)-pyridazinone

The title compound was obtained in a similar manner to that of Example 9.
m.p.: 202-204° C. (EtOAc)
IR (KBr): 3431, 3330, 3219, 1650, 1620, 1568, 1535 cm⁻¹
Mass (ESI): 581 (2M+Na)⁺, 302 (M+Na)⁺, 280 (M+H)⁺
¹H NMR (CDCl₃, δ): 3.65 (3H, s), 4.92 (2H, brs), 6.78 (1H, d, J=9.60 Hz), 7.24 (1H, d, J=9.60 Hz), 7.33-7.44 (5H, m), 8.04 (1H, s)
¹H NMR (DMSO-d₆, δ): 3.34 (3H, s), 6.87 (1H, d, J=9.62 Hz), 6.90 (2H, brs), 7.35 (5H, s), 7.52 (1H, d, J=9.62 Hz), 7.93 (1H, s)

EXAMPLE 21

A suspension of 5-(1-isopropyl-6-oxo-1,6-dihydro-3-pyridazinyl)-6-phenyl-2,3-pyrazinedicarbonitrile (1.00 g) in a mixture of 28% aq. ammonia (1 ml) and THF (3 ml) was stirred at 25-30° C. for 40 hours. After addition of water, the mixture was extracted with CHCl₃, dried over MgSO₄, concentrated under reduced pressure and subjected to column chromatography on silica gel eluting with a mixture of n-hexane and EtOAc (50:50 v/v). A less polar one is 3-amino-6-(1-isopropyl-6-oxo-1,6-dihydro-3-pyridazinyl)-5-phenyl-2-pyrazinecarbonitrile (350 mg) and a more polar one is 3-amino-5-(1-isopropyl-6-oxo-1,6-dihydro-3-pyridazinyl)-6-phenyl-2-pyrazinecarbonitrile (51 mg).

3-Amino-6-(1-isopropyl-6-oxo-1,6-dihydro-3-pyridazinyl)-5-phenyl-2-pyrazinecarbonitrile
m.p.: 231-233° C. (acetone-n-hexane)
IR (KBr): 3410, 3325, 3305, 2227, 1639, 1583, 1543, 1525 cm⁻¹
Mass (ESI): 355 (M+Na)⁺
¹H NMR (CDCl₃, δ): 0.81 (6H, d, J=6.60 Hz), 5.06 (1H, 7-plet, J=6.60 Hz), 5.44 (2H, brs), 6.98 (1H, d, J=9.58 Hz), 7.39 (5H, s), 7.78 (1H, d, J=9.58 Hz)
¹H NMR (DMSO-d₆, δ): 0.72 (6H, d, J=6.60 Hz), 4.88 (1H, 7-plet, J=6.60 Hz), 6.97 (1H, d, J=9.65 Hz), 7.39 (5H, s), 7.73 (2H, brs), 7.80 (1H, d, J=9.65 Hz)

3-Amino-5-(1-isopropyl-6-oxo-1,6-dihydro-3-pyridazinyl)-6-phenyl-2-pyrazinecarbonitrile
m.p.: 238-241° C. (acetone-n-hexane)
IR (KBr): 3354, 3313, 3294, 3199, 2220, 1651, 1628, 1583, 1552, 1525 cm⁻¹
Mass (ESI): 355 (M+Na)⁺
¹H NMR (CDCl₃, δ): 0.82 (6H, d, J=6.60 Hz), 5.06 (1H, 7-plet, J=6.60 Hz), 5.33 (2H, brs), 6.97 (1H, d, J=9.58 Hz), 7.28-7.40 (5H, m), 7.77 (1H, d, J=9.58 Hz)

EXAMPLE 22

A suspension of 5-(1-isopropyl-6-oxo-1,6-dihydro-3-pyridazinyl)-6-phenyl-2,3-pyrazinedicarbonitrile (100 mg) in a 2M solution of ammonia in MeOH (3 ml) was stirred at 25-35° C. for 30 hours in a sealed tube. The mixture was concentrated under reduced pressure and subjected to column chromatography on silica gel eluting with a mixture of n-hexane and EtOAc (60:40 v/v) to give 6-(1-isopropyl-6-oxo-1,6-dihydro-3-pyridazinyl)-3-methoxy-5-phenyl-2-pyrazinecarbonitrile as a solid (32 mg).
m.p.: 170-172° C. (acetone-n-hexane)
IR (KBr): 2227, 1664, 1591, 1541, 1508 cm⁻¹
Mass (ESI): 717 (2M+Na)⁺, 370 (M+Na)⁺, 348 (M+H)⁺
¹H NMR (CDCl₃, δ): 0.83 (6H, d, J=6.60 Hz), 4.20 (3H, s), 5.08 (1H, 7-plet, J=6.60 Hz), 7.01 (1H, d, J=9.58 Hz), 7.38-7.50 (5H, m), 7.80 (1H, d, J=9.58 Hz)
¹H NMR (DMSO-d₆, δ): 0.75 (6H, d, J=6.60 Hz), 4.15 (3H, s), 4.91 (1H, 7-plet, J=6.60 Hz), 7.05 (1H, d, J=9.70 Hz), 7.43-7.57 (5H, m), 7.86 (1H, d, J=9.70 Hz)

EXAMPLE 23

To a solution of 5-(1-isopropyl-6-oxo-1,6-dihydro-3-pyridazinyl)-6-phenyl-2,3-pyrazinedicarbonitrile (343 mg) in EtOH (10 ml) was dropwise added a solution of sodium molybdate dihydrate (12.1 mg) in a mixture of 30% hydrogen peroxide solution in water (0.57 ml) and EtOH (1.5 ml) and the mixture was stirred at 40-45° C. for 3 hours. After ice-cooling, a precipitate was collected by filtration to give 3-cyano-5-(1-isopropyl-6-oxo-1,6-dihydro-3-pyridazinyl)-6-phenyl-2-pyrazinecarboxamide as a solid (171 mg).

Saturated sodium thiosulfate solution in water was added to the filtrate. After removal of EtOH under reduced pressure, the mixture was extracted with CHCl₃, dried over MgSO₄ and concentrated under reduced pressure to give a residue. The residue was subjected to column chromatography on silica gel. With elution of a mixture of n-hexane and EtOAc (50:50 v/v) was obtained 3-cyano-6-(1-isopropyl-6-oxo-1,6-dihydro-3-pyridazinyl)-5-phenyl-2-pyrazinecarboxamide as a solid (78 mg) and with elution of EtOAc was obtained 3-cyano-5-(1-isopropyl-6-oxo-1,6-dihydro-3-pyridazinyl)-6-phenyl-2-pyrazinecarboxamide as a solid (22 mg).

3-Cyano-5-(1-isopropyl-6-oxo-1,6-dihydro-3-pyridazinyl)-6-phenyl-2-pyrazinecarboxamide m.p.: >250° C.
IR (KBr): 3352, 3161, 2233, 1709, 1666, 1593 cm$^{-1}$
Mass (ESI): 743 (2M+Na)$^+$, 383 (M+Na)$^+$
$^1$H NMR (CDCl$_3$, δ): 0.85 (6H, d, J=6.60 Hz), 5.10 (1H, 7-plet, J=6.60 Hz), 6.13 (1H, brs), 7.06 (1H, d, J=9.60 Hz), 7.42-7.56 (6H, m), 7.89 (1H, d, J=9.60 Hz)
$^1$H NMR (DMSO-d$_6$, δ): 0.71 (6H, d, J=6.57 Hz), 4.90 (1H, 7-plet, J=6.57 Hz), 7.11 (1H, d, J=9.80 Hz), 7.45-7.61 (5H, m), 8.21 (1H, brs), 8.50 (1H, d, J=9.80 Hz), 8.66 (1H, brs)

3-Cyano-6-(1-isopropyl-6-oxo-1,6-dihydro-3-pyridazinyl)-5-phenyl-2-pyrazinecarboxamide m.p.: 195-197° C.
IR (KBr): 3483, 3344, 2233, 1707, 1655, 1585, 1523 cm$^{-1}$
Mass (ESI): 743 (2M+Na)$^+$, 383 (M+Na)$^+$
$^1$H NMR (DMSO-d$_6$, δ): 0.75 (6H, d, J=6.60 Hz), 4.92 (1H, 7-plet, J=6.60 Hz), 7.10 (1H, d, J=9.62 Hz), 7.44-7.50 (3H, m), 7.68-7.74 (2H, m), 8.01 (1H, d, J=9.62 Hz), 8.20 (1H, brs), 8.46 (1H, brs)

EXAMPLE 24

To a solution of sodium methoxide (81.5 mg) in MeOH (3 ml), 5-(1-isopropyl-6-oxo-1,6-dihydro-3-pyridazinyl)-6-phenyl-2,3-pyrazinedicarbonitrile (172 mg) was added and the mixture was stirred at 25-30° C. for 10 hours. After addition of conc. HCl (1.5 ml), the reaction mixture was stirred at 25-30° C. for 20 hours. Water and CHCl$_3$ were added to the mixture. An organic layer was collected, dried over MgSO$_4$, concentrated under reduced pressure and subjected to column chromatography on silica gel. With elution of a mixture of n-hexane and EtOAc (70:30 v/v) was obtained 6-(1-isopropyl-6-oxo-1,6-dihydro-3-pyridazinyl)-3-methoxy-5-phenyl-2-pyrazinecarbonitrile as a solid (43 mg) and with elution of a mixture of n-hexane and EtOAc (50:50 v/v) was obtained methyl 6-(1-isopropyl-6-oxo-1,6-dihydro-3-pyridazinyl)-3-methoxy-5-phenyl-2-pyrazinecarboxylate as a solid (67 mg).

6-(1-Isopropyl-6-oxo-1,6-dihydro-3-pyridazinyl)-3-methoxy-5-phenyl-2-pyrazinecarbonitrile m.p.: 170-172° C. (acetone-n-hexane)
IR (KBr): 2227, 1664, 1591, 1541, 1508 cm$^{-1}$
Mass (ESI): 717 (2M+Na)$^+$, 370 (M+Na)$^+$, 348 (M+H)$^+$
$^1$H NMR (CDCl$_3$, δ): 0.83 (6H, d, J=6.60 Hz), 4.20 (3H, s), 5.08 (1H, 7-plet, J=6.60 Hz), 7.01 (1H, d, J=9.58 Hz), 7.38-7.50 (5H, m), 7.80 (1H, d, J=9.58 Hz)
$^1$H NMR (DMSO-d$_6$, δ): 0.75 (6H, d, J=6.60 Hz), 4.15 (3H, s), 4.91 (1H, 7-plet, J=6.60 Hz), 7.05 (1H, d, J=9.70 Hz), 7.43-7.57 (5H, m), 7.86 (1H, d, J=9.70 Hz)

Methyl 6-(1-isopropyl-6-oxo-1,6-dihydro-3-pyridazinyl)-3-methoxy-5-phenyl-2-pyrazinecarboxylate m.p.: 170-171° C. (acetone-n-hexane)
IR (KBr): 1734, 1662, 1593, 1541 cm$^{-1}$
Mass (ESI): 403 (M+Na)$^+$, 381 (M+H)$^+$
$^1$H NMR (CDCl$_3$, δ): 0.84 (6H, d, J=6.60 Hz), 4.02 (3H, s), 4.17 (3H, s), 5.09 (1H, 7-plet, J=6.60 Hz), 7.00 (1H, d, J=9.56 Hz), 7.34-7.51 (5H, m), 7.85 (1H, d, J=9.56 Hz)

EXAMPLE 25

A suspension of 5-(1-isopropyl-6-oxo-1,6-dihydro-3-pyridazinyl)-6-phenyl-2,3-pyrazinedicarbonitrile (343 mg) and sodium diformylamide (190 mg) in DMA (1 ml) was heated at 100-105° C. for an hour. After addition of water, the reaction mixture was extracted with CHCl$_3$, dried over MgSO$_4$, concentrated under reduced pressure and subjected to column chromatography on silica gel. With elution of a mixture of n-hexane and EtOAc (50:50 v/v) was obtained [3-cyano-5-(1-isopropyl-6-oxo-1,6-dihydro-3-pyridazinyl)-6-phenyl-2-pyrazinyl]formamide as a solid (30 mg) and with elution of a mixture of n-hexane and EtOAc (30:70 v/v) was obtained [3-cyano-6-(1-isopropyl-6-oxo-1,6-dihydro-3-pyridazinyl)-5-phenyl-2-pyrazinyl]-formamide as a solid (22 mg).

[3-Cyano-5-(1-isopropyl-6-oxo-1,6-dihydro-3-pyridazinyl)-6-phenyl-2-pyrazinyl]formamide m.p.: 198-200° C. (acetone-n-hexane)
IR (KBr): 2227, 1703, 1662, 1556, 1539 cm$^{-1}$
Mass (ESI): 383 (M+Na)$^+$, 361 (M+H)$^+$
$^1$H NMR (CDCl$_3$, δ): 0.82 (6H, d, J=6.60 Hz), 5.07 (1H, 7-plet, J=6.60 Hz), 7.02 (1H, d, J=9.58 Hz), 7.38-7.50 (5H, m), 7.84 (1H, d, J=9.58 Hz), 8.27 (1H, d, J=9.05 Hz), 9.59 (1H, d, J=9.05 Hz)

[3-Cyano-6-(1-isopropyl-6-oxo-1,6-dihydro-3-pyridazinyl)-5-phenyl-2-pyrazinyl]formamide m.p.: 206-208° C. (acetone-n-hexane)
IR (KBr): 2233, 1707, 1655, 1558 cm$^{-1}$
Mass (ESI): 383 (M+Na)$^+$, 361 (M+H)$^+$
$^1$H NMR (CDCl$_3$, δ): 0.87 (6H, d, J=6.60 Hz), 5.09 (1H, 7-plet, J=6.60 Hz), 7.02 (1H, d, J=9.62 Hz), 7.41 (5H, s), 7.82 (1H, d, J=9.62 Hz), 8.39 (1H, brs), 9.54 (1H, brs)

EXAMPLE 26

To a suspension of 3-amino-6-(1-isopropyl-6-oxo-1,6-dihydro-3-pyridazinyl)-5-phenyl-2-pyrazinecarbonitrile (665 mg) and thioacetamide (451 mg) in DMF (3.2 ml) was added a 4N hydrogen chloride solution of dioxane (3.2 ml) and the mixture was stirred at 100-105° C. for 2 hours. Water (65 ml) was added to the mixture to yield a precipitate. The precipitate was collected by filtration, subjected to column chromatography on silica gel eluting with a mixture of n-hexane and EtOAc (40:60 v/v) to give a solid. The solid triturated with acetone and collected by filtration to give 3-amino-6-(1-isopropyl-6-oxo-1,6-dihydro-3-pyridazinyl)-5-phenyl-2-pyrazinecarbothioamide as a solid (417 mg).

m.p.: >250° C. (acetone suspension)
IR (KBr): 3363, 3261, 3159, 1660, 1585, 1533 cm$^{-1}$
Mass (ESI): 389 (M+Na)$^+$
$^1$H NMR (DMSO-d$_6$, δ): 0.70 (6H, d, J=6.61 Hz), 4.87 (1H, 7-plet, J=6.61 Hz), 6.98 (1H, d, J=9.62 Hz), 7.40-7.48 (5H, m), 8.29 (1H, d, J=9.62 Hz), 8.57 (2H, brs), 9.85 (1H, brs), 10.00 (1H, brs)

EXAMPLE 27

A solution of 3-amino-6-(1-isopropyl-6-oxo-1,6-dihydro-3-pyridazinyl)-5-phenyl-2-pyrazinecarbothioamide (100 mg) and 1-chloroacetone (37.9 mg) in DMF (0.27 ml) was heated at 100-105° C. for 10 hours. After cooling, sat. aq.

NaHCO₃ solution (0.5 ml) and water (1 ml) were added to the mixture to yield a precipitate. The precipitate was collected by filtration, dissolved in CHCl₃, dried over MgSO₄ and concentrated under reduced pressure to give a residue. The residue was subjected to column chromatography on silica gel eluting with a mixture of n-hexane and EtOAc (60:40 v/v) to give 6-[5-amino-6-(4-methyl-thiazol-2-yl)-3-phenyl-2-pyrazinyl]-2-isopropyl-3(2H)-pyridazinone as a solid (58 mg).

m.p.: 238-240° C. (acetone-n-hexane)
IR (KBr): 3325, 1668, 1628, 1589 cm⁻¹
Mass (ESI): 831 (2M+Na)⁺, 427 (M+Na)⁺, 405 (M+H)⁺
¹H NMR (CDCl₃, δ): 0.83 (6H, d, J=6.65 Hz), 2.54 (3H, s), 5.08 (1H, 7-plet, J=6.65 Hz), 6.96-7.02 (2H, m), 7.28-7.45 (6H, m), 7.90 (1H, d, J=9.64 Hz)

EXAMPLE 28

6-[5-Amino-3-phenyl-6-(4-phenyl-thiazol-2-yl)-2-pyrazinyl]-2-isopropyl-3(2H)-pyridazinone The title compound was obtained in a similar manner to that of Example 27.

m.p.: 240-242° C. (MeOH suspension)
IR (KBr): 3386, 3278, 1660, 1612, 1587 cm⁻¹
Mass (ESI): 489 (M+Na)⁺, 467 (M+H)⁺
¹H NMR (CDCl₃, δ): 0.76 (6H, d, J=6.60 Hz), 4.91 (1H, 7-plet, J=6.60 Hz), 7.06 (1H, d, J=9.65 Hz), 7.32-7.57 (8H, m), 8.02 (1H, d, J=9.65 Hz), 8.04-8.09 (2H, m), 8.21 (2H, brs), 8.35 (1H, s)

EXAMPLE 29

3-Amino-5-(1-isopropyl-6-oxo-1,6-dihydro-3-pyridazinyl)-6-phenyl-2-pyrazinecarboxamide The title compound was obtained in a similar manner to that of Example 7.

m.p.: 217-220° C. (acetone-n-hexane)
IR (KBr): 3442, 3305, 1658, 1589 cm⁻¹
Mass (ESI): 723 (2M+Na)⁺, 373 (M+Na)⁺, 351 (M+H)⁺
¹H NMR (CDCl₃, δ): 0.83 (6H, d, J=6.60 Hz), 5.07 (1H, 7-plet, J=6.60 Hz), 5.60 (1H, brs), 6.97 (1H, d, J=9.56 Hz), 7.26-7.40 (5H, m), 7.77 (1H, brs), 7.80 (1H, d, J=9.56 Hz)

EXAMPLE 30

A mixture of ethyl {[1-(1-isopropyl-6-oxo-1,6-dihydro-3-pyridazinyl)-2-oxo-2-phenylethyl]amino}acetate (14.0 g) and ammonium acetate (21.0 g) in AcOH (60 ml) was refluxed with stirring for 2 hours. Water, aq. NaHCO₃ and EtOAc were added to the reaction mixture. The organic layer was separated, and dried over MgSO₄. The solvent was removed in vacuo. The residue was purified by silica gel column chromatography eluted with a mixture of n-hexane and EtOAc. The fractions were concentrated in vacuo to obtain 6-(5-hydroxy-3-phenyl-2-pyrazinyl)-2-isopropyl-3(2H)-pyridazinone (3.0 g) as white powder.

¹H NMR (DMSO-d₆, δ): 0.73 (6H, d, J=6.6 Hz), 4.87 (1H, 7-plet, J=6.6 Hz), 6.95 (1H, d, J=9.6 Hz), 7.2-7.5 (5H, m), 7.77 (1H, d, J=9.6 Hz), 8.12 (1H, s), 12-13 (1H, br)
Mass (ESI, Neg): 307 (M−H)⁺

EXAMPLE 31

6-(5-Amino-3-phenyl-2-pyrazinyl)-2-isopropyl-3(2H)-pyridazinone

The title compound was obtained in a similar manner to that of Example 3.

¹H NMR (DMSO-d₆, δ): 0.73 (6H, d, J=6.6 Hz), 4.88(1H, 7-plet, J=6.6 Hz), 6.89 (2H, br), 6.95 (1H, d, J=9.6 Hz), 7.2-7.4 (5H, m), 7.80 (1H, d, J=9.6 Hz), 7.93 (1H, s)
Mass (ESI): 308 (M+H)⁺, 330 (M+Na)⁺

EXAMPLE 32

A mixture of 6-(5-amino-3-phenyl-2-pyrazinyl)-2-isopropyl-3(2H)-pyridazinone (50 mg), N-chlorosuccinimide (23.9 mg) in DMF (1.5 ml) was stirred at 60° C. for 2 hours. Water and EtOAc were added to the reaction mixture. The organic layer was separated, and dried over Na₂SO₄. The solvent was removed in vacuo. The residue was purified by silica gel column chromatography eluted with a mixture of CHCl₃ and MeOH. The fractions were concentrated in vacuo to obtain 6-(5-amino-6-chloro-3-phenyl-2-pyrazinyl)-2-isopropyl-3(2H)-pyridazinone (30 mg) as white powder.

¹H NMR (DMSO-d₆, δ): 0.74 (6H, d, J=6.6 Hz), 4.88 (1H, 7-plet, J=6.6 Hz), 6.95 (1H, d, J=9.6 Hz), 7.26 (2H, br), 7.3-7.5 (5H, m), 7.76 (1H, d, J=9.6 Hz)
Mass (ESI): 364 (M+Na)⁺

EXAMPLE 33

6-(5-Amino-6-bromo-3-phenyl-2-pyrazinyl)-2-isopropyl-3(2H)-pyridazinone

The title compound was obtained in a similar manner to that of Example 32.

¹H NMR (DMSO-d₆, δ): 0.73 (6H, d, J=6.6 Hz), 4.88 (1H, 7-plet, J=6.6 Hz), 6.95 (1H, d, J=9.6 Hz), 7.18 (2H, br), 7.3-7.5 (5H, m), 7.76 (1H, d, J=9.6 Hz)
Mass (ESI): 408 (M+Na)⁺, 410 (M+Na+2)⁺

EXAMPLE 34

6-(5-Amino-6-iodo-3-phenyl-2-pyrazinyl)-2-isopropyl-3(2H)-pyridazinone

The title compound was obtained in a similar manner to that of Example 32.

¹H NMR (DMSO-d₆, δ): 0.73 (6H, d, J=6.6 Hz), 4.88 (1H, 7-plet, J=6.6 Hz), 6.8-7.0 (3H, m), 7.2-7.4 (5H, m), 7.76 (1H, d, J=9.6 Hz)
Mass (ESI): 456 (M+Na)⁺

EXAMPLE 35

6-[3-(4-Fluorophenyl)-5-hydroxy-2-pyrazinyl]-2-isopropyl-3(2H)-pyridazinone

The title compound was obtained in a similar manner to that of Example 30.

¹H NMR (DMSO-d₆, δ): 0.77 (6H, d, J=6.6 Hz), 4.91 (1H, 7-plet, J=6.6 Hz), 5.0-6.0 (1H, br), 6.94 (1H, d, J=9.6 Hz), 7.1-7.5 (4H, m), 7.80 (1H, d, J=9.6 Hz), 7.97 (1H, s)
Mass (ESI, Neg): 325 (M−H)⁺

EXAMPLE 36

6-[5-Amino-3-(4-fluorophenyl)-2-pyrazinyl]-2-isopropyl-3(2H)-pyridazinone

The title compound was obtained in a similar manner to that of Example 3.

¹H NMR (DMSO-d₆, δ): 0.77 (6H, d, J=6.6 Hz), 4.91 (1H, 7-plet, J=6.6 Hz), 6.91 (2H, br), 6.95 (1H, d, J=9.6 Hz), 7.1-7.5 (4H, m), 7.80 (1H, d, J=9.6 Hz), 7.92 (1H, s)
Mass (ESI): 326 (M+H)⁺, 330 (M+Na)⁺

EXAMPLE 37

6-[5-Amino-6-chloro-3-(4-fluorophenyl)-2-pyrazinyl]-2-isopropyl-3(2H)-pyridazinone The title compound was obtained in a similar manner to that of Example 32.

$^1$H NMR (DMSO-d$_6$, δ): 0.77 (6H, d, J=6.6 Hz), 4.91 (1H, 7-plet, J=6.6 Hz), 6.96 (1H, d, J=9.6 Hz), 7.1-7.5 (6H, m), 7.75 (1H, d, J=9.6 Hz)

Mass (ESI): 360 (M+H)$^+$, 382 (M+Na)$^+$

EXAMPLE 38

2-Isopropyl-6-(3-phenyl-2-pyrazinyl)-3(2H)-pyridazinone

The title compound was obtained in a similar manner to that of Example 4.

$^1$H NMR (DMSO-d$_6$, δ): 0.85 (6H, d, J=6.6 Hz), 5.01 (1H, 7-plet, J=6.6 Hz), 7.00 (1H, d, J=9.6 Hz), 7.2-7.5 (6H, m), 7.87 (1H, d, J=9.6 Hz), 8.58 (1H, d, J=2.5 Hz), 8.67 (1H, d, J=2.5 Hz)

Mass (ESI): 293 (M+H)$^+$, 315 (M+Na)$^+$

EXAMPLE 39

A mixture of 6-(5-hydroxy-3-phenyl-2-pyrazinyl)-2-isopropyl-3(2H)-pyridazinone (200 mg), 2,6-lutidine (139 mg) and trifluoromethane sulfonic anhydride (257 mg) in CH$_2$Cl$_2$ (8 ml) was stirred at 0° C. for 4 hours. Water and EtOAc were added to the reaction mixture. The organic layer was washed with 1N HCl, aq. NaHCO$_3$ and brine. The organic layer was separated, and dried over MgSO$_4$. The solvent was removed in vacuo. The residue was purified by silica gel column chromatography eluted with a mixture of n-hexane and EtOAc. The fractions were concentrated in vacuo to obtain 5-(1-isopropyl-6-oxo-1,6-dihydro-3-pyridazinyl)-6-phenyl-2-pyrazinyl trifluoromethanesulfonate (174.3 mg) as white powder.

$^1$H NMR (DMSO-d$_6$, δ): 0.76 (6H, d, J=6.6 Hz), 4.91 (1H, 7-plet, J=6.6 Hz), 7.09 (1H, d, J=9.6 Hz), 7.3-7.6 (5H, m), 7.94 (1H, d, J=9.6 Hz), 9.09(1H, s)

Mass (ESI): 441 (M+H)$^+$, 463 (M+Na)$^+$

EXAMPLE 40

A mixture of 5-(1-isopropyl-6-oxo-1,6-dihydro-3-pyridazinyl)-6-phenyl-2-pyrazinyl trifluoromethanesulfonate (1.0 g), MeOH (5.98 ml), palladium acetate (102 mg) and 1,3-bis(diphenylphosphino)propane (187 mg) in DMF (10 ml) was stirred with CO gas bubbling at 20° C. for 30 minutes. Then the reaction mixture was stirred under CO gas at 60° C. for 6 hours. Water and EtOAc were added to the reaction mixture. The organic layer was washed with 1N HCl, aq. NaHCO$_3$ and brine. The organic layer was separated, and dried over MgSO$_4$. The solvent was removed in vacuo. The residue was purified by silica gel column chromatography eluted with a mixture of n-hexane and EtOAc. The fractions were concentrated in vacuo to obtain methyl 5-(1-isopropyl-6-oxo-1,6-dihydro-3-pyridazinyl)-6-phenyl-2-pyrazinecarboxylate (68 mg) as white powder.

$^1$H NMR (DMSO-d$_6$, δ): 0.74 (6H, d, J=6.6 Hz), 3.97 (3H, s), 4.8-5.1 (1H, m), 7.08 (1H, d, J=9.6 Hz), 7.3-7.6 (5H, m), 8.02 (1H, d, J=9.6 Hz), 9.23 (1H, s)

Mass (ESI): 351 (M+H)$^+$, 373 (M+Na)$^+$

EXAMPLE 41

A solution of N'-[3-cyano-6-(4-fluorophenyl)-5-(1-isopropyl-6-oxo-1,6-dihydro-3-pyridazinyl)-2-pyrazinyl]-N,N-dimethylimidoformamide (100 mg) in 4N HCl in dioxane (2 ml) and water (2 ml) was stirred at 25° C. for 15 hours. Water, aq. NaHCO$_3$ and EtOAc were added to the reaction mixture. The organic layer was separated, and dried over MgSO$_4$. The solvent was removed in vacuo. The residue was purified by silica gel column chromatography eluted with a mixture of n-hexane and EtOAc. The fractions were concentrated in vacuo to obtain 3-amino-5-(4-fluorophenyl)-6-(1-isopropyl-6-oxo-1,6-dihydro-3-pyridazinyl)-2-pyrazinecarbonitrile (60 g) as white powder.

$^1$H NMR (DMSO-d$_6$, δ): 0.76 (6H, d, J=6.6 Hz), 4.91 (1H, 7-plet, J=6.6 Hz), 6.99 (1H, d, J=9.6 Hz), 7.0-7.5 (4H, m), 7.7-7.9 (2H, m)

Mass (ESI): 351 (M+H)$^+$, 373 (M+Na)$^+$

EXAMPLE 42

A solution of 3-amino-5-(4-fluorophenyl)-6-(1-isopropyl-6-oxo-1,6-dihydro-3-pyridazinyl)-2-pyrazinecarbonitrile (30 mg) in 28% hydrogen bromide solution of AcOH (2 ml) was stirred at 25° C. for 3 hours. Water, aq. NaHCO$_3$ and EtOAc were added to the reaction mixture. The organic layer was separated, and dried over MgSO$_4$. The solvent was removed in vacuo. The residue was purified by silica gel column chromatography eluted with a mixture of CHCl$_3$ and MeOH. The fractions were concentrated in vacuo to obtain 3-amino-5-(4-fluorophenyl)-6-(1-isopropyl-6-oxo-1,6-dihydro-3-pyridazinyl)-2-pyrazinecarboxamide (30 g) as white powder.

$^1$H NMR (DMSO-d$_6$, δ): 0.90 (6H, d, J=6.6 Hz), 5.11 (1H, 7-plet, J=6.6 Hz), 5.55 (1H, br), 6.98 (1H, d, J=9.6 Hz), 7.0-7.5 (6H, m), 7.5-7.65 (1H, br), 7.69 (1H, d, J=9.6 Hz)

Mass (ESI): 391 (M+Na)$^+$

EXAMPLE 43

3-Amino-5-(3-fluorophenyl)-6-(1-isopropyl-6-oxo-1,6-dihydro-3-pyridazinyl)-2-pyrazinecarbonitrile The title compound was obtained in a similar manner to that of Example 41.

$^1$H NMR (CDCl$_3$, δ): 0.84 (6H, d, J=6.6 Hz), 5.09 (1H, 7-plet, J=6.6 Hz), 5.49 (2H, br), 7.00 (1H, d, J=9.6 Hz), 7.0-7.5 (4H, m), 7.81 (1H, d, J=9.6 Hz)

Mass (ESI): 373 (M+Na)$^+$

EXAMPLE 44

3-Amino-5-(3-fluorophenyl)-6-(1-isopropyl-6-oxo-1,6-dihydro-3-pyridazinyl)-2-pyrazinecarboxamide The title compound was obtained in a similar manner to that of Example 42.

$^1$H NMR (DMSO-d$_6$, δ): 0.88 (6H, d, J=6.6 Hz), 5.11 (1H, 7-plet, J=6.6 Hz), 5.55 (1H, br), 6.99 (1H, d, J=9.6 Hz), 7.0-7.5 (6H, m), 7.60 (1H, br), 7.72 (1H, d, J=9.6 Hz)

Mass (ESI): 391 (M+Na)$^+$

EXAMPLE 45

A mixture of 1-(1-isopropyl-6-oxo-1,6-dihydro-3-pyridazinyl)-2-phenyl-1,2-ethanedione (300 mg), aminoacetamidine dihydrobromide (259 mg) and sodium methoxide (238 mg) in MeOH (3 ml) was stirred for 1.5 hours. Water and EtOAc were added to the reaction mixture. The organic layer was separated, and dried over MgSO$_4$. The solvent was removed in vacuo. The residue was purified by silica gel column chromatography eluted with a mixture of n-hexane and EtOAc. The fractions were concentrated in vacuo to obtain 6-(6-amino-3-phenyl-2-pyrazinyl)-2-isopropyl-3 (2H)-pyridazinone (25.6 mg) as white powder.

$^1$H NMR (DMSO-d$_6$, δ): 0.77 (6H, d, J=6.6 Hz), 4.91 (1H, 7-plet, J=6.6 Hz), 6.74 (2H, br), 6.98 (1H, d, J=9.6 Hz), 7.1-7.5 (5H, m), 7.76 (1H, d, J=9.6 Hz), 8.01 (1H, s)

Mass (ESI): 308 (M+H)$^+$, 330 (M+Na)$^+$

EXAMPLE 46

A solution of 6-(1-isopropyl-6-oxo-1,6-dihydro-3-pyridazinyl)-3-[(4-methoxybenzyl)amino]-5-phenyl-2-pyrazinecarbonitrile (3.88 g) in a mixture of 5N aq. NaOH (20 ml) and EtOH (40 ml) was heated under reflux for 50 hours. After cooling, EtOH was removed under reduced pressure and the residue was adjusted to pH 4 with 1N HCl. The mixture was extracted with CHCl$_3$, dried over MgSO$_4$ and concentrated under reduced pressure to give a solid. The solid was triturated with acetone under reflux for 30 minutes and collected by filtration to give 6-(1-isopropyl-6-oxo-1,6-dihydro-3-pyridazinyl)-3-[(4-methoxybenzyl)amino]-5-phenyl-2-pyrazinecarboxylic acid as a solid (3.15 g).

m.p.: 216.5-217° C. (acetone suspension)

IR (KBr): 3327, 1720, 1643, 1570, 1512 cm$^{-1}$

Mass (ESI, Neg): 470 (M–H)$^-$ $^1$H NMR (CDCl$_3$, δ): 0.87 (6H, d, J=6.60 Hz), 3.81 (3H, s), 4.77 (2H, d, J=5.72 Hz), 5.10 (1H, 7-plet, J=6.60 Hz), 6.89 (2H, d, J=8.57 Hz), 6.98 (1H, d, J=9.60 Hz), 7.28 (2H, d, J=8.57 Hz), 7.30-7.66 (5H, m), 7.63 (1H, d, J=9.60 Hz), 8.42 (1H, t, J=5.72 Hz), 10-11 (1H, br-peak)

EXAMPLE 47

A mixture of 5-(1-isopropyl-6-oxo-1,6-dihydro-3-pyridazinyl)-6-phenyl-2,3-pyrazinedicarbonitrile (51.51 g) and (4-methoxybenzyl)amine (19.7 ml) in DMA (155 ml) was heated at 80-85° C. for 90 hours. After addition of 0.5N aq. NaOH, a precipitate was collected by filtration, dissolved in EtOAc, washed with 0.1N aq. NaOH and water, dried over MgSO$_4$ and concentrated under reduced pressure to give a residue. The residue was purified by column chromatography on silica gel eluting with a mixture of n-hexane and EtOAc (70:30 v/v) to give a mixture of 6-(1-isopropyl-6-oxo-1,6-dihydro-3-pyridazinyl)-3-[(4-methoxybenzyl)amino]-5-phenyl-2-pyrazinecarbonitrile and 5-(1-isopropyl-6-oxo-1,6-dihydro-3-pyridazinyl)-3-[(4-methoxybenzyl)amino]-6-phenyl-2-pyrazinecarbonitrile as an amorphous solid (37.53 g). The solid was crystallized from EtOH to give 6-(1-isopropyl-6-oxo-1,6-dihydro-3-pyridazinyl)-3-[(4-methoxybenzyl)amino]-5-phenyl-2-pyrazinecarbonitrile.

6-(1-isopropyl-6-oxo-1,6-dihydro-3-pyridazinyl)-3-[(4-methoxybenzyl)amino]-5-phenyl-2-pyrazinecarbonitrile m.p.: 89-93° C.

IR (KBr): 2220, 1655, 1562, 1510 cm$^{-1}$

Mass (ESI): 927 (2M+Na)$^+$, 475 (M+Na)$^+$ $^1$H NMR (CDCl$_3$, δ): 0.82 (6H, d, J=6.60 Hz), 3.82 (3H, s), 4.72 (2H, d, J=5.42 Hz), 5.06 (1H, 7-plet, J=6.60 Hz), 5.70 (1H, t, J=5.42 Hz), 6.89-7.00 (3H, m), 7.26-7.43 (7H, m), 7.76 (1H, d, J=9.70 Hz)

5-(1-isopropyl-6-oxo-1,6-dihydro-3-pyridazinyl)-3-[(4-methoxybenzyl)amino]-6-phenyl-2-pyrazinecarbonitrile $^1$H NMR (CDCl$_3$, δ): 4.69 (2H, d, J=5.02 Hz)

EXAMPLE 48

A solution of a mixture (1:1) of 6-(1-isopropyl-6-oxo-1,6-dihydro-3-pyridazinyl)-3-[(4-methoxybenzyl)amino]-5-phenyl-2-pyrazinecarbonitrile and 5-(1-isopropyl-6-oxo-1,6-dihydro-3-pyridazinyl)-3-[(4-methoxybenzyl)amino]-6-phenyl-2-pyrazinecarbonitrile (9.34 g) in a mixture of 5N aq. NaOH (38 ml) and EtOH (38 ml) was heated under reflux for 5 hours. After cooling, EtOH was removed under reduced pressure and the residue was adjusted to pH 4 with 1N HCl to give a solid. The solid was collected by filtration, washed with water and dried under reduced pressure to give a mixture of 6-(1-isopropyl-6-oxo-1,6-dihydro-3-pyridazinyl)-3-[(4-methoxybenzyl)amino]-5-phenyl-2-pyrazinecarboxylic acid and 5-(1-isopropyl-6-oxo-1,6-dihydro-3-pyridazinyl)-3-[(4-methoxybenzyl)amino]-6-phenyl-2-pyrazinecarboxylic acid as a solid (9.36 g). 6-(1-isopropyl-6-oxo-1,6-dihydro-3-pyridazinyl)-3-[(4-methoxybenzyl)amino]-5-phenyl-2-pyrazinecarboxylic acid m.p.: 216.5-217° C. (acetone suspension)

IR (KBr): 3327, 1720, 1643, 1570, 1512 cm$^{-1}$

Mass (ESI, Neg): 470 (M–H)$^-$ $^1$H NMR (CDCl$_3$, δ): 0.87 (6H, d, J=6.60 Hz), 3.81 (3H, s), 4.77 (2H, d, J=5.72 Hz), 5.10 (1H, 7-plet, J=6.60 Hz), 6.89 (2H, d, J=8.57 Hz), 6.98 (1H, d, J=9.60 Hz), 7.28 (2H, d, J=8.57 Hz), 7.30-7.66 (5H, m), 7.63 (1H, d, J=9.60 Hz), 8.42 (1H, t, J=5.72 Hz), 10-11 (1H, br-peak)

5-(1-isopropyl-6-oxo-1,6-dihydro-3-pyridazinyl)-3-[(4-methoxybenzyl)amino]-6-phenyl-2-pyrazinecarboxylic acid $^1$H NMR (CDCl$_3$, δ): 0.74 (6H, d, J=6.60 Hz), 4.59 (2H, d, J=5.12 Hz)

EXAMPLE 49

A suspension of a mixture of 6-(1-isopropyl-6-oxo-1,6-dihydro-3-pyridazinyl)-3-[(4-methoxybenzyl)amino]-5-phenyl-2-pyrazinecarboxylic acid and 5-(1-isopropyl-6-oxo-1,6-dihydro-3-pyridazinyl)-3-[(4-methoxybenzyl)amino]-6-phenyl-2-pyrazinecarboxylic acid (9.34 g) in o-dichlorobenzene (37 ml) was heated at 175-180° C. for 5 hours. After cooling, the reaction mixture was purified by column chromatography on silica gel. By eluting with a mixture of n-hexane and EtOAc (50:50 v/v) was obtained 2-isopropyl-6-{6-[(4-methoxybenzyl)amino]-3-phenyl-2-pyrazinyl}-3(2H)-pyridazinone as a solid (4.41 g) and by eluting with a mixture of n-hexane and EtOAc (40:60 v/v) was obtained 2-isopropyl-6-{5-[(4-methoxybenzyl)amino]-3-phenyl-2-pyrazinyl}-3(2H)-pyridazinone as a solid (2.38 g).

2-isopropyl-6-{5-[(4-methoxybenzyl)amino]-3-phenyl-2-pyrazinyl}-3(2H)-pyridazinone m.p.: 138-140° C.

IR (KBr): 3294, 1651, 1574, 1562, 1514 cm$^{-1}$

Mass (ESI): 877 (2M+Na)$^+$, 450 (M+Na)$^+$, 428(M+H)$^+$ $^1$H NMR (CDCl$_3$, δ): 0.86 (6H, d, J=6.60 Hz), 3.81 (3H, s), 4.59 (2H, d, J=5.24 Hz), 5.07 (1H, 7-plet, J=6.60 Hz), 5.33 (1H, brs), 6.87-6.95 (3H, m), 7.26-7.41 (7H, m), 7.71 (1H, d, J=9.54 Hz), 7.88 (1H, s)

2-isopropyl-6-{6-[(4-methoxybenzyl)amino]-3-phenyl-2-pyrazinyl}-3(2H)-pyridazinone m.p.: 173-174° C.

IR (KBr): 3330, 1653, 1587, 1514 cm$^{-1}$

Mass (ESI): 877 (2M+Na)$^+$, 450 (M+Na)$^+$, 428 (M+H)$^+$ $^1$H NMR (CDCl$_3$, δ): 0.87 (6H, d, J=6.62 Hz), 3.82 (3H, s), 4.58 (2H, s), 5.08 (1H, 7-plet, J=6.62 Hz), 5.18 (1H, brs), 6.87-6.97 (3H, m), 7.21-7.35 (5H, m), 7.73 (1H, d, J=9.58 Hz), 8.02 (1H, s)

EXAMPLE 50

A suspension of 2-isopropyl-6-{6-[(4-methoxybenzyl)amino]-3-phenyl-2-pyrazinyl}-3(2H)-pyridazinone (2.01 g) in a mixture of toluene (1 ml) and conc. HCl (6 ml) was refluxed for 4 hours. After cooling, an organic layer was removed and an aqueous layer was adjusted to pH 8 with 8N aq. NaOH to yield a precipitate. The precipitate was collected by filtration and dried under reduced pressure and purified by column chromatography on silica gel eluting with a mixture of n-hexane and EtOAc (30:70 v/v) to give 6-(6-amino-3-phenyl-2-pyrazinyl)-2-isopropyl-3(2H)-pyridazinone as a solid (680 mg).

m.p.: 214-217° C. (acetone)
IR (KBr): 3423, 3327, 3217, 1645, 1624, 1577, 1566, 1531 cm$^{-1}$
Mass (ESI): 330 (M+Na)$^+$, 308 (M+H)$^+$
$^1$H NMR (CDCl$_3$, δ): 0.88 (6H, d, J=6.60 Hz), 4.85 (2H, brs), 5.09 (1H, 7-plet, J=6.60 Hz), 6.95 (1H, d, J=9.60 Hz), 7.23-7.35 (5H, m), 7.71 (1H, d, J=9.60 Hz), 8.11 (1H, s)

EXAMPLE 51

6-(1-Isopropyl-6-oxo-1,6-dihydro-3-pyridazinyl)-3-[(4-methoxybenzyl)amino]-5-phenyl-2-pyrazinecarbonitrile (14.61 g) was added to a suspension of NaH (60% in oil suspension) (1.36 g) in DMA (36.5 ml) and the mixture was stirred at 20-25° C. for an hour. After addition of 1-(chloromethyl)-4-methoxybenzene (4.82 ml), the mixture was stirred at the same temperature for 20 hours. To the reaction mixture was added water (183 ml) and a precipitate was collected by filtration. The precipitate was purified by column chromatography on silica gel (EtOAc only) to give a solid. The solid was crystallized from a mixture of n-hexane and CHCl$_3$ to give 3-[bis(4-methoxybenzyl)amino]-6-(1-isopropyl-6-oxo-1,6-dihydro-3-pyridazinyl)-5-phenyl-2-pyrazinecarbonitrile (16.58 g).

m.p.: 207-209° C. (CHCl$_3$-n-hexane)
IR (KBr): 2222, 1657, 1545, 1514 cm$^{-1}$
Mass (ESI): 595 (M+Na)$^+$, 573 (M+H)$^+$
$^1$H NMR (CDCl$_3$, δ): 0.83 (6H, d, J=6.60 Hz), 3.81 (6H, s), 4.97 (4H, s), 5.04 (1H, 7-plet, J=6.60 Hz), 6.86-7.02 (5H, m), 7.17-7.22 (4H, m), 7.33-7.46 (5H, m), 7.92 (1H, d, J=9.58 Hz)

EXAMPLE 52

A suspension of 3-[bis(4-methoxybenzyl)amino]-6-(1-isopropyl-6-oxo-1,6-dihydro-3-pyridazinyl)-5-phenyl-2-pyrazinecarbonitrile (3.00 g) in a mixture of 2N aq. NaOH (30 ml) and dioxane (21 ml) was refluxed for 36 hours. After cooling, the mixture was extracted with EtOAc, dried over MgSO$_4$, concentrated under reduced pressure and purified by column chromatography on silica gel eluting with a mixture of n-hexane and EtOAc (20:80 v/v) to give a solid. The solid was crystallized from a mixture of n-hexane and acetone to give 3-[bis(4-methoxybenzyl)amino]-6-(1-isopropyl-6-oxo-1,6-dihydro-3-pyridazinyl)-5-phenyl-2-pyrazinecarboxamide (2.56 g).

m.p.: 120-122.5° C. (acetone-n-hexane)
IR (KBr): 1651, 1585, 1539, 1510 cm$^{-1}$
Mass (ESI): 613 (M+Na)$^+$, 591 (M+H)$^+$
$^1$H NMR (CDCl$_3$, δ): 0.87 (6H, d, J=6.62 Hz), 3.78 (6H, s), 4.76 (4H, s), 5.09 (1H, 7-plet), 5.49 (1H, brs), 6.83 (4H, d, J=8.60 Hz), 6.99 (1H, d, J=9.60 Hz), 7.13 (4H, d, J=8.60 Hz), 7.26 (1H, brs), 7.31-7.34 (3H, m), 7.47-7.50 (2H, m), 7.92 (1H, d, J=9.60 Hz)

EXAMPLE 53

N-bromosuccinimide (875 mg) was added to a solution of 6-(5-amino-3-phenyl-2-pyrazinyl)-2-isopropyl-3(2H)-pyridazinone (1.51 g) in DMF (15 ml). The mixture was stirred at 50-55° C. for one hour and poured into water (150 ml). The precipitate was collected by filtration, dissolved in CHCl$_3$, dried over MgSO$_4$ and concentrated under reduced pressure to give a solid. The solid was suspended in acetone and collected by filtration to give 6-(5-amino-6-bromo-3-phenyl-2-pyrazinyl)-2-isopropyl-3(2H)-pyridazinone as a solid (1.26 g).

m.p.: 204-206° C. (acetone)
IR (KBr): 3465, 3267, 3145, 1657, 1614, 1587, 1518 cm$^{-1}$
Mass (ESI): 797 and 795 (2M+Na)$^+$, 408 and 410 (M+Na)$^+$, 386 and 388 (M+H)$^+$
$^1$H NMR (CDCl$_3$, δ): 0.82 (6H, d, J=6.62 Hz), 5.06 (1H, 7-plet, J=6.62 Hz), 5.32 (2H, brs), 6.94 (1H, d, J=9.58 Hz), 7.30-7.40 (5H, m), 7.76 (1H, d, J=9.58 Hz)

EXAMPLE 54

A mixture of 6-(5-amino-6-bromo-3-phenyl-2-pyrazinyl)-2-isopropyl-3(2H)-pyridazinone (11.35 g) and sodium thiomethoxide (4.12 g) in 1,3-dimethyl-2-imidazolidinone (17 ml) was heated at 100-105° C. for one hour. The mixture was poured into water (170 ml). The precipitate was collected by filtration, dissolved in CHCl$_3$, dried over MgSO$_4$, concentrated under reduced pressure to give a residue. The residue was purified by column chromatography on silica gel eluting with a mixture of n-hexane and EtOAc (50:50 v/v) to give 6-[5-amino-6-(methylthio)-3-phenyl-2-pyrazinyl]-2-isopropyl-3(2H)-pyridazinone as a solid (4.32 g).

6-[5-amino-6-(methylthio)-3-phenyl-2-pyrazinyl]-2-isopropyl-3(2H)-pyridazinone m.p.: 211-214° C. (acetone-hexane)
IR (KBr): 3464, 3323, 1660, 1612, 1585 cm$^{-1}$
Mass (ESI): 729 (2M+Na)$^+$, 376 (M+Na)$^+$, 354 (M+H)$^+$
$^1$H NMR (CDCl$_3$, δ): 0.84 (6H, d, J=6.60 Hz), 2.70 (3H, s), 5.00 (2H, brs), 5.08 (1H, 7-plet, J=6.60 Hz), 6.94 (1H, d, J=9.58 Hz), 7.26-7.37 (5H, m), 7.79 (1H, d, J=9.58 Hz)

EXAMPLE 55

Under ice-cooling, m-chloroperbenzoic acid (70-75% purity) (2.09 g) was added to a mixture of 6-[5-amino-6-(methylthio)-3-phenyl-2-pyrazinyl]-2-isopropyl-3(2H)-pyridazinone (3.00 g) in CH$_2$Cl$_2$ (30 ml) and stirred at the same temperature for one hour. The mixture was washed with saturated aq. sodium thiosulfate, saturated aq. NaHCO$_3$ and brine, dried over MgSO$_4$ and concentrated under reduced pressure to give a residue. The residue was purified by column chromatography on silica gel. By eluting with a mixture of n-hexane and EtOAc (30:70 v/v) was obtained 6-[5-amino-6-(methylsulfonyl)-3-phenyl-2-pyrazinyl]-2-isopropyl-3(2H)-pyridazinone as a solid (0.69 g) and by eluting with a mixture of n-hexane and EtOAc (20:80 v/v) was obtained 6-[5-amino-6-(methylsulfinyl)-3-phenyl-2-pyrazinyl]-2-isopropyl-3(2H)-pyridazinone as a solid (2.32 g).

6-[5-amino-6-(methylsulfinyl)-3-phenyl-2-pyrazinyl]-2-isopropyl-3(2H)-pyridazinone m.p.: 225-227° C. (CHCl$_3$-n-hexane)
IR (KBr): 3375, 3282, 3184, 1666, 1653, 1618, 1583, 1520 cm$^{-1}$
Mass (ESI): 392 (M+Na)$^+$, 370 (M+H)$^+$ ¹H NMR (CDCl₃, δ): 0.79 (3H, d, J=6.60 Hz), 0.86 (3H, d, J=6.60 Hz), 3.03 (3H, s), 5.06 (1H, 7-plet, J=6.60 Hz), 6.39 (2H, brs), 6.94 (1H, d, J=9.60 Hz), 7.33-7.41 (5H, m), 7.68 (1H, d, J=9.60 Hz)

6-[5-amino-6-(methylsulfonyl)-3-phenyl-2-pyrazinyl]-2-isopropyl-3(2H)-pyridazinone
  m.p.: 249-251° C. (CHCl₃-n-hexane)
  IR (KBr): 3477, 3373, 1666, 1591, 1527 cm–1
  Mass (ESI): 408 (M+Na)⁺, 386 (M+H)⁺
  ¹H NMR (CDCl₃, δ): 0.82 (6H, d, J=6.60 Hz), 3.34 (3H, s), 5.07 (1H, 7-plet, J=6.60 Hz), 6.20 (2H, brs), 6.98 (1H, d, J=9.58 Hz), 7.39 (5H, m), 7.76 (1H, d, J=9.58 Hz)

EXAMPLE 56

Under ice-cooling, m-chloroperbenzoic acid (70-75% purity) (530 mg) was added to a mixture of 6-[5-amino-6-(methylsulfinyl)-3-phenyl-2-pyrazinyl]-2-isopropyl-3(2H)-pyridazinone (750 mg) in CH₂Cl₂ (7.5 ml). The mixture was stirred at 25-30° C. for 5 hours, washed with saturated aq. sodium thiosulfate, saturated aq. NaHCO₃ and brine, dried over MgSO₄ and concentrated under reduced pressure to give a residue. The residue was purified by column chromatography on silica gel eluting with a mixture of n-hexane and EtOAc (30:70 v/v) to give 6-[5-amino-6-(methylsulfonyl)-3-phenyl-2-pyrazinyl]-2-isopropyl-3(2H)-pyridazinone as a solid (524 mg).
  m.p.: 249-251° C. (CHCl₃-hexane)
  IR (KBr): 3477, 3373, 1666, 1591, 1527 cm⁻¹
  Mass (ESI): 408 (M+Na)⁺, 386 (M+H)⁺
  ¹H NMR (CDCl₃, δ): 0.82 (6H, d, J=6.60 Hz), 3.34 (3H, s), 5.07 (1H, 7-plet, J=6.60 Hz), 6.20 (2H, brs), 6.98 (1H, d, J=9.58 Hz), 7.39 (5H, m), 7.76 (1H, d, J=9.58 Hz)

EXAMPLE 57

A solution of 6-(1-ethyl-6-oxo-1,6-dihydro-3-pyridazinyl)-3-[(4-methoxybenzyl)amino]-5-phenyl-2-pyrazinecarbonitrile (1.00 g) in a mixture of 5N aq. NaOH (4 ml) and EtOH (4 ml) was refluxed for 5 hours. At 40-50° C., the mixture was adjusted to pH 4 with 1N HCl and stirred for one hour to give a precipitate. The precipitate was collected by filtration and dried under reduced pressure to give 6-(1-ethyl-6-oxo-1,6-dihydro-3-pyridazinyl)-3-[(4-methoxybenzyl)amino]-5-phenyl-2-pyrazinecarboxylic acid (1.03 g).
  m.p.: >250° C.
  IR (KBr): 1655, 1637, 1568, 1514 cm⁻¹
  Mass (ESI): 480 (M+Na)⁺, 458 (M+H)⁺
  ¹H NMR (DMSO-d₆, δ): 0.81 (3H, t, J=7.16 Hz), 3.72-3.79 (5H, m), 4.63 (2H, d, J=5.52 Hz), 6.89-6.94 (3H, m), 7.30-7.40 (7H, m), 7.77 (1H, d, J=9.58 Hz), 9.61 (1H, brs)

EXAMPLE 58

A mixture of 6-(1-ethyl-6-oxo-1,6-dihydro-3-pyridazinyl)-3-[(4-methoxybenzyl)amino]-5-phenyl-2-pyrazinecarboxylic acid (1.02 g) in 1,2-dichlorobenzene (20 ml) was refluxed for 3 hours. The mixture was purified by column chromatography on silica gel eluting with a mixture of n-hexane and EtOAc (40:60 v/v) to give 2-ethyl-6-{5-[(4-methoxybenzyl)amino]-3-phenyl-2-pyrazinyl}-3(2H)-pyridazinone as a solid (783 mg).
  m.p.: 148-150° C. (acetone-n-hexane)
  IR (KBr): 3265, 1645, 1570, 1514 cm⁻¹
  Mass (ESI): 849 (2M+Na)⁺, 436 (M+Na)⁺, 414 (M+H)⁺
  ¹H NMR (CDCl₃, δ): 1.04 (3H, t, J=7.17 Hz), 3.81 (3H, s), 3.98 (2H, q, J=7.17 Hz), 4.58 (2H, d, J=5.32 Hz), 5.34 (1H, t, J=5.32 Hz), 6.81-6.92 (3H, m), 7.26-7.48 (8H, m), 7.90 (1H, s)

EXAMPLE 59

A suspension of 2-ethyl-6-{5-[(4-methoxybenzyl)amino]-3-phenyl-2-pyrazinyl}-3(2H)-pyridazinone (500 mg) in a mixture of conc. HCl (1.5 ml) and toluene (0.5 ml) was refluxed for 4 hours. After removal of an organic layer, an aqueous layer was adjusted to pH 4 with 6N aq. NaOH under ice-cooling. The precipitate was purified by column chromatography on silica gel eluting with a mixture of n-hexane and EtOAc (20:80 v/v) to give 6-(5-amino-3-phenyl-2-pyrazinyl)-2-ethyl-3(2H)-pyridazinone (213 mg).
  m.p.: 227-229° C. (EtOAc)
  IR (KBr): 3392, 3323, 1650, 1587, 1570, 1533 cm⁻¹
  Mass (ESI): 609 (2M+Na)⁺, 316 (M+Na)⁺, 294 (M+H)⁺
  ¹H NMR (CDCl₃, δ): 1.03 (3H, t, J=7.17 Hz), 3.97 (2H, q, J=7.17 Hz), 4.98(2H, brs), 6.86 (1H, d, J=9.60 Hz), 7.33-7.41 (5H, m), 7.49 (1H, d, J=9.60 Hz), 8.02 (1H, s)
  ¹H NMR (DMSO-d₆, δ): 0.78 (3H, t, J=7.20 Hz), 3.73 (2H, q, J=7.20 Hz), 6.89 (2H, brs), 6.92 (1H, d, J=9.60 Hz), 7.34 (5H, s), 7.69 (1H, d, J=9.60 Hz), 7.93 (1H, s)

EXAMPLE 60

6-(5-amino-6-bromo-3-phenyl-2-pyrazinyl)-2-methyl-3(2H)-pyridazinone
The title compound was obtained in a similar manner to that of Example 53.
  m.p.: 220-222° C.
  IR (KBr): 3417, 3396, 3292, 3194, 1649, 1630, 1579, 1543 cm⁻¹
  Mass (ESI): 382 and 380 (M+Na)⁺
  ¹H NMR (DMSO-d₆, δ): 3.39 (3H, s), 6.87 (1H, d, J=9.60 Hz), 7.19 (2H, brs), 7.37 (5H, s), 7.44 (1H, d, J=9.60 Hz)

EXAMPLE 61

6-[5-amino-6-(methylthio)-3-phenyl-2-pyrazinyl]-2-methyl-3(2H)-pyridazinone
The title compound was obtained in a similar manner to that of Example 54.
  m.p.: 204-205.5° C.
  IR (KBr): 3305, 3188, 1653, 1577, 1523, 1506 cm⁻¹
  Mass (ESI): 673 (2M+Na)⁺, 348 (M+Na)⁺, 326 (M+H)⁺
  ¹H NMR (DMSO-d₆, δ): 2.59 (3H, s), 3.31 (3H, s), 6.73 (2H, brs), 6.93 (1H, d, J=9.58 Hz), 7.34 (5H, s), 7.74 (1H, d, J=9.58 Hz)

EXAMPLE 62

6-[5-amino-6-(methylsulfinyl)-3-phenyl-2-pyrazinyl]-2-methyl-3(2H)-pyridazinone and 6-[5-amino-6-(methylsulfonyl)-3-phenyl-2-pyrazinyl]-2-methyl-3(2H)-pyridazinone
The title compounds were obtained in a similar manner to that of Example 55.

6-[5-amino-6-(methylsulfinyl)-3-phenyl-2-pyrazinyl]-2-methyl-3(2H)-pyridazinone
  m.p.: 209-210.5° C.
  IR (KBr): 3361, 3257, 3180, 3149, 1657, 1620, 1583, 1522 cm⁻¹
  Mass (ESI): 364(M+Na)⁺

¹H NMR (CDCl₃, δ): 3.03 (3H, s), 3.53 (3H, s), 6.45 (2H, brs), 6.85 (1H, d, J=9.65 Hz), 7.37-7.44 (6H, m)

6-[5-amino-6-(methylsulfonyl)-3-phenyl-2-pyrazinyl]-2-methyl-3(2H)-pyridazinone
m.p.: 231-233° C.
IR (KBr): 3427, 3278, 1672, 1666, 1612, 1589 cm⁻¹
Mass (ESI): 380 (M+Na)⁺
¹H NMR (CDCl₃, δ): 3.33 (3H, s), 3.48 (3H, s), 6.22 (2H, brs), 6.91 (1H, d, J=9.60 Hz), 7.44-7.48 (5H, m), 7.58 (1H, d, J=9.60 Hz)

EXAMPLE 63

6-[5-amino-6-(methylsulfonyl)-3-phenyl-2-pyrazinyl]-2-methyl-3(2H)-pyridazinone
The title compound was obtained in a similar manner to that of Example 56.
m.p.: 231-233° C.
IR (KBr): 3427, 3278, 1672, 1666, 1612, 1589 cm⁻¹
Mass (ESI): 380 (M+Na)⁺
¹H NMR (CDCl₃, δ): 3.33 (3H, s), 3.48 (3H, s), 6.22 (2H, brs), 6.91 (1H, d, J=9.60 Hz), 7.44-7.48 (5H, m), 7.58 (1H, d, J=9.60 Hz)

EXAMPLE 64

A solution of 6-[5-amino-6-(methylsulfonyl)-3-phenyl-2-pyrazinyl]-2-isopropyl-3(2H)-pyridazinone (200 mg) in a mixture of 1N aq. NaOH (1 ml) and dioxane (2 ml) was refluxed for 6 hours. After cooling, the mixture was adjusted to pH 4 with 1N HCl to give a precipitate. The precipitate was collected by filtration and crystallized from DMSO and water to give 6-(5-amino-6-oxo-3-phenyl-1,6-dihydro-2-pyrazinyl)-2-isopropyl-3(2H)-pyridazinone (123 mg).
m.p.: >250° C. (DMSO-H₂O)
IR (KBr): 3431, 3315, 1664, 1645, 1608, 1585, 1522 cm⁻¹
Mass (ESI): 346 (M+Na)⁺, 324 (M+H)⁺
¹H NMR (DMSO-d₆, δ): 1.11 (6H, d, J=6.60 Hz), 5.02 (1H, 7-plet, J=6.60 Hz), 6.75 (1H, d, J=9.58 Hz), 7.03-7.35 (8H, m), 11.90 (1H, s)

EXAMPLE 65

To a suspension of 6-(5-amino-3-phenyl-2-pyrazinyl)-2-isopropyl-3(2H)-pyridazinone (1.01 g) was added dimethyl sulfide (0.263 ml) and N-chlorosuccinimide (435 mg) under −5° C. The mixture was stirred at −5° C. for 30 minutes and at 20-25° C. for 20 hours. A solution of 28% sodium methoxide in MeOH (1.13 ml) was added to the mixture and the solution was stirred at the same temperature for an hour. After addition of water (10 ml), the organic layer was collected, dried over MgSO₄, concentrated under reduced pressure and purified by column chromatography on silica gel eluting with a mixture of MeOH and EtOAc (1:99 v/v) to give 6-{5-[(dimethyl-lambda~4~-sulfanylidene)amino]-3-phenyl-2-pyrazinyl}-2-isopropyl-3(2H)-pyridazinone as a solid (0.80 g).
m.p.: 190-194° C.
IR (KBr): 1662, 1657, 1589, 1547, 1547, 1502 cm⁻¹
Mass (ESI): 390 (M+Na)⁺, 368 (M+H)⁺
¹H NMR (CDCl₃, δ): 0.85 (6H, d, J=6.70 Hz), 2.81 (6H, s), 5.07 (1H, 7-plet), 6.92 (1H, d, J=9.58 Hz), 7.27-7.42 (5H, m), 7.74 (1H, d), 8.07 (1H, s)

EXAMPLE 66

To a solution of DMSO (0.75 ml) in CH₂Cl₂ (5 ml) was added trifluoromethanesulfonic anhydride (1.5 ml) dropwise at <−75° C. under nitrogen. A suspension of 6-(5-amino-6-bromo-3-phenyl-2-pyrazinyl)-2-isopropyl-3(2H)-pyridazinone (3.00 g) in a mixture of DMSO (5 ml) and CH₂Cl₂ (6 ml) was added and stirred at −65° C. for 2 hours and at −55° C. for one hour. The reaction mixture was quenched with 1N aq. NaOH (20 ml) and stirred at 15° C. for 10 minutes. An organic layer was collected, dried over MgSO₄ and concentrated under reduced pressure to give a solid. The solid was suspended in acetone and collected by filtration to give 6-{6-bromo-5-[(dimethyl-lambda~4~-sulfanylidene)amino]-3-phenyl-2-pyrazinyl}-2-isopropyl-3(2H)-pyridazinone (3.16 g).
m.p.: 220-224° C.
IR (KBr): 1651, 1585, 1537 cm⁻¹
Mass (ESI): 470 and 468 (M+Na)⁺, 448 and 446 (M+H)⁺
¹H NMR (CDCl₃, δ): 0.82 (6H, d, J=6.66 Hz), 2.88 (6H, s), 5.05 (1H, 7-plet, J=6.66 Hz), 6.92 (1H, d, J=9.56 Hz), 9.27-9.38 (5H, m), 7.78 (1H, d, J=9.58 Hz)
¹H NMR (DMSO-d₆, δ): 0.73 (6H, d, J=6.60 Hz), 2.86 (6H, s), 4.88 (1H, 7-plet, J=6.60 Hz), 6.93 (1H, d, J=9.68 Hz), 7.30-7.42 (5H, m), 7.73 (1H, d, J=9.68 Hz)

EXAMPLE 67

To a solution of m-chloroperbenzoic acid (70-75% purity) (1.66 g) in CH₂Cl₂ (40 ml) was added a solution of 6-{6-bromo-5-[(dimethyl-lambda~4~-sulfanylidene)amino]-3-phenyl-2-pyrazinyl}-2-isopropyl-3 (2H)-pyridazinone (2.01 g) in CH₂Cl₂ (20 ml) at −10~-5° C. and the mixture was stirred at the same temperature for one hour. After addition of dimethyl sulfide (0.25 ml), the solution was stirred at the same temperature for 30 minutes. Sat. aq. Na₂CO₃ (50 ml) was then added to the mixture. An organic layer was collected, dried over MgSO₄, concentrated under reduced pressure and purified by column chromatography on silica gel eluting with a mixture of n-hexane and EtOAc (70:30 v/v) to give 6-(6-bromo-5-nitroso-3-phenyl-2-pyrazinyl)-2-isopropyl-3(2H)-pyridazinone as a solid (0.896 g).
m.p.: 164-166° C.
IR (KBr): 1666, 1591, 1514 cm⁻¹
Mass (ESI): 424 and 422 (M+Na)⁺, 402 and 400 (M+H)⁺
¹H NMR (CDCl₃, δ): 0.79 (6H, d, J=6.60 Hz), 5.06 (1H, 7-plet, J=6.60 Hz), 7.05 (1H, d, J=9.66 Hz), 7.37 (5H, s), 8.11 (1H, d, J=9.66 Hz)

EXAMPLE 68

A solution of tert-butyl (2-{[1-(1-isopropyl-6-oxo-1,6-dihydro-3-pyridazinyl)-2-oxo-2-phenylethyl]amino}-2-oxoethyl)carbamate (310 mg) in 10% hydrogen chloride in MeOH (3 ml) was stirred at 20-25° C. for 18 hours and the mixture was concentrated under reduced pressure to give a residue. The residue was dissolved in pyridine (1.5 ml) and heated at 80-85° C. for 10 hours. After evaporation of pyridine, the mixture was dissolved in CHCl₃, washed with 1N HCl, sat. aq. NaHCO₃ and brine, dried over MgSO₄ and concentrated under reduced pressure to give syrup. The syrup was purified by column chromatography on silica gel eluting with a mixture of n-hexane and EtOAc (40:60 v/v) to give 6-(6-hydroxy-3-phenyl-2-pyrazinyl)-2-isopropyl-3 (2H)-pyridazinone as a solid (65 mg).
m.p.: 198-200° C.
IR (KBr): 1664, 1593, 1533 cm⁻¹
Mass (ESI): 639 (2M+Na)⁺, 331 (M+Na)⁺, 309 (M+H)⁺
¹H NMR (CDCl₃, δ): 1.43 (6H, d, J=6.60 Hz), 5.34 (1H, 7-plet, J=6.60 Hz), 6.66 (1H, d, J=9.75 Hz), 6.79 (1H, d, J=9.75 Hz), 7.41 (5H, s), 8.31 (1H, s)

¹H NMR (DMSO-d₆, δ): 0.83 (6H, d, J=6.60 Hz), 4.94 (1H, 7-plet, J=6.60 Hz), 7.00 (1H, d, J=9.63 Hz), 7.23-7.41 (5H, m), 7.72 (1H, d, J=9.63 Hz), 8.25 (1H, s), 12.19 (1H, brs)

EXAMPLE 69

In the presence of copper(I) iodide (25 mg) and dichlorobis(triphenylphosphine)palladium(II) (91 mg), triethylamine (0.397 ml) was dropwise added to a mixture of 6-(5-amino-6-bromo-3-phenyl-2-pyrazinyl)-2-isopropyl-3(2H)-pyridazinone (1.00 g) and ethynyl(trimethyl)silane (0.716 ml) in 1,2-dichloroethane (20 ml) under ice-cooling. The mixture was stirred at same temperature for one hour and at 25-30° C. for 18 hours. After addition of water, an organic layer was collected, washed with sat. aq. sodium chloride, dried over MgSO₄ and concentrated under reduced pressure to give a residue. The residue was purified by column chromatography on silica gel eluting with a mixture of n-hexane and EtOAc (80:20 v/v) to give a solid. The solid was crystallized from a mixture of acetone and n-hexane to give 6-{5-amino-3-phenyl-6-[(trimethylsilyl)ethynyl]-2-pyrazinyl}-2-isopropyl-3(2H)-pyridazinone (431 mg).

m.p.: 213-215° C. (acetone-n-hexane)

IR (KBr): 3464, 3276, 3176, 3147, 2966, 2143, 1662, 1618, 1591 cm⁻¹

Mass (ESI): 426 (M+Na)⁺, 404 (M+H)⁺

¹H NMR (CDCl₃, δ): 0.33 (9H, s), 0.82 (6H, d, J=6.60 Hz), 5.06 (1H, 7-plet, J=6.60 Hz), 5.34 (2H, brs), 6.94 (1H, d, J=9.56 Hz), 7.30-7.38 (5H, m), 7.78 (1H, d, J=9.56 Hz)

EXAMPLE 70

In the presence of copper(I) iodide (5 mg) and dichlorobis(triphenylphosphine)palladium(II) (18 mg), triethylamine (0.0794 ml) was dropwise added to a mixture of 6-(5-amino-6-bromo-3-phenyl-2-pyrazinyl)-2-isopropyl-3(2H)-pyridazinone (200 mg) and ethynylbenzene (0.0626 ml) in 1,2-dichloroethane (2 ml) at 60° C. The mixture was refluxed for 2 hours. The mixture was cooled to give a precipitate. The precipitate was collected by filtration and suspended in MeOH to give 6-[5-amino-3-phenyl-6-(phenylethynyl)-2-pyrazinyl]-2-isopropyl-3(2H)-pyridazinone (104 mg).

m.p.: 239-241° C. (MeOH suspension)

IR (KBr): 3477, 3267, 3126, 2195, 1660, 1624, 1587, 1502 cm⁻¹

Mass (ESI): 837 (2M+Na)⁺, 430 (M+Na)⁺, 408 (M+H)⁺

¹H NMR (DMSO-d₆, δ): 0.74 (6H, d, J=6.60 Hz), 4.89 (1H, 7-plet, J=6.60 Hz), 6.97 (1H, d, J=9.60 Hz), 7.19 (2H, brs), 7.36-7.40 (5H, m), 7.44-7.51 (3H, m), 7.75-7.81 (2H, m), 7.84 (1H, d, J=9.60 Hz)

EXAMPLE 71

In the presence of copper(I) iodide (7.5 mg) and dichlorobis(triphenylphosphine)palladium(II) (27.4 mg), triethylamine (0.1192 ml) was dropwise added to a mixture of 6-(5-amino-6-bromo-3-phenyl-2-pyrazinyl)-2-isopropyl-3(2H)-pyridazinone (300 mg) and ethynyl(trimethyl)silane (85.6 mg) in 1,2-dichloroethane (3 ml) at 60° C. The mixture was refluxed for 2 hours. After addition of water, an organic layer was collected, washed with sat. aq. sodium chloride, dried over MgSO₄ and concentrated under reduced pressure to give a residue. The residue was purified by column chromatography on silica gel eluting with a mixture of n-hexane and EtOAc (60:40 v/v) to give a solid. The solid was crystallized from a mixture of acetone and n-hexane to give 6-{5-amino-6-[3-(methoxymethoxy)-1-propyn-1-yl]-3-phenyl-2-pyrazinyl}-2-isopropyl-3(2H)-pyridazinone (233 mg).

m.p.: 133-135° C.

IR (KBr): 3471, 3275, 3113, 2969, 1662, 1628, 1589, 1506 cm⁻¹

Mass (ESI): 428 (M+Na)⁺, 406 (M+H)⁺

¹H NMR (CDCl₃, δ): 0.82 (6H, d, J=6.60 Hz), 3.45 (3H, s), 4.56 (2H, s), 4.82 (2H, s), 5.06 (1H, 7-plet, J=6.60 Hz), 5.40 (2H, brs), 6.94 (1H, d, J=9.58 Hz), 7.31-7.39 (5H, m), 7.78 (1H, d, J=9.58 Hz)

The following 2 compounds were obtained in a similar manner to that of Example 71.

EXAMPLE 72

6-[5-amino-6-(1-cyclohexen-1-ylethynyl)-3-phenyl-2-pyrazinyl]-2-isopropyl-3(2H)-pyridazinone m.p.: 231-233° C.

IR (KBr): 3471, 3275, 3138, 2181, 1662, 1626, 1591 cm⁻¹

Mass (ESI): 434 (M+Na)⁺, 412 (M+H)⁺

¹H NMR (CDCl₃, δ): 0.82 (6H, d, J=6.60 Hz), 1.63-1.76 (4H, m), 2.17-2.30 (4H, m), 5.06 (1H, 7-plet, J=6.60 Hz), 5.27 (2H, brs), 6.38-6.43 (1H, m), 6.93 (1H, d, J=9.56 Hz), 7.27-7.38 (5H, m), 7.78 (1H, d, J=9.56 Hz)

EXAMPLE 73

6-{5-amino-6-[(1-hydroxycyclohexyl)ethynyl]-3-phenyl-2-pyrazinyl}-2-isopropyl-3(2H)-pyridazinone m.p.: 238-240° C.

IR (KBr): 3471, 3261, 3178, 2220, 1647, 1614, 1579, 1508 cm⁻¹

Mass (ESI): 452 (M+Na)⁺, 430 (M+H)⁺

¹H NMR (CDCl₃, δ): 0.82 (6H, d, J=6.62 Hz), 1.22-2.18 (10H, m), 5.06 (1H, 7-plet, J=6.62 Hz), 5.32 (2H, brs), 6.96 (1H, d, J=9.56 Hz), 7.27-7.38 (5H, m), 7.78 (1H, d, J=9.56 Hz)

¹H NMR (DMSO-d₆, δ): 0.73 (6H, d, J=6.60 Hz), 1.17-1.99 (10H, m), 4.88 (1H, 7-plet, J=6.60 Hz), 5.68 (1H, s), 6.92 (2H, brs), 6.94 (1H, d, J=9.60 Hz), 7.33-7.41 (5H, m), 7.79 (1H, d, J=9.60 Hz)

EXAMPLE 74

In the presence of copper(I) iodide (3.7 mg) and dichlorobis(triphenylphosphine)palladium(II) (13.7 mg), triethylamine (0.0596 ml) was dropwise added to a mixture of 6-(5-amino-6-bromo-3-phenyl-2-pyrazinyl)-2-isopropyl-3(2H)-pyridazinone (150 mg) and 2-ethynylpyridine (0.0431 ml) in 1,2-dichloroethane (1.5 ml) at 30-35° C. The mixture was stirred at the same temperature for 18 hours. Water was added to the reaction mixture to give a solid. The solid was purified by column chromatography on silica gel (EtOAc only) to give a solid. The solid was suspended in acetone to give 6-[5-amino-3-phenyl-6-(2-pyridylethynyl)-2-pyrazinyl]-2-isopropyl-3(2H)-pyridazinone (88 mg).

m.p.: 245.5-247° C.

IR (KBr): 3469, 3261, 3134, 3124, 2208, 1658, 1621, 1585, 1558, 1531, 1504 cm⁻¹

Mass (ESI): 431 (M+Na)⁺

¹H NMR (DMSO-d₆, δ): 0.74 (6H, d, J=6.64 Hz), 4.89 (1H, 7-plet, J=6.64 Hz), 6.97 (1H, d, J=9.57 Hz), 7.26 (2H, brs), 7.35-7.51 (6H, m), 7.85 (1H, d, J=9.57 Hz), 7.87-7.96 (2H, m), 8.64-8.68 (1H, m)

EXAMPLE 75

In the presence of copper(I) iodide (3.7 mg) and dichlorobis(triphenylphosphine)palladium(II) (13.7 mg), triethylamine (0.0596 ml) was dropwise added to a mixture of 6-(5-amino-6-bromo-3-phenyl-2-pyrazinyl)-2-isopropyl-3(2H)-pyridazinone (150 mg) and 5-ethynyl-1-methyl-1H-imidazole (45.4 mg) in THF (1.5 ml) at 50° C. The mixture was refluxed for 2 hours. Water was added to the reaction mixture to give a solid. The solid was purified by column chromatography on silica gel eluting with a mixture of MeOH and EtOAc (2:98 v/v) to give 6-{5-amino-6-[(1-methyl-1H-imidazol-5-yl)ethynyl]-3-phenyl-2-pyrazinyl}-2-isopropyl-3(2H)-pyridazinone as a solid (135 mg).

m.p.: >250° C.

IR (KBr): 3473, 3275, 3141, 3074, 2195, 1658, 1630, 1587, 1518 $cm^{-1}$

Mass (ESI): 845 $(2M+Na)^+$, 434 $(M+Na)^+$, 412 $(M+H)^+$ $^1$H NMR ($CDCl_3$, δ): 0.83 (6H, d, J=6.64 Hz), 3.86 (3H, s), 5.07 (1H, 7-plet, J=6.64 Hz), 5.36 (2H, brs), 6.96 (1H, d, J=9.60 Hz), 7.28-7.41 (5H, m), 7.6 (1H, brs), 7.79 (1H, d, J=9.60 Hz), 7.86 (1H, brs)

$^1$H NMR (DMSO-$d_6$, δ): 0.74 (6H, d, J=6.60 Hz), 3.77 (3H, s), 4.89 (1H, 7-plet, J=6.60 Hz), 6.96 (1H, d, J=9.61 Hz), 7.14 (2H, brs), 7.34-7.42 (5H, m), 7.51 (1H, brs), 7.82 (1H, d, J=9.61 Hz), 7.84 (1H, brs)

EXAMPLE 76

Under ice-cooling, 12N aq. NaOH (0.9 ml) was added dropwise to a solution of 6-{5-amino-3-phenyl-6-[(trimethylsilyl)ethynyl]-2-pyrazinyl}-2-isopropyl-3(2H)-pyridazinone (908 mg) in a mixture of acetonitrile (0.9 ml) and THF (1.8 ml). The mixture was stirred at 25-30° C. for one hour, neutralized with 6N HCl, extracted with $CHCl_3$, dried over $MgSO_4$ and concentrated under reduced pressure to give a syrup. The syrup was purified by column chromatography on silica gel eluting with a mixture of n-hexane and EtOAc (30:70 v/v) to give 6-(5-amino-6-ethynyl-3-phenyl-2-pyrazinyl)-2-isopropyl-3(2H)-pyridazinone as a solid (196 mg).

m.p.: 217° C. (dec.) (acetone-n-hexane)

IR (KBr): 3469, 3297, 3140, 2102, 1657, 1620, 1585 $cm^{-1}$

Mass (ESI): 685 $(2M+Na)^+$, 354 $(M+Na)^+$, 332 $(M+H)^+$ $^1$H NMR ($CDCl_3$, δ): 0.81 (6H, d, J=6.63 Hz), 3.59 (1H, s), 5.06 (1H, 7-plet, J=6.63 Hz), 5.33 (2H, brs), 6.94 (1H, d, J=9.56 Hz), 7.30-7.39 (5H, m), 7.79 (1H, d, J=9.56 Hz)

EXAMPLE 77

In the presence of copper(I) iodide (4.3 mg) and dichlorobis(triphenylphosphine)palladium(II) (15.7 mg), triethylamine (0.0685 ml) was dropwise added to a mixture of 6-(5-amino-6-bromo-3-phenyl-2-pyrazinyl)-2-methyl-3(2H)-pyridazinone (150 mg) and ethynylbenzene (0.0054 ml) in DMF (1.5 ml) at 75-80° C. The mixture was stirred at the same temperature for 2 hours. To the reaction mixture, water was added to give a solid. The solid was purified by column chromatography on silica gel eluting with a mixture of n-hexane and EtOAc (40:60 v/v) to give a solid. The solid was suspended in acetone to give 6-[5-amino-3-phenyl-6-(phenylethynyl)-2-pyrazinyl]-2-methyl-3(2H)-pyridazinone (96 mg).

m.p.: 234-236° C.

IR (KBr): 3465, 3278, 2195, 1666, 1626, 1587 $cm^{-1}$

Mass (ESI): 402 $(M+Na)^+$ $^1$H NMR (DMSO-$d_6$, δ): 3.46 (3H, s), 6.90 (1H, d, J=9.68 Hz), 7.20 (2H, brs), 7.39 (5H, s), 7.43-7.57 (4H, m), 7.74-7.82 (2H, m)

EXAMPLE 78

Under nitrogen atmosphere, a solution of $Na_2CO_3$ (220 mg) in water (1.6 ml) was added to a suspension of 6-(5-amino-6-bromo-3-phenyl-2-pyrazinyl)-2-isopropyl-3(2H)-pyridazinone (200 mg), phenylboronic acid (158 mg) and tetrakis(triphenylphosphine)palladium (18 mg) in dioxane (6 ml) and the mixture was stirred at 100-105° C. for 2 hours. After addition of water (6 ml), a precipitate was collected by filtration and purified by column chromatography on silica gel eluting with a mixture of n-hexane and EtOAc (60:40 v/v) to give a solid. The solid was suspended in acetone and collected by filtration to give 6-(5-amino-3,6-diphenyl-2-pyrazinyl)-2-isopropyl-3(2H)-pyridazinone (150 mg).

m.p.: 225-226° C.

IR (KBr): 3489, 3105, 1660, 1624, 15191, 1506 $cm^{-1}$

Mass (ESI): 406 $(M+Na)^+$, 384 $(M+H)^+$ $^1$H NMR ($CDCl_3$, δ): 0.84 (6H, d, J=6.70 Hz), 4.97-5.17 (3H, m), 6.94 (1H, d, J=9.56 Hz), 7.32-7.55 (8H, m), 7.80-7.90 (3H, m)

The following 11 compounds were obtained in a similar manner to that of Example 78.

EXAMPLE 79

6-[5-amino-3-phenyl-6-(3-thienyl)-2-pyrazinyl]-2-isopropyl-3(2H)-pyridazinone m.p.: 228-230° C.

IR (KBr): 3479, 3124, 2979, 1657, 1624, 1591, 1527, 1504 $cm^{-1}$

Mass (ESI): 412 $(M+Na)^+$, 390 $(M+H)^+$ $^1$H NMR ($CDCl_3$, δ): 0.84 (6H, d, J=6.60 Hz), 5.08 (1H, 7-plet, J=6.60 Hz), 5.16 (2H, brs), 6.95 (1H, d, J=9.54 Hz), 7.33-7.44 (5H, m), 7.49-7.53 (1H, m), 7.64-7.68 (1H, m), 7.67-7.90 (2H, m)

EXAMPLE 80

6-[5-amino-3-phenyl-6-(2-thienyl)-2-pyrazinyl]-2-isopropyl-3(2H)-pyridazinone m.p.: 181-183° C.

IR (KBr): 3168, 1630, 1576, 1523, 1504 $cm^{-1}$

Mass (ESI): 801 $(2M+Na)^+$, 412 $(M+Na)^+$, 390 $(M+H)^+$ $^1$H NMR ($CDCl_3$, δ): 0.83 (6H, d, J=6.65 Hz), 5.07 (1H, 7-plet, J=6.65 Hz), 6.21 (2H, brs), 6.98 (1H, d, J=9.63 Hz), 7.20 (1H, dd, J=3.71, 5.12 Hz), 7.33-7.43 (5H, m), 7.48-7.52 (1H, m), 7.64-7.67 (1H, m), 7.91 (1H, d, J=9.63 Hz)

EXAMPLE 81

6-[5-amino-6-(3-furyl)-3-phenyl-2-pyrazinyl]-2-isopropyl-3(2H)-pyridazinone m.p.: 233-235° C.

IR (KBr): 3494, 3267, 3113, 2979, 1657, 1622, 1589, 1514 $cm^{-1}$

Mass (ESI): 396 $(M+Na)^+$, 374 $(M+H)^+$ $^1$H NMR ($CDCl_3$, δ): 0.84 (6H, d, J=6.60 Hz), 4.99-5.16 (3H, m), 6.96 (1H, d, J=9.56 Hz), 7.02 (1H, s), 7.30-7.44 (5H, m), 7.58-7.61 (1H, m), 7.86 (1H, d, J=9.56 Hz), 8.05 (1H, s)

EXAMPLE 82

6-[5-amino-3-phenyl-6-(4-pyridyl)-2-pyrazinyl]-2-isopropyl-3(2H)-pyridazinone
  m.p.: 222-224° C.
  IR (KBr): 3325, 3197, 1658, 1653, 1641, 1587, 1556, 1531, 1506 cm$^{-1}$
  Mass (ESI): 791 (2M+Na)$^+$, 407 (M+Na)$^+$, 385 (M+H)$^+$
  $^1$H NMR (CDCl$_3$, δ): 0.84 (6H, d, J=6.60 Hz), 5.08 (1H, 7-plet, J=6.60 Hz), 5.15 (2H, brs), 6.97 (1H, d, J=9.58 Hz), 7.30-7.48 (5H, m), 7.88-7.93 (3H, m), 8.77-8.81 (2H, m)

EXAMPLE 83

6-[5-amino-6-(6-methoxy-3-pyridyl)-3-phenyl-2-pyrazinyl]-2-isopropyl-3(2H)-pyridazinone
  m.p.: 230-232.5° C.
  IR (KBr): 3425, 3329, 3201, 2974, 1657, 1626, 1585, 1539, 1506 cm$^{-1}$
  Mass (ESI): 851 (2M+Na)$^+$, 437 (M+Na)$^+$, 415 (M+H)$^+$
  $^1$H NMR (CDCl$_3$, δ): 0.84 (6H, d, J=6.60 Hz), 4.02 (3H, s), 4.99-5.15 (3H, m), 6.91 (1H, d, J=8.58 Hz), 6.94 (1H, d, J=9.56 Hz), 7.30-7.46 (5H, m), 7.84 (1H, d, J=9.56 Hz), 8.06 (1H, dd, J=2.48, 8.58 Hz), 8.68 (1H, d, J=2.48 Hz)

EXAMPLE 84

6-[5-amino-3-phenyl-6-(3-pyridyl)-2-pyrazinyl]-2-isopropyl-3(2H)-pyridazinone
  m.p.: 224-225.5° C.
  IR (KBr): 3394, 3330, 3167, 1647, 1585, 1531, 1506 cm$^{-1}$
  Mass (ESI): 791 (2M+Na)$^+$, 407 (M+Na)$^+$, 385 (M+H)$^+$
  $^1$H NMR (DMSO-d$_6$, δ): 0.74 (6H, d, J=6.60 Hz), 4.90 (1H, 7-plet, J=6.60 Hz), 6.83 (2H, brs), 6.96 (1H, d, J=9.65 Hz), 7.32-7.42 (5H, m), 7.54 (1H, dd, J=4.75, 7.95 Hz), 7.92 (1H, d, J=9.65 Hz), 8.17-8.24 (1H, m), 8.65 (1H, dd, J=1.65, 4.75 Hz), 9.00 (1H, d, J=1.65 Hz)

EXAMPLE 85

6-(5-amino-3,6-diphenyl-2-pyrazinyl)-2-methyl-3(2H)-pyridazinone
  m.p.: 220-221.5° C.
  IR (KBr): 3494, 3477, 3269, 3143, 1662, 1618, 1585, 1508 cm$^{-1}$
  Mass (ESI): 733 (2M+Na)$^+$, 378 (M+Na)$^+$, 356 (M+H)$^+$
  $^1$H NMR (CDCl$_3$, δ): 3.55 (3H, s), 5.11 (2H, brs), 6.85 (1H, d, J=9.68 Hz), 7.36-7.58 (9H, m), 7.57-7.84 (2H, m)

EXAMPLE 86

6-[5-amino-3-phenyl-6-(2-thienyl)-2-pyrazinyl]-2-methyl-3(2H)-pyridazinone
  m.p.: 177° C. (dec.)
  IR (KBr): 3417, 3303, 3188, 1645, 1574, 1525, 1502 cm$^{-1}$
  Mass (ESI): 745 (2M+Na)$^+$, 384 (M+Na)$^+$, 362 (M+H)$^+$
  $^1$H NMR (DMSO-d$_6$, δ): 3.34 (3H, s), 6.88 (2H, brs), 6.97 (1H, d, J=9.62 Hz), 7.22 (1H, dd, J=3.75, 5.05 Hz), 7.35-7.47 (5H, m), 7.68-7.74 (2H, m), 7.82 (1H, m)

EXAMPLE 87

6-{5-amino-3-phenyl-6-[(E)-2-phenylvinyl]-2-pyrazinyl}-2-isopropyl-3(2H)-pyridazinone
  m.p.: 244.5-245° C.
  IR (KBr): 3334, 3207, 1633, 1576, 1531, 1506 cm$^{-1}$
  Mass (ESI): 432 (M+Na)$^+$, 410 (M+H)$^+$
  $^1$H NMR (DMSO-d$_6$, δ): 0.74 (6H, d, J=6.60 Hz), 4.90 (1H, 7-plet, J=6.60 Hz), 6.98-7.03 (3H, m), 7.29-7.47 (8H, m), 7.60-7.79 (4H, m), 8.01 (1H, d, J=9.56 Hz)

EXAMPLE 88

6-[5-amino-6-(2-furyl)-3-phenyl-2-pyrazinyl]-2-isopropyl-3(2H)-pyridazinone
  m.p.: 211-213° C.
  IR (KBr): 3475, 3134, 1662, 1630, 1591, 1535, 1506 cm$^{-1}$
  Mass (ESI): 396 (M+Na)$^+$, 374 (M+H)$^+$
  $^1$H NMR (CDCl$_3$, δ): 0.84 (6H, d, J=6.60 Hz), 5.08 (1H, 7-plet, J=6.60 Hz), 5.87 (2H, brs), 6.63-6.65 (1H, m), 6.97 (1H, d, J=9.58 Hz), 7.20-7.23 (1H, m), 7.32-7.41 (5H, m), 7.61-7.63 (1H, m), 7.86 (1H, d, J=9.58 Hz)

EXAMPLE 89

6-[5-amino-6-(2-furyl)-3-phenyl-2-pyrazinyl]-2-methyl-3(2H)-pyridazinone
  m.p.: 186-188° C.
  IR (KBr): 3471, 3290, 3155, 1658, 1626, 1583, 1535, 1512 cm$^{-1}$
  Mass (ESI): 713 (2M+Na)$^+$, 368 (M+Na)$^+$, 346 (M+H)$^+$
  $^1$H NMR (DMSO-d$_6$, δ): 3.36 (3H, s), 6.72-6.76 (1H, m), 6.93 (1H, d, J=9.58 Hz), 6.96 (2H, brs), 7.20-7.23 (1H, m), 7.35-7.44 (5H, m), 7.71 (1H, d, J=9.58 Hz), 7.90-7.91 (1H, m)

EXAMPLE 90

Under nitrogen atmosphere, a solution of sodium carbonate (330 mg) in water (2.4 ml) was added to a suspension of 6-(5-amino-6-bromo-3-phenyl-2-pyrazinyl)-2-isopropyl-3(2H)-pyridazinone (300 mg), tert-butyl 4-(4,4,5,5-tetramethyl-1,3,2-dioxaborolan-2-yl)-1H-pyrazole-1-carboxylate (573 mg) and tetrakis(triphenylphosphine)palladium (27 mg) in dioxane (6 ml) and the mixture was stirred at 100-105° C. for 4 hours. After addition of water (30 ml), a precipitate was collected by filtration and purified by column chromatography on silica gel eluting with a mixture of n-hexane and EtOAc (10:90 v/v) to give a solid. The solid was suspended in acetone and collected by filtration to give 6-[5-amino-3-phenyl-6-(1H-pyrazol-4-yl)-2-pyrazinyl]-2-isopropyl-3(2H)-pyridazinone (211 mg).
  m.p.: >250° C.
  IR (KBr): 3384, 3305, 3209, 1657, 1591 cm$^{-1}$
  Mass (ESI): 769 (2M+Na)$^+$, 396 (M+Na)$^+$, 374 (M+H)$^+$
  $^1$H NMR (DMSO-d$_6$, δ): 0.74 (6H, d, J=6.60 Hz), 4.90 (1H, 7-plet, J=6.60 Hz), 6.57 (2H, brs), 6.97 (1H, d, J=9.60 Hz), 7.26-7.38 (5H, m), 7.98 (1H, d, J=9.60 Hz), 8.15 (1H, brs), 8.41 (1H, brs), 13.23 (1H, brs)

EXAMPLE 91

Under ice-cooling, sodium borohydride (30.7 mg) was added to a solution of 4-[3-amino-6-(1-isopropyl-6-oxo-1,6-dihydro-3-pyridazinyl)-5-phenyl-2-pyrazinyl]-1-methylpyridinium iodide (142 mg) in MeOH (4.26 ml) and the mixture was stirred at the same temperature for 30 minutes. After addition of 1N HCl (0.6 ml), MeOH was evaporated under reduced pressure to give a residue. The residue was dissolved in CHCl$_3$, dried over MgSO$_4$ and purified by column chromatography on silica gel eluting with a mixture of MeOH and EtOAc (5:95 v/v) to give a solid. The solid was suspended in acetone and collected by filtration to give 6-[5-amino-6-(1-methyl-1,2,3,6-tetrahydro-4-pyridyl)-3-phenyl-2-pyrazinyl]-2-isopropyl-3(2H)-pyridazinone (15 mg).

m.p.: 209-211° C.

IR (KBr): 3411, 3323, 2978, 1662, 1630, 1585, 1527, 1502 cm$^{-1}$

Mass (ESI): 403 (M+H)$^+$ $^1$H NMR (CDCl$_3$, δ): 0.82 (6H, d, J=6.60 Hz), 2.60 (3H, s), 2.90-2.96 (4H, m), 3.64-3.40 (2H, m), 5.06 (1H, 7-plet, J=6.60 Hz), 5.24 (2H, brs), 6.35 (1H, brs), 6.93 (1H, d, J=9.60 Hz), 7.26-7.40 (5H, m), 7.78 (1H, d, J=9.60 Hz)

EXAMPLE 92

6-[5-amino-6-(1-methyl-1,2,5,6-tetrahydro-3-pyridyl)-3-phenyl-2-pyrazinyl]-2-isopropyl-3(2H)-pyridazinone The title compound was obtained in a similar manner to that of Example 91.

m.p.: 191-193° C.

IR (KBr): 3433, 3271, 3159, 2780, 1657, 1622, 1587, 1529, 1506 cm$^{-1}$

Mass (ESI): 403 (M+H)$^+$ $^1$H NMR (CDCl$_3$, δ): 0.82 (6H, d, J=6.60 Hz), 2.60 (3H, s), 2.90-2.96 (4H, m), 3.64-3.40 (2H, m), 5.06 (1H, 7-plet, J=6.60 Hz), 5.24 (2H, brs), 6.35 (1H, brs), 6.93 (1H, d, J=9.60 Hz), 7.26-7.40 (5H, m), 7.78 (1H, d, J=9.60 Hz)

EXAMPLE 93

Under nitrogen atmosphere, 6-[5-amino-3-phenyl-6-(1H-pyrazol-4-yl)-2-pyrazinyl]-2-isopropyl-3(2H)-pyridazinone (120 mg) was added to a suspension of NaH (60% in oil) (14.2 mg) and the mixture was stirred at 25-30° C. for 30 minutes. The mixture was cooled in an ice bath and iodomethane (0.1 ml) was added. The mixture was stirred at the same time for 30 minutes and at 20-30° C. for one hour. After addition of water (3.6 ml), a precipitate was collected by filtration and purified by column chromatography on silica gel (EtOAc only) to give a solid. The solid was suspended in acetone and collected by filtration to give 6-[5-amino-6-(1-methyl-1H-pyrazol-4-yl)-3-phenyl-2-pyrazinyl]-2-isopropyl-3(2H)-pyridazinone (70 mg).

m.p.: 201-203° C.

IR (KBr): 3444, 3346, 1657, 1581, 1568, 1504 cm$^{-1}$

Mass (ESI): 797 (2M+Na)$^+$, 410 (M+Na)$^+$, 388 (M+H)$^+$ $^1$H NMR (CDCl$_3$, δ): 0.84 (6H, d, J=6.60 Hz), 4.02 (3H, s), 5.07 (1H, 7-plet, J=6.60 Hz), 5.23 (2H, brs), 6.96 (1H, d, J=9.60 Hz), 7.30-7.47 (5H, m), 7.84 (1H, d, J=9.60 Hz), 7.99 (1H, s), 8.05 (1H, s)

EXAMPLE 94

In the presence of palladium acetate (8.7 mg), 1,3-bis(diphenylphosphino)propane (35.3 mg) and potassium carbonate (215 mg), a mixture of 6-(5-amino-6-bromo-3-phenyl-2-pyrazinyl)-2-isopropyl-3(2H)-pyridazinone (501 mg) in butyl vinyl ether (1.5 ml) was refluxed for 20 hours. After addition of water, the mixture was extracted with CHCl$_3$ dried over MgSO$_4$ and concentrated under reduced pressure to give syrup. The syrup was purified by column chromatography on silica gel eluting with a mixture of n-hexane and EtOAc (50:50 v/v) to give a solid. The solid was suspended in acetone and collected by filtration to give 6-(6-acetyl-5-amino-3-phenyl-2-pyrazinyl)-2-isopropyl-3(2H)-pyridazinone (28 mg).

m.p.: 234-236.5° C.

IR (KBr): 3419, 3278, 1672, 1662, 1591, 1537, 1508 cm$^{-1}$

Mass (ESI): 721 (2M+Na)$^+$, 372 (M+Na)$^+$, 350 (M+H)$^+$ $^1$H NMR (CDCl$_3$, δ): 0.82 (6H, d, J=6.70 Hz), 2.76 (3H, s), 5.07 (1H, 7-plet, J=6.70 Hz), 7.00 (1H, d, J=9.60 Hz), 7.35-7.46 (5H, m), 7.85 (1H, d, J=9.60 Hz)

$^1$H NMR (DMSO-d$_6$, δ): 0.73 (6H, d, J=6.61 Hz), 2.67 (3H, s), 4.89 (1H, 7-plet, J=6.61 Hz), 7.03 (1H, d, J=9.65 Hz), 7.35-7.44 (5H, m), 7.97 (1H, d, J=9.65 Hz), 8.01 (2H, brs)

EXAMPLE 95

In the presence of palladium acetate (14.6 mg) and triphenylphosphine (34.0 mg), diisopropylethylamine (0.687 ml) was added to a mixture of 6-(5-amino-6-bromo-3-phenyl-2-pyrazinyl)-2-isopropyl-3(2H)-pyridazinone (501 mg) in DMF (2 ml) and the mixture was heated at 100-105° C. for 20 hours. After addition of water, a precipitate was collected by filtration and purified by column chromatography on silica gel eluting with a mixture of n-hexane and EtOAc (50:50 v/v) to give a solid. The solid was suspended in acetone and collected by filtration to give ethyl 3-[3-amino-6-(1-isopropyl-6-oxo-1,6-dihydro-3-pyridazinyl)-5-phenyl-2-pyrazinyl]acrylate (95 mg).

m.p.: 233-236° C.

IR (KBr): 3421, 3319, 3197, 1697, 1653, 1581, 1541 cm$^{-1}$

Mass (ESI): 833 (2M+Na)$^+$, 428 (M+Na)$^+$ $^1$H NMR (CDCl$_3$, δ): E-isomer; 0.82 (6H, d, J=6.56 Hz), 1.36 (3H, t, J=7.18 Hz), 4.29 (2H, q, J=7.18 Hz), 4.97-5.12 (3H, m), 6.98 (1H, d, J=9.56 Hz), 7.04 (1H, d, J=15.36 Hz), 7.30-7.49 (5H, m), 7.73 (1H, d, J=15.36 Hz), 7.88 (1H, d, J=9.56 Hz) Z-isomer; 6.85 (1H, d, J=9.54 Hz)

EXAMPLE 96

A mixture of 6-(5-amino-6-bromo-3-phenyl-2-pyrazinyl)-2-isopropyl-3(2H)-pyridazinone (100 mg) and benzylamine (0.085 ml) in DMA (0.2 ml) was heated at 120-125° C. for 50 hours. After addition of water (4 ml), an aqueous layer was removed by decantation to give a residue. The residue was dissolved in CHCl$_3$, dried over MgSO$_4$, concentrated under reduced pressure and purified by preparative TLC on silica gel (CHCl$_3$ only). A less polar zone was gave 6-[5-amino-6-(dimethylamino)-3-phenyl-2-pyrazinyl]-2-isopropyl-3(2H)-pyridazinone as a solid (18 mg) and a more polar zone was gave 6-[5-amino-6-(benzylamino)-3-phenyl-2-pyrazinyl]-2-isopropyl-3(2H)-pyridazinone as a solid (67 mg).

6-[5-amino-6-(benzylamino)-3-phenyl-2-pyrazinyl]-2-isopropyl-3(2H)-pyridazinone m.p.: 181-183.5° C.

IR (KBr): 3375, 3332, 3249, 3203, 1645, 1579, 1552, 1518 cm$^{-1}$

Mass (ESI): 847 (2M+Na)$^+$, 435 (M+Na)$^+$, 413 (M+H)$^+$ $^1$H NMR (CDCl$_3$, δ): 0.83 (6H, d, J=6.60 Hz), 4.68 (2H, d, J=5.24 Hz), 4.93-5.18 (1H, m), 6.84 (1H, d, J=9.56 Hz), 7.17-7.45 (5H, m), 7.66 (1H, d, J=9.56 Hz)

6-[5-amino-6-(dimethylamino)-3-phenyl-2-pyrazinyl]-2-isopropyl-3(2H)-pyridazinone m.p.: 174-176° C.

IR (KBr): 3494, 3255, 3155, 3122, 2979, 1660, 1614, 1589, 1500 cm$^{-1}$

Mass (ESI): 723 (2M+Na)$^+$, 373 (M+Na)$^+$, 351 (M+H)$^+$

¹H NMR (CDCl₃, δ): 0.83 (6H, d, J=6.60 Hz), 2.91 (6H, s), 4.97 (2H, brs), 5.06 (1H, 7-plet, J=6.60 Hz), 6.93 (1H, d, J=9.56 Hz), 7.23-7.35 (5H, m), 7.81 (1H, d, J=9.56 Hz)

The following compounds were obtained in a similar manner to that of Example 96.

EXAMPLE 97

6-{5-amino-6-[(4-methoxybenzyl)amino]-3-phenyl-2-pyrazinyl}-2-isopropyl-3(2H)-pyridazinone
  m.p.: 188.5-191.5° C.
  IR (KBr): 3398, 3313, 3249, 3199, 1647, 1581, 1547, 1512 cm⁻¹
  Mass (ESI): 907 (2M+Na)⁺, 465 (M+Na)⁺, 443 (M+H)⁺
  ¹H NMR (CDCl₃, δ): 0.84 (6H, d, J=6.60 Hz), 3.80 (3H, s), 4.61 (2H, d, J=5.18 Hz), 4.95-5.13 (4H, m), 6.84-6.93 (3H, m), 7.17-7.36 (7H, m), 7.71 (1H, d, J=9.58 Hz)

EXAMPLE 98

6-{5-amino-3-phenyl-6-[(2-pyridylmethyl)amino]-2-pyrazinyl}-2-isopropyl-3(2H)-pyridazinone and 6-[5-amino-6-(dimethylamino)-3-phenyl-2-pyrazinyl]-2-isopropyl-3(2H)-pyridazinone 6-{5-amino-3-phenyl-6-[(2-pyridylmethyl)amino]-2-pyrazinyl}-2-isopropyl-3(2H)-pyridazinone
  m.p.: 192-194° C.
  IR (KBr): 3396, 3334, 3251, 3211, 1645, 1576, 1522 cm⁻¹
  Mass (ESI): 849 (2M+Na)⁺, 436 (M+Na)⁺, 414 (M+H)⁺
  ¹H NMR (CDCl₃, δ): 0.86 (6H, d, J=6.62 Hz), 4.84 (2H, d, J=3.94 Hz), 5.06 (1H, 7-plet, J=6.62 Hz), 6.26 (1H, brs), 6.89 (1H, d, J=9.56 Hz), 7.18-7.45 (9H, m), 7.65 (1H, d, J=9.56 Hz), 7.70-7.80 (1H, m), 8.51 (1H, d, J=4.42 Hz)

6-[5-amino-6-(dimethylamino)-3-phenyl-2-pyrazinyl]-2-isopropyl-3(2H)-pyridazinone
  m.p.: 174-176° C.
  IR (KBr): 3494, 3255, 3155, 3122, 2979, 1660, 1614, 1589, 1500 cm⁻¹
  Mass (ESI): 723 (2M+Na)⁺, 373 (M+Na)⁺, 351 (M+H)⁺
  ¹H NMR (CDCl₃, δ): 0.83(6H, d, J=6.60 Hz), 2.91 (6H, s), 4.97 (2H, brs), 5.06 (1H, 7-plet, J=6.60 Hz), 6.93 (1H, d, J=9.56 Hz), 7.23-7.35 (5H, m), 7.81 (1H, d, J=9.56 Hz)

EXAMPLE 99

In a sealed tube, a mixture of 6-(5-amino-6-bromo-3-phenyl-2-pyrazinyl)-2-isopropyl-3(2H)-pyridazinone (150 mg) and butylamine (0.116 ml) in 1,3-dimethyl-2-imidazolidinone (0.3 ml) was heated at 120-125° C. for 50 hours. After addition of water (3 ml), a precipitate was collected by filtration and purified by column chromatography on silica gel eluting with a mixture of n-hexane and EtOAc (50:50 v/v) to give a solid. The solid was suspended in acetone to give 6-[5-amino-6-(butylamino)-3-phenyl-2-pyrazinyl]-2-isopropyl-3(2H)-pyridazinone (71 mg).
  m.p.: 200-202° C.
  IR (KBr): 3379, 3286, 3240, 3194, 1653, 1576, 1554, 1518 cm⁻¹
  Mass (ESI): 779 (2M+Na)⁺, 401 (M+Na)⁺, 379 (M+H)⁺
  ¹H NMR (CDCl₃, δ): 0.85 (6H, d, J=6.60 Hz), 0.99 (3H, t, J=7.22 Hz), 1.37-1.77 (4H, m), 3.45-3.57 (2H, m), 4.54 (1H, brs), 4.73 (2H, brs), 5.07 (1H, 7-plet, J=6.62 Hz), 6.92 (1H, d, J=9.54 Hz), 7.19-7.33 (5H, m), 7.78 (1H, d, J=9.54 Hz)

EXAMPLE 100

6-[5-amino-6-(butylamino)-3-phenyl-2-pyrazinyl]-2-methyl-3(2H)-pyridazinone

The title compound was obtained in a similar manner to that of Example 99.
  m.p.: 253-255° C.
  IR (KBr): 3450, 3363, 3224, 1649, 1581, 1574, 1550, 1520, 1508 cm⁻¹
  Mass (ESI): 373 (M+Na)⁺, 351 (M+H)⁺
  ¹H NMR (DMSO-d₆, δ) 0.93 (3H, t, J=7.21 Hz), 1.30-1.50 (2H, m), 1.54-1.69 (2H, m), 3.33 (3H, s), 3.32-3.45 (2H, m), 6.36-6.44 (3H, m), 6.89 (1H, d, J=9.58 Hz), 7.18-7.29 (5H, m), 7.59 (1H, d, J=9.58 Hz)

EXAMPLE 101

A mixture of 6-(5-amino-6-bromo-3-phenyl-2-pyrazinyl)-2-isopropyl-3(2H)-pyridazinone (150 mg) and allylamine (0.0881 ml) in 1,3-dimethyl-2-imidazolidinone (0.3 ml) was heated at 120-125° C. for 50 hours. After addition of water (3 ml), an aqueous layer was removed by decantation to give a residue. The residue was dissolved in CHCl₃, dried over MgSO₄ and concentrated under reduced pressure to give syrup. The syrup was crystallized from a mixture of acetone and hexane to give 6-[6-(allylamino)-5-amino-3-phenyl-2-pyrazinyl]-2-isopropyl-3(2H)-pyridazinone (71 mg).
  m.p.: 208-210° C.
  IR (KBr): 3398, 3340, 3182, 1645, 1583, 1554, 1525 cm⁻¹
  Mass (ESI): 747 (2M+Na)⁺, 385 (M+Na)⁺, 363 (M+H)⁺
  ¹H NMR (CDCl₃, δ): 0.84 (6H, d, J=6.60 Hz), 4.11-4.20 (2H, m), 4.73-4.88 (3H, m), 5.06 (1H, 7-plet, J=6.60 Hz), 5.15-5.37 (2H, m), 5.95-6.15 (1H, m), 6.92 (1H, d, J=9.56 Hz), 7.20-7.33 (5H, m), 7.78 (1H, d, J=9.56 Hz)

The following 30 compounds were obtained in a similar manner to that of Example 101.

EXAMPLE 102

6-{5-amino-6-[(2-methoxyethyl)amino]-3-phenyl-2-pyrazinyl}-2-isopropyl-3(2H)-pyridazinone
  m.p.: 208-209.5° C.
  IR (KBr): 3398, 3340, 3180, 1651, 1579, 1554, 1525 cm⁻¹
  Mass (ESI): 403 (M+Na)⁺, 381 (M+H)⁺
  ¹H NMR (CDCl₃, δ): 0.86 (6H, d, J=6.62 Hz), 3.41 (3H, s), 3.63-3.77 (4H, m), 4.78 (2H, brs), 4.91 (1H, brs), 5.07 (1H, 7-plet, J=6.62 Hz), 6.92 (1H, d, J=9.54 Hz), 7.18-7.33 (5H, m), 7.74 (1H, d, J=9.54 Hz)

EXAMPLE 103

6-(5-amino-3-phenyl-6-{[2-(1-piperidinyl)ethyl]amino}-2-pyrazinyl)-2-isopropyl-3(2H)-pyridazinone
  m.p.: 204.5-207° C.
  IR (KBr): 3398, 3342, 3238, 3203, 2933, 1653, 1579, 1552, 1522, 1512 cm⁻¹
  Mass (ESI): 889 (2M+Na)⁺, 456 (M+Na)⁺, 434 (M+H)⁺
  ¹H NMR (CDCl₃, δ): 0.85 (6H, d, J=6.60 Hz), 1.48-1.72 (6H, m), 2.47-2.55 (4H m), 2.67-2.80 (2H, m), 3.53-3.65 (2H, m), 4.83 (2H, brs), 5.07 (1H, 7-plet, J=6.60 Hz), 5.42 (1H, t, J=4.33 Hz), 6.90 (1H, d, J=9.54 Hz), 7.15-7.34 (5H, m), 7.75 (1H, d, J=9.54 Hz)

EXAMPLE 104

6-(5-amino-6-{[2-(4-morpholinyl)ethyl]amino}-3-phenyl-2-pyrazinyl)-2-isopropyl-3(2H)-pyridazinone m.p.: 230-232.5° C.

IR (KBr): 3394, 3363, 3211, 3188, 16449, 1579, 1554, 1525 cm$^{-1}$

Mass (ESI): 458 (M+Na)$^+$, 436 (M+H)$^+$ $^1$H NMR (CDCl$_3$, δ): 0.85 (6H, d, J=6.62 Hz), 2.58-2.71 (4H, m), 2.79 (2H, t, J=5.81 Hz), 3.57-3.68 (2H, m), 3.75-3.82 (4H, m), 4.74 (2H, brs), 5.07 (1H, 7-plet, J=6.62 Hz), 5.24 (1H, t, J=4.39 Hz), 6.91 (1H, d, J=9.56 Hz), 7.15-7.32 (5H, m), 7.74 (1H, d, J=9.56 Hz)

EXAMPLE 105

6-{5-amino-6-[(cyclohexylmethyl)amino]-3-phenyl-2-pyrazinyl}-2-isopropyl-3(2H)-pyridazinone m.p.: 219-221° C.

IR (KBr): 3373, 3319, 3232, 3197, 2925, 1651, 1577, 1550, 1512 cm$^{-1}$

Mass (ESI): 859 (2M+Na)$^+$, 441 (M+Na)$^+$, 419 (M+H)$^+$ $^1$H NMR (CDCl$_3$, δ): 0.86 (6H, d, J=6.62 Hz), 0.84-2.30 (11H, m), 3.31-3.39 (2H, m), 4.79 (1H, brs), 4.89 (2H, brs), 5.07 (1H, 7-plet, J=6.62 Hz), 6.93 (1H, d, J=9.56 Hz), 7.17-7.33 (5H, m), 7.76 (1H, d, J=9.56 Hz)

EXAMPLE 106

6-(5-amino-3-phenyl-6-{[2-(2-pyridyl)ethyl]amino}-2-pyrazinyl)-2-isopropyl-3(2H)-pyridazinone m.p.: 204-206° C.

IR (KBr): 3396, 3342, 3251, 3205, 1647, 1577, 1523 cm$^{-1}$

Mass (ESI): 877 (2M+Na)$^+$, 450 (M+Na)$^+$, 428 (M+H)$^+$ $^1$H NMR (CDCl$_3$, δ): 0.85 (6H, d, J=6.60 Hz), 3.21 (2H, t, J=6.14 Hz), 3.90 (2H, t, J=6.14 Hz), 4.77 (2H, brs), 5.06 (1H, 7-plet, J=6.60 Hz), 6.80 (1H, brs), 6.91 (1H, d, J=9.54 Hz), 7.16-7.35 (7H, m), 7.64-7.74 (1H, m), 7.76 (1H, d, J=9.54 Hz), 8.54 (1H, d, J=4.28 Hz)

EXAMPLE 107

6-{5-amino-6-[(1-benzyl-4-piperidinyl)amino]-3-phenyl-2-pyrazinyl}-2-isopropyl-3(2H)-pyridazinone m.p.: 214-216.5° C.

IR (KBr): 3369, 3190, 2939, 1643, 1576, 1547, 1523 cm$^{-1}$

Mass (ESI): 518 (M+Na)$^+$, 496 (M+H)$^+$ $^1$H NMR (CDCl$_3$, δ): 0.86 (6H, d, J=6.60 Hz), 1.52-2.32 (6H, m), 2.88-3.02 (2H, m), 3.58 (2H, s), 3.94-4.06 (1H, m), 4.48 (1H, d, J=6.84 Hz), 4.63 (2H, brs), 5.07 (1H, 7-plet, J=6.60 Hz), 6.91 (1H, d, J=9.55 Hz), 7.17-7.36 (1H, m), 7.67 (1H, d, J=9.55 Hz)

EXAMPLE 108

6-[5-amino-3-phenyl-6-(1-piperidinyl)-2-pyrazinyl]-2-isopropyl-3(2H)-pyridazinone m.p.: 183-185° C.

IR (KBr): 3450, 3265, 3161, 2935, 1666, 1614, 1589, 1502 cm$^{-1}$

Mass (ESI): 803 (2M+Na)$^+$, 413 (M+Na)$^+$, 391 (M+H)$^+$ $^1$H NMR (CDCl$_3$, δ): 0.83 (6H, d, J=6.60 Hz), 1.67-1.80 (6H, m), 3.16-3.24 (4H, m), 4.98 (2H, brs), 5.06 (1H, 7-plet, J=6.60 Hz), 6.93 (1H, d, J=9.56 Hz), 7.21-7.35 (5H, m), 7.80 (1H, d, J=9.56 Hz)

EXAMPLE 109

6-{5-amino-6-[3-(dimethylamino)-1-pyrrolidinyl]-3-phenyl-2-pyrazinyl}-2-isopropyl-3(2H)-pyridazinone m.p.: 150-152° C.

IR (KBr): 3448, 3286, 3185, 2974, 1657, 1622, 1589, 1529 cm$^{-1}$

Mass (ESI): 442 (M+Na)$^+$, 420 (M+H)$^+$ $^1$H NMR (CDCl$_3$, δ): 0.82 (3H, d, J=6.60 Hz), 0.87 (3H, d, J=6.60 Hz), 1.90-2.10 (1H, m), 2.15-2.30 (1H, m), 2.40 (6H, s), 2.83-2.97 (1H, m), 3.50-3.75 (4H, m), 4.79 (2H, brs), 5.06 (1H, 7-plet, J=6.60 Hz), 6.91 (1H, d, J=9.56 Hz), 7.17-7.37 (5H, m), 7.77 (1H, d, J=9.56 Hz)

EXAMPLE 110

6-[5-amino-6-(4-methoxy-1-piperidinyl)-3-phenyl-2-pyrazinyl]-2-isopropyl-3(2H)-pyridazinone m.p.: 179-181° C.

IR (KBr): 3487, 3248, 3113, 1660, 1589, 1506 cm$^{-1}$

Mass (ESI): 863 (2M+Na)$^+$, 443 (M+Na)$^+$, 421 (M+H)$^+$ $^1$H NMR (CDCl$_3$, δ): 0.83 (6H, d, J=6.62 Hz), 1.70-1.85 (2H, m), 2.05-2.17 (2H, m), 2.96-3.09 (2H, m), 3.41 (3H, s), 3.41-3.61 (3H, m), 4.96-5.14 (3H, m), 6.92 (1H, d, J=9.54 Hz), 7.23-7.37 (5H, m), 7.78 (1H, d, J=9.54 Hz)

EXAMPLE 111

N-{1-[3-amino-6-(1-isopropyl-6-oxo-1,6-dihydro-3-pyridazinyl)-5-phenyl-2-pyrazinyl]-4-piperidinyl}methanesulfonamide m.p.: 220-222° C.

IR (KBr): 3411, 3257, 3156, 1662, 1626, 1593, 1506 cm$^{-1}$

Mass (ESI): 989 (2M+Na)$^+$, 506 (M+Na)$^+$, 484 (M+H)$^+$ $^1$H NMR (CDCl$_3$, δ): 0.83 (6H, d, J=6.60 Hz), 1.65-1.85 (2H, m) 2.14-2.23 (2H, m), 2.91-3.04 (2H, m), 3.04 (3H, s), 3.48-3.68 (3H, m), 4.68 (1H, d, J=7.58 Hz), 4.96-5.11 (3H, m), 6.94 (1H, d, J=9.60 Hz), 7.22-7.36 (5H, m), 7.75 (1H, d, J=9.60 Hz)

$^1$H NMR (DMSO-d$_6$, δ): 0.73 (6H, d, J=6.60 Hz), 1.65-1.81 (2H, m), 1.91-2.00 (2H, m), 2.78-2.93 (2H, m), 2.96 (3H, s), 3.31-3.45 (1H, m), 3.54-3.64 (2H, m), 4.88 (1H, 7-plet, J=6.60 Hz), 6.41 (2H, brs), 6.95 (1H, d, J=9.56 Hz), 7.16-7.37 (5H, m), 7.83 (1H, d, J=9.56 Hz)

EXAMPLE 112

6-[5-amino-3-phenyl-6-(1-piperazinyl)-2-pyrazinyl]-2-isopropyl-3(2H)-pyridazinone m.p.: 157-159° C.

IR (KBr): 3446, 3321, 1651, 1579, 1541, 1506 cm$^{-1}$

Mass (ESI): 805 (2M+Na)$^+$, 414 (M+Na)$^+$, 392 (M+H)$^+$ $^1$H NMR (CDCl$_3$, δ): 0.86 (6H, d, J=6.60 Hz), 3.07-3.16 (4H, m), 3.22-3.30 (4H, m), 4.86 (2H, brs), 5.06 (1H, 7-plet, J=6.60 Hz), 6.93 (1H, d, J=9.54 Hz), 7.23-7.35 (5H, m), 7.79 (1H, d, J=9.54 Hz)

EXAMPLE 113

6-[5-amino-6-(4-methyl-1-piperazinyl)-3-phenyl-2-pyrazinyl]-2-isopropyl-3(2H)-pyridazinone m.p.: 155-157° C.

IR (KBr): 3440, 3261, 3132, 2968, 1664, 1622, 1587, 1506 cm$^{-1}$

Mass (ESI): 833 (2M+Na)$^+$, 428 (M+Na)$^+$, 406 (M+H)$^+$ $^1$H NMR (CDCl$_3$, δ): 0.83 (6H, d, J=6.60 Hz), 2.43 (3H, s), 2.64-2.71 (4H, m), 3.32-3.39 (4H, m), 4.84 (2H, brs), 5.06 (1H, 7-plet, J=6.60 Hz), 6.93 (1H, d, J=9.56 Hz), 7.22-7.36 (5H, m), 7.78 (1H, d, J=9.56 Hz)

EXAMPLE 114

6-{5-amino-3-phenyl-6-[4-(2-pyridylmethyl)-1-piperazinyl]-2-pyrazinyl}-2-isopropyl-3(2H)-pyridazinone m.p.: 88-91° C.

IR (KBr): 3384, 3294, 3136, 1660, 1633, 1587, 1504 cm$^{-1}$

Mass (ESI): 505 (M+Na)$^+$, 483 (M+H)$^+$ 0.83 (6H, d, J=6.60 Hz), 2.75-2.82 (4H, m), 3.32-3.42 (4H, m), 3.82 (2H, s), 4.85 (2H, brs), 5.06 (1H, 7-plet, J=6.60 Hz), 6.92 (1H, d, J=9.62 Hz), 7.18-7.36 (6H, m), 7.48-7.54 (1H, m), 7.65-7.75 (1H, m), 7.78 (1H, d, J=9.62 Hz), 8.58-8.62 (1H, m)

EXAMPLE 115

6-[5-amino-3-phenyl-6-(4-phenyl-1-piperazinyl)-2-pyrazinyl]-2-isopropyl-3(2H)-pyridazinone m.p.: 193-195° C.

IR (KBr): 3404, 3278, 3182, 1652, 1624, 1583, 1558, 1539 cm$^{-1}$

Mass (ESI): 490 (M+Na)$^+$, 468 (M+H)$^+$ 0.84 (6H, d, J=6.60 Hz), 3.36-3.51 (8H, m), 4.93 (2H, brs), 5.06 (1H, 7-plet, J=6.60 Hz), 6.87-7.07 (4H, m), 7.26-7.39 (7H, m), 7.80 (1H, d, J=9.60 Hz)

EXAMPLE 116

6-{5-amino-6-[4-(4-methoxyphenyl)-1-piperazinyl]-3-phenyl-2-pyrazinyl}-2-isopropyl-3(2H)-pyridazinone m.p.: 194-196° C.

IR (KBr): 3437, 3261, 3130, 2974, 2835, 1672, 1618, 1593, 1510 cm$^{-1}$

Mass (ESI): 520 (M+Na)$^+$, 498 (M+H)$^+$ $^1$H NMR (CDCl$_3$, δ): 0.83 (6H, d, J=6.60 Hz), 3.25-3.33 (4H, m), 3.44-3.51 (4H, m), 3.78 (3H, s), 4.91 (2H, brs), 5.07 (1H, 7-plet, J=6.60 Hz), 6.85-7.05 (5H, m), 7.23-7.39 (5H, m), 7.80 (1H, d, J=9.54 Hz)

EXAMPLE 117

6-[6-(4-acetyl-1-piperazinyl)-5-amino-3-phenyl-2-pyrazinyl]-2-isopropyl-3(2H)-pyridazinone m.p.: 221-225° C.

IR (KBr): 3359, 3290, 3170, 1664, 1649, 1626, 1591, 1541, 1504 cm$^{-1}$

Mass (ESI): 456 (M+Na)$^+$, 434 (M+H)$^+$ $^1$H NMR (CDCl$_3$, δ): 0.83 (6H, d, J=6.60 Hz), 2.17 (3H, s), 3.21-3.34 (4H, m), 3.61-3.71 (2H, m), 3.79-3.85 (2H, m), 4.96-5.15 (3H, m), 6.93 (1H, d, J=9.56 Hz), 7.28-7.37 (5H, m), 7.74 (1H, d, J=9.56 Hz)

EXAMPLE 118

6-[5-amino-6-(hexahydropyrrolo[1,2-a]pyrazin-2(1H)-yl)-3-phenyl-2-pyrazinyl]-2-isopropyl-3(2H)-pyridazinone m.p.: 205-207.5° C.

IR (KBr): 3477, 3444, 3267, 3132, 1662, 1620, 1589, 1504 cm$^{-1}$

Mass (ESI): 885 (2M+Na)$^+$, 454 (M+Na)$^+$, 432 (M+H)$^+$ $^1$H NMR (CDCl$_3$, δ): 0.83 (3H, d, J=6.60 Hz), 0.84 (3H, d, J=6.60 Hz), 1.50-1.62 (1H, m), 1.80-2.00 (3H, m), 2.27-2.90 (3H, m), 2.78-2.90 (1H, m), 3.06-3.25 (3H, m), 3.63-3.80 (2H, m), 4.84 (2H, brs), 5.06 (1H, 7-plet, J=6.60 Hz), 6.93 (1H, d, J=9.56 Hz), 7.20-7.35 (5H, m), 7.77 (1H, d, J=9.56 Hz)

EXAMPLE 119

6-[5-amino-6-(8-oxa-3-azabicyclo[3.2.1]oct-3-yl)-3-phenyl-2-pyrazinyl]-2-isopropyl-3(2H)-pyridazinone m.p.: 235-238° C.

IR (KBr): 3469, 3261, 3157, 3130, 1664, 1616, 1593, 1506 cm$^{-1}$

Mass (ESI): 441 (M+Na)$^+$, 419 (M+H)$^+$ $^1$H NMR (DMSO-d$_6$, δ): 0.73 (6H, d, J=6.60 Hz), 1.79-1.86 (2H, m), 2.08-2.20 (2H, m), 2.95-3.02 (2H, m), 3.32-3.40 (2H, m), 4.39 (2H, brs), 4.88 (1H, 7-plet, J=6.60 Hz), 6.16 (2H, brs), 6.95 (1H, d, J=9.60 Hz), 7.21-7.38 (5H, m), 7.84 (1H, d, J=9.60 Hz)

EXAMPLE 120

6-{5-amino-6-[(2-methoxyethyl)amino]-3-phenyl-2-pyrazinyl}-2-methyl-3(2H)-pyridazinone m.p.: 231-232.5° C.

IR (KBr): 3383, 3313, 3201, 1649, 1585, 1576, 1548 cm$^{-1}$

Mass (ESI): 375 (M+Na)$^+$, 353 (M+H)$^+$ $^1$H NMR (CDCl$_3$, δ): 3.42 (3H, s), 3.57 (3H, s), 3.61-3.77 (4H, m), 4.74 (2H, brs), 4.85 (1H, brs), 6.82 (1H, d, J=9.56 Hz), 7.26-7.36 (5H, m), 7.43 (1H, d, J=9.56 Hz)

$^1$H NMR (DMSO-d$_6$, δ): 3.30 (3H, s), 3.32 (3H, s), 3.55-3.63 (4H, m), 6.48 (2H, brs), 6.57 (1H, brs), 6.88 (1H, d, J=9.60 Hz), 7.20-7.31 (5H, m), 7.59 (1H, d, J=9.60 Hz)

EXAMPLE 121

6-(5-amino-3-phenyl-6-{[2-(1-piperidinyl)ethyl]amino}-2-pyrazinyl)-2-methyl-3(2H)-pyridazinone m.p.: 155-157° C.

IR (KBr): 3396, 3249, 3174, 2933, 1645, 1579, 1556 cm$^{-1}$

Mass (ESI): 428 (M+Na)$^+$, 406 (M+H)$^+$ $^1$H NMR (CDCl$_3$, δ): 1.47-1.73 (6H, m), 2.38-2.51 (4H, m), 2.68 (2H, t, J=5.79 Hz), 3.55-3.65 (2H, m), 3.58 (3H, s), 4.88 (2H, brs), 5.44 (1H, t, J=4.45 Hz), 6.79 (1H, d, J=9.56 Hz), 7.26-7.36 (5H, m), 7.40 (1H, d, J=9.56 Hz)

EXAMPLE 122

6-(5-amino-6-{[2-(4-morpholinyl)ethyl]amino}-3-phenyl-2-pyrazinyl)-2-methyl-3(2H)-pyridazinone m.p.: 226-229° C.

IR (KBr): 3388, 3330, 3307, 3215, 1649, 1577, 1572, 1545, 1516 cm$^{-1}$

Mass (ESI): 430 (M+Na)$^+$, 408 (M+H)$^+$

¹H NMR (CDCl₃, δ): 2.61-2.69 (2H, m), 2.77-2.86 (2H, m), 3.52-3.71 (4H, m), 3.58 (3H, s), 3.78-3.85 (4H, m), 4.79 (2H, brs), 5.35 (1H, brs), 6.80 (1H, d, J=9.58 Hz), 7.26-7.42 (6H, m)

EXAMPLE 123

6-{5-amino-6-[(2-anilinoethyl)amino]-3-phenyl-2-pyrazinyl}-2-methyl-3(2H)-pyridazinone
m.p.: 181-183° C.
IR (KBr): 3394, 3327, 3188, 1645, 1572, 1506 cm⁻¹
Mass (ESI): 849 (2M+Na)⁺, 436 (M+Na)⁺, 414 (M+H)⁺
¹H NMR (CDCl₃, δ): 3.47 (2H, t, J=5.64 Hz), 3.59 (3H, s), 3.75-3.86 (2H, m), 5.02 (2H, brs), 5.27 (1H, brs), 6.64-6.82 (4H, m), 7.12-7.20 (2H, m), 7.27-7.46 (7H, m)

EXAMPLE 124

6-{5-amino-6-[(2-furylmethyl)amino]-3-phenyl-2-pyrazinyl}-2-methyl-3(2H)-pyridazinone
m.p.: 249-252° C.
IR (KBr): 3438, 3348, 1647, 1574, 1554, 1522, 1504 cm⁻¹
Mass (ESI): 397 (M+Na)⁺, 375 (M+H)⁺
¹H NMR (CDCl₃, δ) 3.53 (3H, s), 4.69 (2H, d, J=5.26 Hz), 4.86 (1H, brs), 5.19 (2H, brs), 6.31-6.37 (1H, m), 6.84 (1H, d, J=9.56 Hz), 7.26-7.38 (7H, m), 7.50 (1H, d, J=9.56 Hz)
¹H NMR (DMSO-d₆, δ): 3.32 (3H, s), 4.61 (2H, d, J=5.10 Hz), 6.36-6.44 (2H, m), 6.49 (2H, brs), 6.86-6.94 (2H, m), 7.25-7.30 (5H, m), 7.58-7.64 (2H, m)

EXAMPLE 125

6-{5-amino-3-phenyl-6-[(2-phenylethyl)amino]-2-pyrazinyl}-2-methyl-3(2H)-pyridazinone
m.p.: 232-234° C.
IR (KBr): 3375, 3311, 3251, 3157, 1643, 1572, 1547, 1527 cm⁻¹
Mass (ESI): 819 (2M+Na)⁺, 421 (M+Na)⁺, 399 (M+H)⁺
¹H NMR (CDCl₃, δ): 3.01 (2H, t, J=7.02 Hz), 3.58 (3H, s), 3.74-3.85 (2H, m), 4.65 (1H, brs), 4.75 (2H, brs), 6.83 (1H, d, J=9.58 Hz), 7.19-7.37 (10H, m), 7.50 (1H, d, J=9.58 Hz)

EXAMPLE 126

6-{5-amino-3-phenyl-6-[(3-phenylpropyl)amino]-2-pyrazinyl}-2-methyl-3(2H)-pyridazinone
m.p.: 196-197.5° C.
IR (KBr): 3429, 3365, 1651, 1583, 1568, 1543, 1520 cm⁻¹
Mass (ESI): 847 (2M+Na)⁺, 435 (M+Na)⁺, 413 (M+H)⁺
¹H NMR (CDCl₃, δ): 1.96-2.19 (2H, m), 2.78 (2H, t, J=7.41 Hz), 3.51-3.73 (2H, m), 3.56 (3H, s), 4.52 (1H, brs), 4.62 (2H, brs), 6.82 (1H, d, J=9.60 Hz), 7.17-7.40 (10H, m), 7.44 (1H, d, J=9.60 Hz)

EXAMPLE 127

6-(5-amino-3-phenyl-6-{[2-(2-pyridyl)ethyl]amino}-2-pyrazinyl)-2-methyl-3(2H)-pyridazinone
m.p.: 224-227° C.
IR (KBr): 3404, 3356, 3188, 1651, 1585, 1570, 1543 cm⁻¹
Mass (ESI): 422 (M+Na)⁺, 400 (M+H)⁺
¹H NMR (CDCl₃, δ): 3.18 (2H, t, J=6.18 Hz), 3.56 (3H, s), 3.85-3.94 (2H, m), 4.79 (2H, brs), 5.86 (1H, brs), 6.81 (1H, d, J=9.6 Hz), 7.14-7.34 (7H, m), 7.45 (1H, d, J=9.60 Hz), 7.62-7.71 (1H, m), 8.51-8.56 (1H, m)

EXAMPLE 128

6-{5-amino-6-[(1-benzyl-3-pyrrolidinyl)amino]-3-phenyl-2-pyrazinyl}-2-methyl-3(2H)-pyridazinone
m.p.: 183-185° C.
IR (KBr): 3384, 3226, 1647, 1576, 1550, 1520 cm⁻¹
Mass (ESI): 476 (M+Na)⁺, 454 (M+H)⁺
¹H NMR (CDCl₃, δ): 1.75-1.83 (1H, m), 2.36-2.52 (2H, m), 2.76-2.82 (2H, m), 2.91-3.02 (1H, m), 3.51 (3H, s), 3.70 (2H, s), 4.63-4.73 (3H, m), 5.05 (1H, d, J=7.42 Hz), 6.83 (1H, d, J=9.60 Hz), 7.26-7.41 (10H, m), 7.48 (1H, d, J=9.60 Hz)

EXAMPLE 129

6-{5-amino-6-[(1-benzyl-4-piperidinyl)amino]-3-phenyl-2-pyrazinyl}-2-methyl-3(2H)-pyridazinone
m.p.: 191-194° C.
IR (KBr): 3373, 3238, 2943, 1649, 1576, 1549, 1520, 1508 cm⁻¹
Mass (ESI): 490 (M+Na)⁺, 468 (M+H)⁺
¹H NMR (CDCl₃, δ): 0.82-0.91 (1H, m), 1.55-1.77 (2H, m), 2.12-2.49 (3H, m), 2.90-2.99 (2H, m), 3.52 (3H, s), 3.60 (2H, s), 3.94-4.07 (1H, m), 4.60 (1H, d, J=6.84 Hz), 4.71 (2H, brs), 6.84 (1H, d, J=9.60 Hz), 7.26-7.42 (10H, m), 7.47 (1H, d, J=9.60 Hz)

EXAMPLE 130

6-[5-amino-3-phenyl-6-(4-phenyl-1-piperazinyl)-2-pyrazinyl]-2-methyl-3(2H)-pyridazinone
m.p.: 155-157° C.
IR (KBr): 3454, 3292, 3182, 3126, 2841, 1655, 1599, 1579, 1508 cm⁻¹
Mass (ESI): 901 (2M+Na)⁺, 462 (M+Na)⁺, 440 (M+H)⁺
¹H NMR (CDCl₃, δ): 3.35-3.52 (8H, m), 3.54 (3H, s), 4.95 (2H, brs), 6.84-7.05 (4H, m), 7.26-7.39 (7H, m), 7.57 (1H, d, J=9.58 Hz)

EXAMPLE 131

6-[5-amino-6-(hexahydropyrrolo[1,2-a]pyrazin-2(1H)-yl)-3-phenyl-2-pyrazinyl]-2-methyl-3(2H)-pyridazinone
m.p.: 177-179° C.
IR (KBr): 3491, 3373, 3126, 2952, 1668, 1657, 1616, 1583, 1508 cm⁻¹
Mass (ESI): 404 (M+H)⁺
¹H NMR (CDCl₃, δ): 1.53-2.02 (4H, m), 2.27-2.63 (3H, m), 2.77-2.91 (1H, m), 3.05-3.27 (3H, m), 3.49 (3H, s), 3.63-3.80 (2H, m), 4.85 (2H, brs), 6.87 (1H, d, J=9.60 Hz), 7.26-7.38 (5H, m), 7.57 (1H, d, J=9.60 Hz)

EXAMPLE 132

A mixture of 6-(5-amino-6-bromo-3-phenyl-2-pyrazinyl)-2-isopropyl-3(2H)-pyridazinone (150 mg) and N,N-dimethyl-1,2-ethanediamine (0.127 ml) in 1,2-dimethyl-2-imidazolidinone (0.3 ml) was heated at 120-125° C. for 50 hours. After addition of water (3 ml), the mixture was extracted with CHCl₃, dried over MgSO₄, concentrated under reduced pressure and purified by column chromatography on silica gel [Chromatorex® NH] eluting with a mixture of n-hexane and EtOAc (60:40 v/v) to give a syrup. The syrup was crystallized from a mixture of acetone and n-hexane to give 6-(5-amino-6-{[2-(dimethylamino)ethyl]amino}-3-phenyl-2-pyrazinyl)-2-isopropyl-3(2H)-pyridazinone (36 mg).

m.p.: 188-189° C.
IR (KBr): 3415, 3342, 2974, 1649, 1577, 1508 cm$^{-1}$
Mass (ESI): 416 (M+Na)$^+$, 394 (M+H)$^+$
$^1$H NMR (CDCl$_3$, δ): 0.86 (6H, d, J=6.60 Hz), 2.40 (6H, s), 2.17-2.78 (2H, t, J=5.69 Hz), 3.55-3.68 (2H, m), 4.82 (2H, brs), 5.07 (1H, 7-plet, J=6.60 Hz), 5.35 (1H, t, J=4.56 Hz), 6.90 (1H, d, J=9.56 Hz), 7.18-7.32 (5H, m), 7.74 (1H, d, J=9.56 Hz)

EXAMPLE 133

A mixture of 6-(5-amino-6-bromo-3-phenyl-2-pyrazinyl)-2-isopropyl-3(2H)-pyridazinone (150 mg) and N-(2-aminoethyl)acetamide (0.112 ml) in 1,2-dimethyl-2-imidazolidinone (0.3 ml) was heated at 120-125° C. for 50 hours. After addition of water (3 ml), an aqueous layer was removed by decantation to give a residue. The residue was dissolved in CHCl$_3$, dried over MgSO$_4$, concentrated under reduced pressure and purified by column chromatography on silica gel eluting with a mixture of MeOH and EtOAc (3:97 v/v) to give a solid. The solid was suspended in acetone to give N-(2-{[3-amino-6-(1-isopropyl-6-oxo-1,6-dihydro-3-pyridazinyl)-5-phenyl-2-pyrazinyl]amino}ethyl)acetamide (28 mg).

m.p.: 147-149° C.
IR (KBr): 3433, 3369, 3253, 1645, 1577, 1550, 1525 cm$^{-1}$
Mass (ESI): 430 (M+Na)$^+$, 408 (M+H)$^+$
$^1$H NMR (CDCl$_3$, δ): 0.84 (6H, d, J=6.60 Hz), 1.94 (3H, s), 3.48-3.66 (4H, m), 5.06 (1H, 7-plet, J=6.60 Hz), 6.63 (1H, brs), 6.80 (1H, brs), 6.91 (1H, d, J=9.56 Hz), 7.26-7.38 (5H, m), 7.70 (1H, d, J=9.56 Hz)
$^1$H NMR (DMSO-d$_6$, δ): 0.74 (6H, d, J=6.60 Hz), 1.81 (3H, s), 3.28-3.48 (4H, m), 4.88 (1H, 7-plet, J=6.60 Hz), 6.39 (2H, brs), 6.58 (1H, t, J=5.03 Hz), 6.92 (1H, d, J=9.58 Hz), 7.12-7.33 (5H, m), 7.83 (1H, d, J=9.58 Hz), 7.98 (1H, t, J=5.30 Hz)

The following 10 compounds were obtained in a similar manner to that of Example 133.

EXAMPLE 134

6-{5-amino-6-[(2-furylmethyl)amino]-3-phenyl-2-pyrazinyl}-2-isopropyl-3(2H)-pyridazinone
m.p.: 206.5-209° C.
IR (KBr): 3396, 3336, 3251, 3205, 1647, 1577, 1523 cm$^{-1}$
Mass (ESI): 827 (2M+Na)$^+$, 425 (M+Na)$^+$, 403 (M+H)$^+$
$^1$H NMR (CDCl$_3$, δ): 0.85 (6H, d, J=6.62 Hz), 4.69 (2H, d, J=5.26 Hz), 4.96-5.21 (4H, m), 6.29-6.37 (2H, m), 6.91 (1H, d, J=9.54 Hz), 7.18-7.38 (6H, m), 7.76 (1H, d, J=9.54 Hz)

EXAMPLE 135

6-{5-amino-3-phenyl-6-[(2-phenylethyl)amino]-2-pyrazinyl}-2-isopropyl-3(2H)-pyridazinone
m.p.: 204.5-207° C.
IR (KBr): 3394, 3356, 3199, 1647, 1577, 1550, 1523 3369, 3334, 3240, 3197, 1647, 1576, 1554, 1523, 1508 cm$^{-1}$
Mass (ESI): 875 (2M+Na)$^+$, 449 (M+Na)$^+$, 427 (M+H)$^+$
$^1$H NMR (CDCl$_3$, δ): 0.85 (6H, d, J=6.62 Hz), 3.01 (2H, t, J=7.06 Hz), 3.73-3.83 (2H, m), 4.82-5.14 (4H, m), 6.91 (1H, d, J=9.56 Hz), 7.17-7.38 (10H, m), 7.78 (1H, d, J=9.56 Hz)

EXAMPLE 136

6-{5-amino-3-phenyl-6-[(3-phenylpropyl)amino]-2-pyrazinyl}-2-isopropyl-3(2H)-pyridazinone
m.p.: 185.5-187° C.
IR (KBr): 3394, 3356, 3199, 1647, 1577, 1550, 1523 cm$^{-1}$
Mass (ESI): 903 (2M+Na)$^+$, 463 (M+Na)$^+$, 441 (M+H)$^+$
$^1$H NMR (CDCl$_3$, δ): 0.83 (6H, d, J=6.60 Hz), 1.98-2.18 (2H, m), 2.78 (2H, t, J=7.39 Hz), 3.50-3.62 (2H, m), 4.71 (1H, brs), 4.86 (2H, brs), 5.05 (1H, 7-plet, J=6.60 Hz), 6.90 (1H, d, J=9.56 Hz), 7.17-7.35 (10H, m), 7.68 (1H, d, J=9.56 Hz)

EXAMPLE 137

6-[5-amino-6-(cyclohexylamino)-3-phenyl-2-pyrazinyl]-2-isopropyl-3(2H)-pyridazinone
m.p.: 227-228.5° C.
IR (KBr): 3396, 3367, 3340, 3178, 1649, 1579, 1547, 1522 cm$^{-1}$
Mass (ESI): 831 (2M+Na)$^+$, 427 (M+Na)$^+$, 405 (M+H)$^+$
$^1$H NMR (CDCl$_3$, δ): 0.86 (6H, d, J=6.60 Hz), 1.14-2.18 (10H, m), 3.90-4.05 (1H, m), 4.60-4.75 (1H, m), 4.95-5.15 (3H, m), 6.92 (1H, d, J=9.56 Hz), 7.18-7.33 (5H, m), 7.71 (1H, d, J=9.56 Hz)

EXAMPLE 138

6-{5-amino-6-[(1-benzyl-3-pyrrolidinyl)amino]-3-phenyl-2-pyrazinyl}-2-isopropyl-3(2H)-pyridazinone
m.p.: 86-91° C.
IR (KBr): 3363, 3240, 2970, 2792, 1645, 1576, 1550, 1516 cm$^{-1}$
Mass (ESI): 985 (2M+Na)$^+$, 504 (M+Na)$^+$, 482 (M+H)$^+$
$^1$H NMR (CDCl$_3$, δ): 0.84 (3H, d, J=6.60 Hz), 0.86 (3H, d, J=6.60 Hz), 2.35-3.10 (7H, m), 3.75 (2H, s), 4.75 (2H, brs), 4.95-5.25 (2H, 2), 6.89 (1H, d, J=9.54 Hz), 7.18-7.46 (10H, m), 7.69 (1H, d, J=9.54 Hz)

EXAMPLE 139

6-(5-amino-6-anilino-3-phenyl-2-pyrazinyl)-2-isopropyl-3(2H)-pyridazinone
m.p.: >250° C.
IR (KBr): 3371, 3273, 3197, 1643, 1602, 1577, 1552, 1500 cm$^{-1}$
Mass (ESI): 421 (M+Na)$^+$, 399 (M+H)$^+$
$^1$H NMR (DMSO-d$_6$, δ): 0.83 (6H, d, J=6.60 Hz), 4.93 (1H, 7-plet, J=6.60 Hz), 6.80 (2H, brs), 6.90-7.02 (2H, m), 7.20-7.36 (7H, m), 7.67 (1H, d, J=9.57 Hz), 7.81 (2H, d, J=7.82 Hz), 8.47 (1H, s)

EXAMPLE 140

6-[5-amino-6-(4-morpholinyl)-3-phenyl-2-pyrazinyl]-2-isopropyl-3(2H)-pyridazinone
m.p.: 212-214.5° C.
IR (KBr): 3487, 3253, 3114, 2978, 2852, 1664, 1616, 1591, 1535, 1502 cm$^{-1}$ Mass (ESI): 807 (2M+Na)⁺, 415 (M+Na)⁺, 393 (M+H)⁺
¹H NMR (CDCl₃, δ): 0.83 (6H, d, J=6.60 Hz), 3.28 (4H, t, J=4.67 Hz), 3.90 (4H, t, J=4.67 Hz), 4.89 (2H, brs), 5.06 (1H, 7-plet, J=6.60 Hz), 6.94 (1H, d, J=9.58 Hz), 7.24-7.36 (5H, m), 7.79 (1H, d, J=9.58 Hz)

EXAMPLE 141

6-[5-amino-3-phenyl-6-(1-pyrrolidinyl)-2-pyrazinyl]-2-isopropyl-3(2H)-pyridazinone m.p.: 192-194.5° C.

IR (KBr): 3487, 3269, 3122, 2964, 1657, 1622, 1589, 1533, 1504 cm⁻¹

Mass (ESI): 399 (M+Na)⁺, 377 (M+H)⁺

¹H NMR (CDCl₃, δ): 0.84 (6H, d, J=6.60 Hz), 1.95-2.05 (4H, m), 3.55-3.65 (4H, m), 4.91 (2H, brs), 5.06 (1H, 7-plet), 6.91 (1H, d, J=9.55 Hz), 7.18-7.37 (5H, m), 7.79 (1H, d, J=9.55 Hz)

EXAMPLE 142

6-{5-amino-3-phenyl-6-[4-(2-pyridyl)-1-piperazinyl]-2-pyrazinyl}-2-isopropyl-3(2H)-pyridazinone m.p.: 163-165° C.

IR (KBr): 3458, 3292, 3182, 1654, 1612, 1585, 1504 cm⁻¹

Mass (ESI): 491 (M+Na)⁺, 469 (M+H)⁺

¹H NMR (CDCl₃, δ): 0.83 (6H, d, J=6.62 Hz), 3.38-3.44 (4H, m), 3.73-3.79 (4H, m), 4.92 (2H, brs), 5.06 (1H, 7-plet), 6.66-6.78 (2H, m), 6.93 (1H, d, J=9.56 Hz), 7.24-7.36 (5H, m), 7.51-7.61 (1H, m), 7.78 (1H, d, J=9.56 Hz), 8.22-8.26 (1H, m)

EXAMPLE 143

6-{5-amino-6-[benzyl(2-hydroxyethyl)amino]-3-phenyl-2-pyrazinyl}-2-methyl-3(2H)-pyridazinone m.p.: 210-212° C.

IR (KBr): 3417, 3323, 3161, 1653, 1587, 1537 cm⁻¹

Mass (ESI): 879 (2M+Na)⁺, 451 (M+Na)⁺, 429 (M+H)⁺

¹H NMR (CDCl₃, δ): 3.57 (3H, s), 4.67 (2H, s), 6.77 (1H, d, J=9.60 Hz), 7.15 (1H, d, J=9.60 Hz)

EXAMPLE 144

A mixture of 6-(5-amino-6-bromo-3-phenyl-2-pyrazinyl)-2-methyl-3(2H)-pyridazinone (150 mg) and benzylamine (0.138 ml) in DMA (0.3 ml) was heated at 120-125° C. for 50 hours. After addition of water (4 ml), an aqueous layer was removed by decantation to give a residue. The residue was dissolved in CHCl₃, dried over MgSO₄, concentrated under reduced pressure and purified by column chromatography on silica gel. By elution with a mixture of n-hexane and EtOAc (60:40 v/v) was obtained 6-[5-amino-6-(dimethylamino)-3-phenyl-2-pyrazinyl]-2-methyl-3(2H)-pyridazinone as a solid (83 mg) and by elution with a mixture of n-hexane and EtOAc (20:80 v/v) was obtained 6-[5-amino-6-(benzylamino)-3-phenyl-2-pyrazinyl]-2-methyl-3 (2H)-pyridazinone as a solid (48 mg).

6-[5-amino-6-(benzylamino)-3-phenyl-2-pyrazinyl]-2-methyl-3(2H)-pyridazinone as a solid m.p.: >250° C.

IR (KBr): 3433, 3344, 3188, 1647, 1576, 1518 cm⁻¹

Mass (ESI): 791 (2M+Na)⁺, 407 (M+Na)⁺, 385 (M+H)⁺

¹H NMR (DMSO-d₆, δ): 3.30 (3H, s), 4.62 (2H, d, J=5.30 Hz), 6.50 (2H, brs), 6.86 (1H, d, J=9.60 Hz), 7.00 (1H, t, J=5.30 Hz), 7.19-7.55 (10H, m), 7.65 (1H, d, J=9.60 Hz)

6-[5-amino-6-(dimethylamino)-3-phenyl-2-pyrazinyl]-2-methyl-3(2H)-pyridazinone m.p.: 150-152° C.

IR (KBr): 3423, 3400, 3313, 3205, 1647, 1620, 1577, 1539, 1504 cm⁻¹

Mass (ESI): 667 (2M+Na)⁺, 345 (M+Na)⁺, 323 (M+H)⁺

¹H NMR (CDCl₃, δ): 2.91 (6H, s), 3.51 (3H, s), 4.88 (2H, brs), 6.84 (1H, d, J=9.60 Hz), 7.26-7.45 (5H, m), 7.54 (1H, d, J=9.60 Hz)

The following compounds were obtained in a similar manner to that of Example 144.

EXAMPLE 145

6-{5-amino-6-[(4-methoxybenzyl)amino]-3-phenyl-2-pyrazinyl}-2-methyl-3(2H)-pyridazinone and 6-[5-amino-6-(dimethylamino)-3-phenyl-2-pyrazinyl]-2-methyl-3(2H)-pyridazinone 6-[5-amino-6-[(4-methoxybenzyl)amino]-3-phenyl-2-pyrazinyl}-2-methyl-3(2H)-pyridazinone m.p.: >250° C.

IR (KBr): 3396, 3309, 3163, 1651, 1576, 1549, 1514 cm⁻¹

Mass (ESI): 851 (2M+Na)⁺, 437 (M+Na)⁺, 415 (M+H)⁺

¹H NMR (DMSO-d₆, δ): 3.32 (3H, s), 3.73 (3H, s), 4.54 (2H, d, J=5.11 Hz), 6.47 (2H, brs), 6.84-6.94 (4H, m), 7.18-7.31 (5H, m), 7.33 (2H, d, J=8.61 Hz), 7.55 (1H, d, J=9.58 Hz)

6-[5-amino-6-(dimethylamino)-3-phenyl-2-pyrazinyl]-2-methyl-3(2H)-pyridazinone m.p.: 150-152° C.

IR (KBr): 3423, 3400, 3313, 3205, 1647, 1620, 1577, 1539, 1504 cm⁻¹

Mass (ESI): 667 (2M+Na)⁺, 345 (M+Na)⁺, 323 (M+H)⁺

¹H NMR (CDCl₃, δ): 2.91 (6H, s), 3.51 (3H, s), 4.88 (2H, brs), 6.84 (1H, d, J=9.60 Hz), 7.26-7.45 (5H, m), 7.54 (1H, d, J=9.60 Hz)

EXAMPLE 146

6-{5-amino-3-phenyl-6-[(2-pyridylmethyl)amino]-2-pyrazinyl}-2-methyl-3(2H)-pyridazinone and 6-[5-amino-6-(dimethylamino)-3-phenyl-2-pyrazinyl]-2-methyl-3(2H)-pyridazinone 6-{5-amino-3-phenyl-6-[(2-pyridylmethyl)amino]-2-pyrazinyl}-2-methyl-3(2H)-pyridazinone m.p.: >250° C.

IR (KBr): 3433, 3359, 3192, 1647, 1576, 1554, 1522 cm⁻¹

Mass (ESI): 795 (2M+Na)⁺, 408 (M+Na)⁺, 386 (M+H)⁺

¹H NMR (CDCl₃, δ): 3.28 (3H, s), 4.71 (2H, d, J=5.40 Hz), 6.55 (2H, brs), 6.83 (1H, d, J=9.58 Hz), 7.13-7.32 (7H, m), 7.39-7.46 (2H, m), 7.71-7.81 (1H, m), 8.54 (1H, d, J=5.10 Hz)

6-[5-amino-6-(dimethylamino)-3-phenyl-2-pyrazinyl]-2-methyl-3(2H)-pyridazinone m.p.: 150-152° C.

IR (KBr): 3423, 3400, 3313, 3205, 1647, 1620, 1577, 1539, 1504 cm⁻¹

Mass (ESI): 667 (2M+Na)⁺, 345 (M+Na)⁺, 323 (M+H)⁺

¹H NMR (CDCl₃, δ): 2.91 (6H, s), 3.51 (3H, s), 4.88 (2H, brs), 6.84 (1H, d, J=9.60 Hz), 7.26-7.45 (5H,), 7.54 (1H, d, J=9.60 Hz)

EXAMPLE 147

To a suspension of NaH (60% in oil suspension) (77.7 mg) in dioxane (0.6 ml) was added 1H-pyrrole (0.161 ml) and the mixture was stirred at 25-30° C. for 30 minutes. After addition of 6-(5-amino-6-bromo-3-phenyl-2-pyrazinyl)-2-isopropyl-3(2H)-pyridazinone (150 mg), the mixture was heated at 100-105° C. for 2 hours. A mixture of water and chloroform was added to the reaction mixture. An organic layer was collected, dried over MgSO₄, concentrated under reduced pressure and purified by column chromatography on silica gel eluting with a mixture of n-hexane and EtOAc (75:25 v/v) to give a solid. The solid was crystallized from a mixture of IPE and n-hexane to give 6-[5-amino-3-phenyl-6-(1H-pyrrol-1-yl)-2-pyrazinyl]-2-isopropyl-3(2H)-pyridazinone (38 mg).

m.p.: 132-136° C.
IR (KBr): 3475, 3280, 3193, 3167, 3124, 2862, 1693, 1660, 1624, 1589, 1558, 1506 cm⁻¹
Mass (ESI): 395 (M+Na)⁺
¹H NMR (CDCl₃, δ): 0.84 (6H, d, J=6.60 Hz), 5.07 (1H, 7-plet, J=6.60 Hz), 5.14 (2H, brs), 6.43-6.56 (2H, m), 6.94 (1H, d, J=9.60 Hz), 7.30-7.44 (7H, m), 7.80 (1H, d, J=9.60 Hz)

EXAMPLE 148

6-[5-amino-3-phenyl-6-(1H-pyrrol-1-yl)-2-pyrazinyl]-2-methyl-3(2H)-pyridazinone

The title compound was obtained in a similar manner to that of Example 147.

m.p.: 202-205° C.
IR (KBr): 3367, 3336, 3303, 3273, 3193, 1695, 1657, 1624, 1585, 1560, 1508 cm⁻¹
Mass (ESI): 711 (2M+Na)⁺, 367 (M+Na)⁺
¹H NMR (CDCl₃, δ): 3.53 (3H, s), 5.19 (2H, brs), 6.43-6.46 (2H, m), 6.86 (1H, d, J=9.60 Hz), 7.28-7.47 (7H, m), 7.53 (1H, d, J=9.60 Hz)

EXAMPLE 149

To a suspension of NaH (60% in oil suspension) (23.3 mg) in 1,2-dimethyl-2-imidazolidinone (0.3 ml) was added 1H-pyrazole (42.3 mg) and the mixture was stirred at 25-30° C. for 30 minutes. After addition of 6-(5-amino-6-bromo-3-phenyl-2-pyrazinyl)-2-isopropyl-3(2H)-pyridazinone (150 mg), the mixture was heated at 120-125° C. for 15 hours. To the reaction mixture was added water (3 ml) to give a precipitate. The precipitate was dissolved in CHCl₃, dried over MgSO₄ and concentrated under reduced pressure to give a solid. The solid was suspended in acetone and collected by filtration to give 6-[5-amino-3-phenyl-6-(1H-pyrazol-1-yl)-2-pyrazinyl]-2-isopropyl-3(2H)-pyridazinone (66 mg).

m.p.: 210-212° C.
IR (KBr): 3386, 3342, 3261, 3143, 2979, 1660, 1616, 1591, 1508 cm⁻¹
Mass (ESI): 769 (2M+Na)⁺, 396 (M+Na)⁺, 374 (M+H)⁺
¹H NMR (CDCl₃, δ): 0.87 (6H, d, J=6.64 Hz), 5.09 (1H, 7-plet, J=6.64 Hz), 6.53-6.57 (1H, m), 6.97 (1H, d, J=9.60 Hz), 7.01 (2H, brs), 7.30-7.44 (5H, m), 7.72-7.79 (2H, m), 8.63 (1H, d, J=3.16 Hz)

¹H NMR (DMSO-d₆, δ): 0.75 (6H, d, J=6.60 Hz), 4.90 (1H, 7-plet, J=6.60 Hz), 6.68-6.71 (1H, m), 6.99 (1H, d, J=9.60 Hz), 7.32-7.42 (5H, m), 7.83 (2H, brs), 7.94-7.96 (1H, m), 8.05 (1H, d, J=9.60 Hz), 8.79-8.82 (1H, m)

The following compounds were obtained in a similar manner to that of Example 149.

EXAMPLE 150

6-[5-amino-6-(1H-imidazol-1-yl)-3-phenyl-2-pyrazinyl]-2-isopropyl-3(2H)-pyridazinone m.p.: >250° C.
IR (KBr): 3303, 3170, 1643, 1585, 1560, 1508 cm⁻¹
Mass (ESI): 769 (2M+Na)⁺, 396 (M+Na)⁺, 374 (M+H)⁺
¹H NMR (CDCl₃, δ): 0.84 (6H, d, J=6.65 Hz), 5.08 (1H, 7-plet, J=6.65 Hz), 5.21 (2H, brs), 6.95 (1H, d, J=9.60 Hz), 7.30-7.43 (6H, m), 7.53-7.55 (1H, m), 7.75 (1H, d, J=9.60 Hz), 8.24 (1H, s)

EXAMPLE 151

6-[5-amino-3-phenyl-6-(1H-1,2,4-triazol-1-yl)-2-pyrazinyl]-2-isopropyl-3(2H)-pyridazinone m.p.: 240-241.5° C.
IR (KBr): 3446, 3286, 3161, 1651, 1581, 1533, 1504 cm⁻¹
Mass (ESI): 771 (2M+Na)⁺, 397 (M+Na)⁺
¹H NMR (CDCl₃, δ): 0.87 (6H, d, J=6.62 Hz), 5.10 (1H, 7-plet, J=6.62 Hz), 6.82 (2H, brs), 6.99 (1H, d, J=9.54 Hz), 7.33-7.45 (5H,), 7.72 (1H, d, J=9.54 Hz), 8.20 (1H, s), 9.21 (1H, s)

EXAMPLE 152

6-[5-amino-6-(1H-benzimidazol-1-yl)-3-phenyl-2-pyrazinyl]-2-isopropyl-3(2H)-pyridazinone m.p.: >250° C.
IR (KBr): 3454, 3271, 3143, 3114, 3099, 2976, 1658, 1626, 1587, 15556, 1506 cm⁻¹
Mass (ESI): 869 (2M+Na)⁺, 446 (M+Na)⁺, 424 (M+H)⁺
¹H NMR (CDCl₃, δ): 0.85 (6H, d, J=6.60 Hz), 5.08 (1H, 7-plet, J=6.60 Hz), 5.20 (2H, brs), 6.93 (1H, d, J=9.60 Hz), 7.36-7.74 (8H, m), 7.74 (1H, d, J=9.60 Hz), 7.86-7.94 (1H, m), 8.40 (1H, s)

EXAMPLE 153

6-[5-amino-3-phenyl-6-(1H-pyrazol-1-yl)-2-pyrazinyl]-2-methyl-3(2H)-pyridazinone m.p.: 187-189.5° C.
IR (KBr): 3404, 3383, 3261, 3153, 1657, 1620, 1587, 1518, cm⁻¹
Mass (ESI): 368 (M+Na)⁺, 346 (M+H)⁺
¹H NMR (CDCl₃, δ): 3.56 (3H, s), 6.53-6.56 (1H, m), 6.88 (1H, d, J=9.60 Hz), 7.00 (2H, brs), 7.35-7.46 (5H, m), 7.50 (1H, d, J=9.60 Hz), 7.78 (1H, d, J=2.06 Hz), 8.64 (1H, d, J=3.16 Hz)

EXAMPLE 154

6-[5-amino-6-(1H-imidazol-1-yl)-3-phenyl-2-pyrazinyl]-2-methyl-3(2H)-pyridazinone m.p.: >250° C.
IR (KBr): 3357, 3307, 3159, 1645, 1587, 1560, 1508 cm⁻¹
Mass (ESI): 713 (2M+Na)⁺, 368 (M+Na)⁺, 346 (M+H)⁺

¹H NMR (CDCl₃, δ): 3.55 (3H, s), 5.21 (2H, brs), 6.86 (1H, d, J=9.70 Hz), 7.30 (1H, s), 7.40-7.53 (7H, m), 8.17 (1H, s)

EXAMPLE 155

6-[5-amino-3-phenyl-6-(1H-1,2,4-triazol-1-yl)-2-pyrazinyl]-2-methyl-3(2H)-pyridazinone
m.p.: >250° C.
IR (KBr): 3425, 3294, 3099, 1660, 1649, 1614, 1601, 1579, 1508 cm⁻¹
Mass (ESI): 369 (M+Na)⁺
¹H NMR (CDCl₃, δ): 3.58 (3H, s), 6.74 (2H, brs), 6.89 (1H, d, J=9.56 Hz), 7.35-7.48 (6H, m), 8.20 (1H, s), 9.23 (1H, s)

EXAMPLE 156

6-[5-amino-6-(1H-benzimidazol-1-yl)-3-phenyl-2-pyrazinyl]-2-methyl-3(2H)-pyridazinone
m.p.: >250° C.
IR (KBr): 3317, 3176, 1670, 1655, 1587, 1556, 1504 cm⁻¹
Mass (ESI): 813 (2M+Na)⁺, 418 (M+Na)⁺, 396 (M+H)⁺
¹H NMR (CDCl₃, δ): 3.54 (3H, s), 5.26 (2H, brs), 6.85 (1H, d, J=9.58 Hz), 7.39-7.56 (9H, m), 7.88-7.93 (1H, m), 8.48 (1H, s)

EXAMPLE 157

A suspension of 6-[5-amino-6-(methylsulfonyl)-3-phenyl-2-pyrazinyl]-2-isopropyl-3(2H)-pyridazinone (205 mg) and sodium methoxide (57.7 mg) in MeOH (0.6 m) was refluxed for 24 hours. Water (3 ml) was added to the reaction mixture to give a precipitate. The precipitate was collected by filtration and purified by column chromatography on silica gel eluting with a mixture of n-hexane and EtOAc (60:40 v/v) to give a solid. The solid was suspended in acetone and collected by filtration to give 6-(5-amino-6-methoxy-3-phenyl-2-pyrazinyl)-2-isopropyl-3(2H)-pyridazinone (154 mg).
m.p.: 211-214° C. (acetone-n-hexane)
IR (KBr): 3464, 3323, 1660, 1612, 1585, 1520 cm⁻¹
Mass (ESI): 729 (2M+Na)⁺, 376 (M+Na)⁺, 354 (M+H)⁺
¹H NMR (CDCl₃, δ): 0.84 (6H, d, J=6.60 Hz), 2.70 (3H, s), 5.00 (2H, brs), 5.08 (1H, 7-plet, J=6.60 Hz), 6.94 (1H, d, J=9.58 Hz), 7.26-7.37 (5H, m), 7.79 (1H, d, J=9.58 Hz)

EXAMPLE 158

To a suspension of NaH (60% in oil suspension) (31.1 mg) in DMA (0.6 ml) was added 4-fluorophenol (87.3 mg) and the mixture was stirred at 25-30° C. for 30 minutes. 6-[5-Amino-6-(methylsulfonyl)-3-phenyl-2-pyrazinyl]-2-isopropyl-3(2H)-pyridazinone (150 mg) was added and the mixture was heated at 100-105° C. for 15 hours. After addition of 0.1N HCl (3 ml), an aqueous layer was removed by decantation to give a residue. The residue was purified by column chromatography on silica gel eluting with a mixture of n-hexane and EtOAc (60:40 v/v) to give a solid. The solid was crystallized from a mixture of acetone and n-hexane to give 6-[5-amino-6-(4-fluorophenoxy)-3-phenyl-2-pyrazinyl]-2-isopropyl-3(2H)-pyridazinone (70 mg)
m.p.: 173-175° C.
IR (KBr): 3483, 3294, 3163, 1660, 1626, 1587, 1504 cm⁻¹
Mass (ESI): 857 (2M+Na)⁺, 440 (M+Na)⁺, 418 (M+H)⁺
¹H NMR (CDCl₃, δ): 0.81 (6H, d, J=6.60 Hz), 5.03 (1H, 7-plet, J=6.60 Hz), 5.35 (2H, brs), 6.79 (1H, d, J=9.58 Hz), 7.08-7.40 (10H, m)

EXAMPLE 159

6-{5-amino-6-[(4-fluorophenyl)thio]-3-phenyl-2-pyrazinyl}-2-isopropyl-3(2H)-pyridazinone
The title compound was obtained in a similar manner to that of Example 158.
m.p.: 148-150° C.
IR (KBr): 3275, 3138, 1653, 1624, 1583, 1523 cm⁻¹
Mass (ESI): 889 (2M+Na)⁺, 456 (M+Na)⁺, 434 (M+H)⁺
¹H NMR (CDCl₃, δ): 0.80 (6H, d, J=6.60 Hz), 5.03 (1H, 7-plet, J=6.60 Hz), 5.28 (2H, brs), 6.83 (1H, d, J=9.60 Hz), 7.08-7.59 (10H, m)

EXAMPLE 160

In a sealed tube, NaH (60% in oil suspension) (31.1 mg) was added 2-propanol (0.6 ml) and the mixture was stirred at 25-30° C. for 30 minutes. 6-[5-Amino-6-(methylsulfonyl)-3-phenyl-2-pyrazinyl]-2-isopropyl-3(2H)-pyridazinone (150 mg) was added and the mixture was heated at 100-105° C. for 15 hours. After addition of 0.1N HCl (3 ml) was added to the mixture and an aqueous layer was removed by decantation to give a residue. The residue was purified by column chromatography on silica gel eluting with a mixture of n-hexane and EtOAc (70:30 v/v) to give a solid. The solid was crystallized from a mixture of acetone and n-hexane to give 6-(5-amino-6-isopropoxy-3-phenyl-2-pyrazinyl)-2-isopropyl-3(2H)-pyridazinone (102 mg).
m.p.: 198-200° C.
IR (KBr): 3491, 3267, 3143, 2979, 1666, 1620, 1591, 1508 cm⁻¹
Mass (ESI): 753 (2M+Na)⁺, 388 (M+Na)⁺, 366 (M+H)⁺
¹H NMR (CDCl₃, δ): 0.71 (6H, d, J=6.60 Hz), 0.85 (6H, d, J=6.60 Hz), 5.07 (1H, 7-plet, J=6.60 Hz), 5.23 (2H, brs), 5.41 (1H, 7-plet, J=6.60 Hz), 6.91 (1H, d, J=9.56 Hz), 7.22-7.39 (5H, m), 7.66 (1H, d, J=9.56 Hz)

EXAMPLE 161

To a suspension of NaH (60% in oil suspension) (31.1 mg) in DMA (0.6 ml) was added cyclohexanol (0.081 ml) and the mixture was stirred at 25-30° C. for 30 minutes. 6-[5-Amino-6-(methylsulfonyl)-3-phenyl-2-pyrazinyl]-2-isopropyl-3(2H)-pyridazinone (150 mg) was added and the mixture was heated at 100-105° C. for 15 hours. After addition of 0.1N HCl (3 ml) was added to the mixture and an aqueous layer was removed by decantation to give a residue. The residue was dissolved in CHCl₃, dried over MgSO₄, concentrated under reduced pressure and purified by column chromatography on silica gel eluting with a mixture of n-hexane and EtOAc (60:40 v/v) to give a solid. The solid was crystallized from a mixture of acetone and n-hexane (60:40 v/v) to give 6-[5-amino-6-(cyclohexyloxy)-3-phenyl-2-pyrazinyl]-2-isopropyl-3(2H)-pyridazinone (55 mg).
m.p.: 161-163° C.
IR (KBr): 3489, 3276, 3143, 2935, 1664, 1618, 1591 cm⁻¹
Mass (ESI): 833 (2M+Na)⁺, 428 (M+Na)⁺, 406 (M+H)⁺
¹H NMR (CDCl₃, δ): 0.86 (6H, d, J=6.60 Hz), 1.33-2.18 (10H, m), 5.00-5.29 (4H, m), 6.90 (1H, d, J=9.60 Hz), 7.22-7.40 (5H, m), 7.62 (1H, d, J=9.60 Hz)

The following 3 compounds were obtained in a similar manner to that of Example 161.

EXAMPLE 162

6-[5-amino-6-(benzyloxy)-3-phenyl-2-pyrazinyl]-2-isopropyl-3(2H)-pyridazinone m.p.: 118-120° C.

IR (KBr): 3479, 3280, 3143, 1664, 1626, 1508 cm$^{-1}$

Mass (ESI): 436 (M+Na)$^+$, 414 (M+H)$^+$ $^1$H NMR (CDCl$_3$, δ): 0.87 (6H, d, J=6.62 Hz), 5.08 (1H, 7-plet, J=6.62 Hz), 5.15 (2H, brs), 5.49 (2H, s), 6.91 (1H, d, J=9.56 Hz), 7.22-7.51 (10H, m), 7.65 (1H, d, J=9.56 Hz)

EXAMPLE 163

6-[5-amino-3-phenyl-6-(2-pyridylmethoxy)-2-pyrazinyl]-2-isopropyl-3(2H)-pyridazinone m.p.: 150-151° C.

IR (KBr): 3309, 1660, 1626, 1577 cm$^{-1}$

Mass (ESI): 437 (M+Na)$^+$, 415 (M+H)$^+$ $^1$H NMR (CDCl$_3$, δ): 0.85 (6H, d, J=6.62 Hz), 5.06 (1H, 7-plet, J=6.62 Hz), 5.23 (2H, brs), 5.64 (2H, s), 6.88 (1H, d, J=9.56 Hz), 7.22-7.34 (6H, m), 7.49 (1H, d, J=7.82 Hz), 7.59 (1H, d, J=9.56 Hz), 7.72-7.82 (1H, m), 8.66 (1H, d, J=5.00 Hz)

EXAMPLE 164

6-[5-amino-6-(2-furylmethoxy)-3-phenyl-2-pyrazinyl]-2-isopropyl-3(2H)-pyridazinone m.p.: 172-174° C.

IR (KBr): 3479, 3276, 3147, 1664, 1624, 1591, 1508 cm$^{-1}$

Mass (ESI): 426 (M+Na)$^+$, 404 (M+H)$^+$ $^1$H NMR (CDCl$_3$, δ): 0.87 (6H, d, J=6.62 Hz), 5.09 (1H, 7-plet, J=6.62 Hz), 5.15 (2H, brs), 5.45 (2H, s), 6.40-6.43 (1H, m), 6.50-6.52 (1H, m), 6.93 (1H, d, J=9.56 Hz), 7.22-7.35 (5H, m), 7.47-7.49 (1H, m), 7.71 (1H, d, J=9.56 Hz)

EXAMPLE 165

To a suspension of NaH (60% in oil suspension) (31.1 mg) in 1,2-dimethyl-2-imidazolidinone (0.6 ml) was added to 1-butanol (0.0716 ml) and the mixture was stirred at 25-30° C. for 30 minutes. 6-[5-Amino-6-(methylsulfonyl)-3-phenyl-2-pyrazinyl]-2-isopropyl-3(2H)-pyridazinone (150 mg) was added and the mixture was heated at 100-105° C. for 15 hours. After addition of 0.1N HCl (3 ml) was added to the mixture and a precipitate was collected by filtration. The precipitate was dissolved in CHCl$_3$, dried over MgSO$_4$, concentrated under reduced pressure and purified by column chromatography on silica gel eluting with a mixture of n-hexane and EtOAc (80:20 v/v) to give a solid. The solid was suspended in hexane and collected by filtration to give 6-(5-amino-6-butoxy-3-phenyl-2-pyrazinyl)-2-isopropyl-3 (2H)-pyridazinone (83 mg).

m.p.: 130-131.5° C.

IR (KBr): 3489, 3276, 3147, 2954, 1666, 1622, 1593, 1510 cm$^{-1}$

Mass (ESI): 781 (2M+Na)$^+$, 402 (M+Na)$^+$, 380 (M+H)$^+$ $^1$H NMR (CDCl$_3$, δ): 0.85 (6H, d, J=6.60 Hz), 1.01 (3H, t, J=7.29 Hz), 1.42-1.63 (2H, m), 1.76-1.91 (2H, m), 4.45 (2H, t, J=6.54 Hz), 5.07 (1H, 7-plet, J=6.60 Hz), 5.18 (2H, brs), 6.92 (1H, d, J=9.56 Hz), 7.21-7.38 (5H, m), 7.69 (1H, d, J=9.56 Hz)

The following 8 compounds were obtained in a similar manner to that of Example 165.

EXAMPLE 166

6-[5-amino-6-(2-methoxyethoxy)-3-phenyl-2-pyrazinyl]-2-isopropyl-3(2H)-pyridazinone m.p.: 128-130° C.

IR (KBr): 3487, 3278, 3145, 1666, 1620, 1591, 1508 cm$^{-1}$

Mass (ESI): 785 (2M+Na)$^+$, 404 (M+Na)$^+$, 382 (M+H)$^+$ $^1$H NMR (CDCl$_3$, δ): 0.85 (6H, d, J=6.60 Hz), 3.46 (3H, s), 3.79-3.84 (2H, m), 4.59-4.65 (2H, m), 5.07 (1H, 7-plet, J=6.60 Hz), 5.22 (2H, brs), 6.91 (1H, d, J=9.58 Hz), 7.22-7.42 (5H, m), 7.66 (1H, d, J=9.58 Hz)

EXAMPLE 167

6-[5-amino-6-(2-tert-butoxyethoxy)-3-phenyl-2-pyrazinyl]-2-isopropyl-3(2H)-pyridazinone m.p.: 163-165° C.

IR (KBr): 3483, 3450, 3423, 3280, 2974, 1666, 1620, 1591 cm$^{-1}$

Mass (ESI): 446 (M+Na)$^+$, 424 (M+H)$^+$ $^1$H NMR (CDCl$_3$, δ): 0.85 (6H, d, J=6.60 Hz), 1.25 (9H, s), 3.77 (2H, t, J=5.12 Hz), 4.56 (2H, t, J=5.12 Hz), 5.10 (1H, 7-plet, J=6.60 Hz), 5.18 (2H, brs), 6.91 (1H, d, J=9.56 Hz), 7.24-7.34 (5H, m), 7.69 (1H, d)

EXAMPLE 168

6-{5-amino-6-[2-(benzyloxy)ethoxy]-3-phenyl-2-pyrazinyl}-2-isopropyl-3(2H)-pyridazinone m.p.: 120-122° C.

IR (KBr): 3483, 3463, 3327, 3134, 1655, 1624, 1585 cm$^{-1}$

Mass (ESI): 480 (M+Na)$^+$, 458 (M+H)$^+$ $^1$H NMR (CDCl$_3$, δ): 0.85 (6H, d, J=6.60 Hz), 3.90 (2H, t, J=9.52 Hz), 4.61-4.66 (4H, m), 5.06 (1H, 7-plet, J=6.60 Hz), 5.13 (2H, brs), 6.89 (1H, d, J=9.54 Hz), 7.21-7.38 (10H, m), 7.62 (1H, d, J=9.54 Hz)

EXAMPLE 169

6-{5-amino-6-[4-(benzyloxy)butoxy]-3-phenyl-2-pyrazinyl}-2-isopropyl-3(2H)-pyridazinone m.p.: 96.5-97.5° C.

IR (KBr): 3494, 3278, 3149, 2951, 1651, 1622, 1581, 1504 cm$^{-1}$

Mass (ESI): 508 (M+Na)$^+$, 486 (M+H)$^+$ $^1$H NMR (CDCl$_3$, δ): 0.85 (6H, d, J=6.60 Hz), 1.74-2.18 (4H, m), 3.57 (2H, t, J=6.13 Hz), 4.47 (2H, t, J=6.13 Hz), 4.53 (2H, s), 5.06 (1H, 7-plet, J=6.60 Hz), 5.15 (2H, brs), 6.89 (1H, d, J=9.60 Hz), 7.22-7.35 (10H, m), 7.66 (1H, d, J=9.60 Hz)

EXAMPLE 170

6-{5-amino-6-[2-(dimethylamino)ethoxy]-3-phenyl-2-pyrazinyl}-2-isopropyl-3(2H)-pyridazinone m.p.: 136-137.5° C.

IR (KBr): 3487, 3456, 3273, 3134, 2978, 1660, 1635, 1591 cm$^{-1}$

Mass (ESI): 417 (M+Na)$^+$, 395 (M+H)$^+$ $^1$H NMR (CDCl$_3$, δ): 0.86 (6H, d, J=6.62 Hz), 2.41 (6H, s), 2.85 (2H, t, J=5.62 Hz), 4.56 (2H, t, J=5.62 Hz), 5.07 (1H, 7-plet, J=6.62 Hz), 5.37 (2H, brs), 6.90 (1H, d, J=9.56 Hz), 7.24-7.34 (5H, m), 7.67 (1H, d, J=9.56 Hz)

EXAMPLE 171

6-[5-amino-3-phenyl-6-(2,2,2-trifluoroethoxy)-2-pyrazinyl]-2-isopropyl-3(2H)-pyridazinone m.p.: 233-235° C.

IR (KBr): 3492, 3278, 3155, 2974, 1666, 1624, 1593, 1510 cm$^{-1}$

Mass (ESI): 833 (2M+Na)$^+$, 428 (M+Na)$^+$, 406 (M+H)$^+$ $^1$H NMR (CDCl$_3$, δ): 0.85 (6H, d, J=6.60 Hz), 4.87 (2H, q, J=8.32 Hz), 5.08 (1H, 7-plet, J=6.60 Hz), 5.22 (2H, brs), 6.93 (1H, d, J=9.62 Hz), 7.27-7.39 (5H, m), 7.61 (1H, d, J=9.62 Hz)

EXAMPLE 172

6-{5-amino-6-[2-(4-morpholinyl)ethoxy]-3-phenyl-2-pyrazinyl}-2-isopropyl-3(2H)-pyridazinone m.p.: 139-143° C.

IR (KBr): 3483, 3450, 3305, 3195-3105, 2964, 1657, 1635, 1589 cm$^{-1}$

Mass (ESI): 459 (M+Na)$^+$, 437 (M+H)$^+$ $^1$H NMR (CDCl$_3$, δ): 0.86 (6H, d, J=6.60 Hz), 2.60-2.72 (4H, m), 2.92 (2H, t, J=5.72 Hz), 3.69-3.81 (4H, m), 4.59 (2H, t, J=5.72 Hz), 5.07 (1H, 7-plet, J=6.60 Hz), 5.29 (2H, brs), 6.90 (1H, d, J=9.58 Hz), 7.22-7.41 (5H, m), 7.65 (1H, d, J=9.58 Hz)

EXAMPLE 173

2-(2-{β-amino-6-(1-isopropyl-6-oxo-1,6-dihydro-3-pyridazinyl)-5-phenyl-2-pyrazinyl]oxy}ethyl)-1H-isoindole-1,3(2H)-dione m.p.: 208-210° C.

IR (KBr): 3458, 3437, 3282, 3155, 1768, 1718, 1666, 1626, 1589 cm$^{-1}$

Mass (ESI): 519 (M+Na)$^+$, 497 (M+H)$^+$ $^1$H NMR (CDCl$_3$, δ): 0.82(6H, d, J=6.62 Hz), 4.20 (2H, t, J=5.10 Hz), 4.66 (2H, t, J=5.10 Hz), 5.04 (1H, 7-plet, J=6.62 Hz), 5.23 (2H, brs), 6.89 (1H, d, J=9.60 Hz), 7.22-7.32 (5H, m), 7.65 (1H, d, J=9.60 Hz), 7.67-7.77 (2H, m), 7.82-7.88 (2H, m)

EXAMPLE 174

To a suspension of NaH (60% in oil suspension) (31.1 mg) in 1,2-dimethyl-2-imidazolidinone (0.6 ml) was added 2-phenylethanol (0.094 ml) and the mixture was stirred at 25-30° C. for 30 minutes. 6-[5-Amino-6-(methylsulfonyl)-3-phenyl-2-pyrazinyl]-2-isopropyl-3(2H)-pyridazinone (150 mg) was added and the mixture was heated at 100-105° C. for 15 hours. To the mixture was added 0.1N HCl (3 ml) and an aqueous layer was removed by decantation to give a residue. The residue was dissolved in CHCl$_3$, dried over MgSO$_4$, concentrated under reduced pressure and purified by column chromatography on silica gel. By elution with a mixture of n-hexane and EtOAc (60:40 v/v) was obtained 6-[5-amino-3-phenyl-6-(2-phenylethoxy)-2-pyrazinyl]-2-isopropyl-3(2H)-pyridazinone as a solid (9 mg). By elution with a mixture of MeOH and EtOAc (1:99 v/v) was obtained 6-(5-amino-6-oxo-3-phenyl-1,6-dihydro-2-pyrazinyl)-2-isopropyl-3(2H)-pyridazinone as a solid (89 mg).

6-[5-amino-3-phenyl-6-(2-phenylethoxy)-2-pyrazinyl]-2-isopropyl-3(2H)-pyridazinone m.p.: 173-176° C.

IR (KBr): 3477, 3448, 3406, 3280, 1662, 1620, 1591, 1506 cm$^{-1}$

Mass (ESI): 877 (2M+Na)$^+$, 450 (M+Na)$^+$, 428 (M+H)$^+$ $^1$H NMR (CDCl$_3$, δ): 0.85 (6H, d, J=6.60 Hz), 3.17 (2H, t, J=6.98 Hz), 4.67 (2H, t, J=6.98 Hz), 5.07 (1H, 7-plet, J=6.60 Hz), 5.23 (2H, brs), 6.91 (1H, d, J=9.56 Hz), 7.23-7.39 (10H, m), 7.66 (1H, d, J=9.56 Hz)

6-(5-amino-6-oxo-3-phenyl-1,6-dihydro-2-pyrazinyl)-2-isopropyl-3(2H)-pyridazinone m.p.: >250° C. (DMSO-H$_2$O)

IR (KBr): 3431, 3315, 1664, 1645, 1608, 1585, 1522 cm$^{-1}$

Mass (ESI): 346 (M+Na)$^+$, 324 (M+H)$^+$ $^1$H NMR (DMSO-d$_6$, δ): 1.11 (6H, d, J=6.60 Hz), 5.02 (1H, 7-plet, J=6.60 Hz), 6.75 (1H, d, J=9.58 Hz), 7.03-7.35 (8H, m), 11.90 (1H, s)

The following 12 compounds were obtained in a similar manner to that of Example 165.

EXAMPLE 175

6-[5-amino-3-phenyl-6-(3-phenylpropoxy)-2-pyrazinyl]-2-isopropyl-3(2H)-pyridazinone m.p.: 105-106.5° C.

IR (KBr): 3483, 3269, 3143, 1666, 1622, 1591 cm$^{-1}$

Mass (ESI): 464 (M+Na)$^+$, 442 (M+H)$^+$ $^1$H NMR (CDCl$_3$, δ): 0.84 (6H, d, J=6.60 Hz), 2.12-2.29 (2H, m), 2.84 (2H, t, J=7.44 Hz), 4.49 (2H, t, J=6.40 Hz), 4.98-5.18 (3H, m), 6.91 (1H, d, J=9.58 Hz), 7.17-7.38 (10H, m), 7.66 (1H, d, J=9.58 Hz)

EXAMPLE 176

6-{5-amino-6-[(1-benzyl-3-pyrrolidinyl)oxy]-3-phenyl-2-pyrazinyl}-2-isopropyl-3(2H)-pyridazinone m.p.: 179-181° C.

IR (KBr): 3483, 3267, 3140, 2978, 2783, 1666, 1622, 1591 cm$^{-1}$

Mass (ESI): 505 (M+Na)$^+$, 483 (M+H)$^+$ $^1$H NMR (CDCl$_3$, δ): 0.85 (6H, d, J=6.60 Hz), 2.03-2.18 (1H, m), 2.40-2.64 (2H, m), 2.88-3.08 (3H, m), 3.70 (1H, d, J=12.88 Hz), 3.79 (1H, d, J=12.88 Hz), 5.06 (1H, 7-plet, J=6.60 Hz), 5.14 (2H, brs), 5.50-5.61 (1H, m), 6.88 (1H, d, J=9.60 Hz), 7.21-7.41 (10H, m), 7.60 (1H, d, J=9.60 Hz)

EXAMPLE 177

6-{5-amino-6-[(1-benzyl-3-piperidinyl)oxy]-3-phenyl-2-pyrazinyl}-2-isopropyl-3(2H)-pyridazinone IR (Neat): 3477, 3309, 3209, 2939, 2862, 2806, 1662, 1635, 1624, 1587, 1506 cm$^{-1}$ Mass (ESI): 519 (M+Na)$^+$, 497 (M+H)$^+$ $^1$H NMR (CDCl$_3$, δ): 0.81 (3H, d, J=6.60 Hz), 0.86 (3H, d, J=6.60 Hz), 5.05 (1H, 7-plet, J=6.60 Hz), 5.26 (2H, brs), 6.87(1H, d, J=9.56 Hz), 7.22-7.34 (10H, m), 7.42 (1H, d, J=9.56 Hz)

EXAMPLE 178

6-{5-amino-6-[(1-benzyl-4-piperidinyl)oxy]-3-phenyl-2-pyrazinyl}-2-isopropyl-3(2H)-pyridazinone m.p.: 148-150.5° C.

IR (KBr): 3485, 3275, 3145, 1666, 1620, 1589 cm$^{-1}$

Mass (ESI): 519 (M+Na)$^+$, 497 (M+H)$^+$ $^1$H NMR (CDCl$_3$, δ): 0.86 (6H, d, J=6.60 Hz), 1.90-2.03 (2H, m), 2.13-2.25 (2H, m), 2.38-2.50 (2H, m), 2.76-2.92

(2H, m), 3.62 (2H, s), 4.98-5.27 (4H, m), 6.90 (1H, d, J=9.60 Hz), 7.21-7.38 (10H, s), 7.59 (1H, d, J=9.60 Hz)

EXAMPLE 179

6-(5-amino-6-butoxy-3-phenyl-2-pyrazinyl)-2-methyl-3(2H)-pyridazinone
m.p.: 143-144° C.
IR (KBr): 3433, 3404, 3307, 3215, 2954, 1651, 1614, 1581 cm$^{-1}$
Mass (ESI): 725 (2M+Na)$^+$, 374 (M+Na)$^+$, 352 (M+H)$^+$
$^1$H NMR (CDCl$_3$, δ): 1.01 (3H, t, J=7.30 Hz), 1.42-1.62 (2H, m), 1.76-1.91 (2H, m), 3.55 (3H, s), 4.46 (2H, t), 5.25 (2H, brs), 6.82 (1H, d, J=9.60 Hz), 7.26-7.38 (5H, m), 7.41 (1H, d, J=9.60 Hz)

EXAMPLE 180

6-[5-amino-6-(2-methoxyethoxy)-3-phenyl-2-pyrazinyl]-2-methyl-3(2H)-pyridazinone
m.p.: 139-141° C.
IR (KBr): 3494, 3471, 3386, 3288, 3188, 1664, 1653, 1583 cm$^{-1}$
Mass (ESI): 376 (M+Na)$^+$, 354 (M+H)$^+$
$^1$H NMR (CDCl$_3$, δ): 3.45 (3H, s), 3.55 (3H, s), 3.78-3.84 (2H, m), 4.60-4.66 (2H, m), 5.26 (2H, brs), 6.82 (1H, d, J=9.60 Hz), 7.29-7.38 (5H, m), 7.39 (1H, d, J=9.60 Hz)

EXAMPLE 181

6-{5-amino-6-[2-(4-morpholinyl)ethoxy]-3-phenyl-2-pyrazinyl}-2-methyl-3(2H)-pyridazinone
m.p.: 185-187° C.
IR (KBr): 3435, 3307, 3182, 1653, 1574 cm$^{-1}$
Mass (ESI): 839 (2M+Na)$^+$, 431 (M+Na)$^+$, 409 (M+H)$^+$
$^1$H NMR (CDCl$_3$, δ): 2.63-2.70 (4H, m), 2.92 (2H, t, J=5.70 Hz), 3.56 (3H, s), 3.74-3.84 (4H, m), 4.61 (2H, t, J=5.70 Hz), 5.37 (2H, brs), 6.80 (1H, d, J=9.70 Hz), 7.28-7.41 (6H, m)

EXAMPLE 182

6-[5-amino-6-(benzyloxy)-3-phenyl-2-pyrazinyl]-2-methyl-3(2H)-pyridazinone
m.p.: 185-187° C.
IR (KBr): 3406, 3305, 3211, 1649, 1616, 1577, 1547 cm$^{-1}$
Mass (ESI): 793 (2M+Na)$^+$, 408 (M+Na)$^+$, 386 (M+H)$^+$
$^1$H NMR (CDCl$_3$, δ): 3.56 (3H, s), 5.27 (2H, brs), 5.50 (2H, s), 6.83 (1H, d, J=9.60 Hz), 7.29-7.52 (11H, m)

EXAMPLE 183

6-[5-amino-3-phenyl-6-(3-phenylpropoxy)-2-pyrazinyl]-2-methyl-3(2H)-pyridazinone
m.p.: 91-94° C.
IR (KBr): 3384, 3296, 3195, 1666, 1658, 1624, 1585 cm$^{-1}$
Mass (ESI): 849 (2M+Na)$^+$, 436 (M+Na)$^+$, 414 (M+H)$^+$
$^1$H NMR (CDCl$_3$, δ): 2.13-2.27 (2H, m), 2.83 (2H, t, J=7.45 Hz), 3.54 (3H, s), 4.49 (2H, t, J=6.38 Hz), 5.05 (2H, brs), 6.81 (1H, d, J=9.62 Hz), 7.17-7.41 (11H, m)

EXAMPLE 184

6-[5-amino-6-(2-furylmethoxy)-3-phenyl-2-pyrazinyl]-2-methyl-3(2H)-pyridazinone
m.p.: 158-159.5° C.
IR (KBr): 3471, 3284, 3151, 1664, 1631, 1587 cm$^{-1}$
Mass (ESI): 773 (2M+Na)$^+$, 398 (M+Na)$^+$, 376 (M+H)$^+$
$^1$H NMR (CDCl$_3$, δ): 3.57 (3H, s), 5.21 (2H, brs), 5.46 (2H, s), 6.40-6.43 (1H, m), 6.51-6.54 (1H, m), 6.84 (1H, d, J=9.60 Hz), 7.28-7.38 (5H, m), 7.42 (1H, d, J=9.60 Hz), 7.46-7.48 (1H, m)

EXAMPLE 185

6-{5-amino-6-[(1-benzyl-4-piperidinyl)oxy]-3-phenyl-2-pyrazinyl}-2-methyl-3(2H)-pyridazinone
m.p.: 147-149° C.
IR (KBr): 3491, 3278, 3151, 2941, 1668, 1620, 1589 cm$^{-1}$
Mass (ESI): 959 (2M+Na)$^+$, 491 (M+Na)$^+$, 469 (M+H)$^+$
$^1$H NMR (CDCl$_3$, δ): 1.90-2.90 (8H, m), 3.53 (3H, s), 3.64 (2H, brs), 5.05 (2H, brs), 5.15-5.35 (1H, m), 6.82 (1H, d, J=9.64 Hz), 7.28-7.40 (11H, m)

EXAMPLE 186

6-[5-amino-6-(4-fluorophenoxy)-3-phenyl-2-pyrazinyl]-2-methyl-3(2H)-pyridazinone
m.p.: 229-231° C.
IR (KBr): 3485, 3282, 3153, 1651, 1622, 1587, 1504 cm$^{-1}$
Mass (ESI): 801 (2M+Na)$^+$, 412 (M+Na)$^+$, 390 (M+H)$^+$
$^1$H NMR (CDCl$_3$, δ): 3.27 (3H, s), 6.83 (1H, d, J=9.58 Hz), 7.11 (2H, brs), 7.23-7.42 (10H, m)

EXAMPLE 187

To a suspension of NaH (60% in oil suspension) (33.6 mg) in 1,2-dimethyl-2-imidazolidinone (0.6 ml) was added 2-phenylethanol (0.101 ml) and the mixture was stirred at 25-30° C. for 30 minutes. 6-[5-Amino-6-(methylsulfonyl)-3-phenyl-2-pyrazinyl]-2-methyl-3(2H)-pyridazinone (150 mg) was added and the mixture was heated at 100-105° C. for 15 hours. To the mixture was added 0.1N HCl (3 ml) and a precipitate was collected by filtration. The precipitate was suspended in CHCl$_3$ and collected by filtration to give 6-(5-amino-6-hydroxy-3-phenyl-2-pyrazinyl)-2-methyl-3(2H)-pyridazinone (60 mg). The CHCl$_3$ solution was dried over MgSO$_4$, concentrated under reduced pressure and purified by column chromatography on silica gel eluting with a mixture of n-hexane and EtOAc (50:50 v/v) to give a solid. The solid was suspended in acetone and collected by filtration to give 6-[5-amino-3-phenyl-6-(2-phenylethoxy)-2-pyrazinyl]-2-methyl-3(2H)-pyridazinone (7 mg).

6-[5-amino-3-phenyl-6-(2-phenylethoxy)-2-pyrazinyl]-2-methyl-3(2H)-pyridazinone
m.p.: 156-159° C.
IR (KBr): 3489, 3404, 3383, 3261, 3091, 1662, 1612 cm$^{-1}$
Mass (ESI): 821 (2M+Na)$^+$, 422 (M+Na)$^+$, 400 (M+H)$^+$
$^1$H NMR (CDCl$_3$, δ): 3.16 (2H, t, J=6.97 Hz), 3.55 (3H, s), 4.67 (2H, t, J=6.97 Hz), 5.21 (2H, brs), 6.82 (1H, d, J=9.60 Hz), 7.21-7.41 (11H, m)

6-(5-amino-6-hydroxy-3-phenyl-2-pyrazinyl)-2-methyl-3(2H)-pyridazinone
m.p.: >250° C.
IR (KBr): 3404, 3307, 3203, 3130, 3041, 1675, 1655, 1620, 1583, 1520 cm$^{-1}$
Mass (ESI): 613 (2M+Na)$^+$, 318 (M+Na)$^+$, 296 (M+H)$^+$
$^1$H NMR (DMSO-d$_6$, δ): 3.67 (3H, s), 6.69 (1H, d, J=9.66 Hz), 6.75 (1H, d, J=9.65 Hz), 7.09 (2H, brs), 7.36 (5H, s), 11.70 (1H, brs)

EXAMPLE 188

Under nitrogen atmosphere, a solution of Na$_2$CO$_3$ (427 mg) in water (8.8 ml) was added to a suspension of N'-[6-chloro-3-cyano-5-(1-isopropyl-6-oxo-1,6-dihydro-3-pyridazinyl)-2-pyrazinyl]-N,N-dimethylimidoformamide (346 mg), (2-bromophenyl)boronic acid (503 mg) and tetrakis(triphenylphosphine)palladium (35 mg) in dioxane (22 ml) and the mixture was stirred at 100-105° C. for 4 hours. Dioxane was evaporated under reduced pressure to give a residue. The residue was dissolved in CHCl$_3$, dried over MgSO$_4$, concentrated under reduced pressure and purified by column chromatography on silica gel. By elution with a mixture of n-hexane and EtOAc (70:30 v/v) was obtained 3-amino-5-(2-bromophenyl)-6-(1-isopropyl-6-oxo-1,6-dihydro-3-pyridazinyl)-2-pyrazinecarbonitrile as a solid (42 mg) and by elution with a mixture of n-hexane and EtOAc (50:50 v/v) was obtained N'-[6-(2-bromophenyl)-3-cyano-5-(1-isopropyl-6-oxo-1,6-dihydro-3-pyridazinyl)-2-pyrazinyl]-N,N-dimethylimidoformamide as a solid (360 mg).

N'-[6-(2-bromophenyl)-3-cyano-5-(1-isopropyl-6-oxo-1,6-dihydro-3-pyridazinyl)-2-pyrazinyl]-N,N-dimethylimidoformamide m.p.: 197-199° C.

IR (KBr): 3455-3405, 2233, 1672, 1620, 1531, 1504 cm$^{-1}$

Mass (ESI): 957 and 955 (2M+Na)$^+$, 490 and 488 (M+Na)$^+$, 468 and 466 (M+H)$^+$ $^1$H NMR (DMS O-d$_6$, δ): 0.72 (6H, d, J=6.65 Hz), 3.17 (3H, s), 3.21 (3H, s), 4.89 (1H, 7-plet, J=6.65 Hz), 7.00 (1H, d, J=9.70 Hz), 7.33-7.41 (1H, m), 7.52-7.55 (2H, m), 7.67 (1H, d, J=7.96 Hz), 7.97 (1H, d, J=9.70 Hz), 8.69 (1H, s)

3-amino-5-(2-bromophenyl)-6-(1-isopropyl-6-oxo-1,6-dihydro-3-pyridazinyl)-2-pyrazinecarbonitrile m.p.: 240-243° C.

IR (KBr): 3415, 3303, 3190-3145, 2227, 1647, 1585, 1547, 1510 cm$^{-1}$

Mass (ESI): 435 and 423 (M+Na)$^+$, 413 and 411 (M+H)$^+$ $^1$H NMR (DMSO-d$_6$, δ): 0.71 (6H, d, J=6.60 Hz), 4.89 (1H, 7-plet, J=6.60 Hz), 6.96 (1H, d, J=9.68 Hz), 7.30-7.69 (4H, m), 7.93 (2H, brs), 7.90 (1H, d, J=9.68 Hz)

EXAMPLE 189

A solution of N'-[6-(2-bromophenyl)-3-cyano-5-(1-isopropyl-6-oxo-1,6-dihydro-3-pyridazinyl)-2-pyrazinyl]-N,N-dimethylimidoformamide (285 mg) in a mixture of water (2 ml) and 4N hydrogen chloride in dioxane (6 ml) was stirred at 20-25° C. for 18 hours. After addition of water (18 ml), the mixture was neutralized with 1N aq. NaOH to give a solid. The solid was collected by filtration and purified by column chromatography on silica gel eluting with a mixture of n-hexane and EtOAc (50:50 v/v) to give 3-amino-5-(2-bromophenyl)-6-(1-isopropyl-6-oxo-1,6-dihydro-3-pyridazinyl)-2-pyrazinecarbonitrile as a solid (163 mg).

m.p.: 240-243° C.

IR (KBr): 3415, 3303, 3190-3145, 2227, 1647, 1585, 1547, 1510 cm$^{-1}$

Mass (ESI): 435 and 423 (M+Na)$^+$, 413 and 411 (M+H)$^+$ $^1$H NMR (DMSO-d$_6$, δ): 0.71 (6H, d, J=6.60 Hz), 4.89 (1H, 7-plet, J=6.60 Hz), 6.96 (1H, d, J=9.68 Hz), 7.30-7.69 (4H, m), 7.93 (2H, brs), 7.90 (1H, d, J=9.68 Hz)

EXAMPLE 190

A mixture of 3-amino-5-(2-bromophenyl)-6-(1-isopropyl-6-oxo-1,6-dihydro-3-pyridazinyl)-2-pyrazinecarbonitrile (59 mg) in 25% hydrogen bromide in AcOH (0.36 ml) was stirred at 20-25° C. for 5 hours. Dioxane (3 ml) was added to the mixture to give a precipitate. The precipitate was collected by filtration and suspended in sat. aq. NaHCO$_3$ to give a solid. The solid was collected by filtration and dried under reduced pressure to give 3-amino-5-(2-bromophenyl)-6-(1-isopropyl-6-oxo-1,6-dihydro-3-pyridazinyl)-2-pyrazinecarboxamide (17 mg).

m.p.: 132-135° C.

IR (KBr): 3470-3415, 3325-3295, 1655, 1581 cm$^{-1}$

Mass (ESI): 453 and 451 (M+Na)$^+$, 431 and 429 (M+H)$^+$ $^1$H NMR (DMSO-d$_6$, δ): 0.69 (3H, d, J=6.75 Hz), 0.72 (3H, d, J=6.75 Hz), 4.90 (1H, 7-plet, J=6.75 Hz), 6.94 (1H, d, J=9.70 Hz), 7.27-8.15 (7H, m), 8.41 (1H, brs), 8.43 (1H, d, J=9.70 Hz)

EXAMPLE 191

Under nitrogen atmosphere, a solution of Na$_2$CO$_3$ (138 mg) in water (0.8 ml) was added to a suspension of 3-amino-5-chloro-6-(1-isopropyl-6-oxo-1,6-dihydro-3-pyridazinyl)-2-pyrazinecarboxamide (100 mg), 2-thienylboronic acid (104 mg) and tetrakis(triphenylphosphine)palladium (11.3 mg) in dioxane (2 ml) and the mixture was stirred at 100-105° C. for 4 hours. After addition of water (10 ml), a precipitate was collected by filtration and purified by column chromatography on silica gel eluting with a mixture of n-hexane and EtOAc (40:60 v/v) to give 3-amino-6-(1-isopropyl-6-oxo-1,6-dihydro-3-pyridazinyl)-5-(2-thienyl)-2-pyrazinecarboxamide as a solid (85 mg).

m.p.: 238-240° C.

IR (KBr): 3383, 3280, 1653, 1585, 1529 cm$^{-1}$

Mass (ESI): 379(M+Na)$^+$, 357(M+H)$^+$ $^1$H NMR (CDCl$_3$, δ): 1.02 (6H, d, J=6.60 Hz), 5.08 (1H, 7-plet, J=6.60 Hz), 7.02-7.09 (3H, m), 7.65-8.15 (6H, m)

The following 3 compounds were obtained in a similar manner to that of Example 191.

EXAMPLE 192

3-amino-5-(2-bromophenyl)-6-(1-isopropyl-6-oxo-1,6-dihydro-3-pyridazinyl)-2-pyrazinecarboxamide m.p.: 240-243° C.

IR (KBr): 3415, 3303, 3190-3145, 2227, 1647, 1585, 1547, 1510 cm$^{-1}$

Mass (ESI): 435 and 423 (M+Na)$^+$, 413 and 411 (M+H)$^+$ $^1$H NMR (DMSO-d$_6$, δ): 0.71 (6H, d, J=6.60 Hz), 4.89 (1H, 7-plet, J=6.60 Hz), 6.96 (1H, d, J=9.68 Hz), 7.30-7.69 (4H, m), 7.93 (2H, brs), 7.90 (1H, d, J=9.68 Hz)

EXAMPLE 193

3-amino-6-(1-isopropyl-6-oxo-1,6-dihydro-3-pyridazinyl)-5-(4-pyridyl)-2-pyrazinecarboxamide Mass (ESI): 374 (M+Na)$^+$, 352 (M+H)$^+$ $^1$H NMR (CDCl$_3$, δ): 0.82 (6H, d, J=6.62 Hz), 5.09 (1H, 7-plet, J=6.62 Hz), 5.65 (1H, brs), 7.02 (1H, d, J=9.58 Hz), 7.38-7.43 (2H, m), 7.60 (1H, brs), 7.81 (1H, d, J=9.58 Hz), 8.66-8.70 (2H, m)

EXAMPLE 194

3-amino-6-(1-isopropyl-6-oxo-1,6-dihydro-3-pyridazinyl)-5-(6-methoxy-3-pyridyl)-2-pyrazinecarboxamide m.p.: 250-252° C.

IR (KBr): 3390, 3251, 3167, 1664, 1591 cm$^{-1}$

Mass (ESI): 404 (M+Na)$^+$ $^1$H NMR (DMSO-d$_6$, δ): 0.77 (6H, d, J=6.62 Hz), 3.85 (3H, s), 4.92 (1H, 7-plet, J=6.62 Hz), 6.87 (1H, d, J=8.62 Hz), 6.98 (1H, d, J=9.62 Hz), 7.7-8.2 (2H, br-peak), 7.74

(1H, brs), 7.77 (1H, dd, J=2.38, 8.62 Hz), 8.21 (1H, d, J=2.38 Hz), 8.30 (1H, d, J=9.62 Hz), 8.32 (1H, brs)

EXAMPLE 195

A mixture of 1-(2-bromophenyl)-2-(1-isopropyl-6-oxo-1,6-dihydro-3-pyridazinyl)-1,2-ethanedione (5.30 g) and (2Z)-2,3-diamino-2-butenedinitrile (1.65 g) in a solution of DMSO (0.25 ml) and toluene (25 ml) was refluxed for 8 hours. The mixture was concentrated under reduced pressure to give a residue. The residue was purified by column chromatography on silica gel eluting with a mixture of n-hexane and EtOAc (85:15 v/v) to give 5-(2-bromophenyl)-6-(1-isopropyl-6-oxo-1,6-dihydro-3-pyridazinyl)-2,3-pyrazinedicarbonitrile as a solid (3.58 g).

m.p.: 159.5-161° C.
IR (KBr): 2227, 1666, 1589, 1516 cm$^{-1}$
Mass (ESI): 445 and 443 (M+Na)$^+$, 423 and 421 (M+H)$^+$
$^1$H NMR (CDCl$_3$, δ): 0.79 (6H, brs), 5.08 (1H, 7-plet, J=6.52 Hz), 7.04 (1H, d, J=10.02 Hz), 7.32-7.42 (1H, m), 7.52-7.63 (3H, m), 8.09 (1H, d)
$^1$H NMR (DMSO-d$_6$, δ): 0.73 (6H, d, J=6.62 Hz), 4.92 (1H, 7-plet, J=6.62 Hz), 7.11 (1H, d, J=9.78 Hz), 7.43-7.49 (1H, m), 7.58-7.64 (2H, m), 7.74-7.77 (1H, m), 8.14 (1H, d, J=9.78 Hz)

EXAMPLE 196

To a solution of 5-(2-bromophenyl)-6-(1-isopropyl-6-oxo-1,6-dihydro-3-pyridazinyl)-2,3-pyrazinedicarbonitrile (3.00 g) in 1,3-dimethyl-2-imidazolidinone (6 ml), (4-methoxybenzyl)amine (0.96 ml) was added and the mixture was stirred at 25-30° C. for 100 hours. After addition of 0.5N aq. NaOH (15 ml), the mixture was stirred for one hour and a precipitate was collected by filtration to give a solid. The solid was dissolved in EtOAc, washed with water, dried over MgSO$_4$ and concentrated under reduced pressure to give a residue. The residue was purified by column chromatography on silica gel eluting with a mixture of n-hexane and EtOAc (70:30 v/v) to give 5-(2-bromophenyl)-6-(1-isopropyl-6-oxo-1,6-dihydro-3-pyridazinyl)-3-[(4-methoxybenzyl)amino]-2-pyrazinecarbonitrile as an amorphous solid (2.58 g) containing 6-(2-bromophenyl)-5-(1-isopropyl-6-oxo-1,6-dihydro-3-pyridazinyl)-3-[(4-methoxybenzyl)amino]-2-pyrazinecarbonitrile.

5-(2-bromophenyl)-6-(1-isopropyl-6-oxo-1,6-dihydro-3-pyridazinyl)-3-[(4-methoxybenzyl)amino]-2-pyrazinecarbonitrile
m.p.: 76-78 C
IR (KBr): 2217, 1658, 1570, 1512 cm
Mass (ESI): 555 and 553 (M+Na), 533 and 531 (M+H)
$^1$H NMR (CDCl$_3$, δ): 0.78 (6H, brs), 3.82 (3H, s), 4.66 (2H, d, J=5.50 Hz), 5.05 (1H, 7-plet, J=6.62 Hz), 5.74 (1H, t, J=5.50 Hz), 6.87-6.98 (3H, m), 7.25-7.31 (3H, m), 7.40-7.60 (3H, m), 7.90 (1H, d, J=9.60 Hz)

EXAMPLE 197

To a solution of 5-(2-bromophenyl)-6-(1-isopropyl-6-oxo-1,6-dihydro-3-pyridazinyl)-3-[(4-methoxybenzyl)amino]-2-pyrazinecarbonitrile (2.05 g) containing 6-(2-bromophenyl)-5-(1-isopropyl-6-oxo-1,6-dihydro-3-pyridazinyl)-3-[(4-methoxybenzyl)amino]-2-pyrazinecarbonitrile in CHCl$_3$ (60 ml), water (3 ml) and 2,3-dichloro-5,6-dicyano-1,4-benzoqinone (2.63 g) were added and the mixture was stirred at 25-30° C. for 24 hours. The mixture was washed with 1N aq. NaOH, dried over MgSO$_4$ and concentrated under reduced pressure to give a residue. The residue was purified by column chromatography on silica gel. By elution of a mixture of n-hexane and EtOAc (70:30 v/v) was obtained 3-amino-5-(2-bromophenyl)-6-(1-isopropyl-6-oxo-1,6-dihydro-3-pyridazinyl)-2-pyrazinecarbonitrile as a solid (941 mg) and by elution of a mixture of n-hexane and EtOAc (50:50 v/v) was obtained 3-amino-6-(2-bromophenyl)-5-(1-isopropyl-6-oxo-1,6-dihydro-3-pyridazinyl)-2-pyrazinecarbonitrile as a solid (92 mg).

3-amino-5-(2-bromophenyl)-6-(1-isopropyl-6-oxo-1,6-dihydro-3-pyridazinyl)-2-pyrazinecarbonitrile
m.p.: 240-243° C.
IR (KBr): 3415, 3303, 3190-3145, 2227, 1647, 1585, 1547, 1510 cm$^{-1}$
Mass (ESI): 435 and 423 (M+Na)$^+$, 413 and 411 (M+H)$^+$
$^1$H NMR (DMSO-d$_6$, δ): 0.71 (6H, d, J=6.60 Hz), 4.89 (1H, 7-plet, J=6.60 Hz), 6.96 (1H, d, J=9.68 Hz), 7.30-7.69 (4H, m), 7.93 (2H, brs), 7.90(1H, d, J=9.68 Hz)

3-amino-6-(2-bromophenyl)-5-(1-isopropyl-6-oxo-1,6-dihydro-3-pyridazinyl)-2-pyrazinecarbonitrile
m.p.: 241-243° C.
IR (KBr): 3340, 3303, 3176, 2222, 1651, 1587, 1552, 1529 cm$^{-1}$
Mass (ESI): 847, 845 and 843 (2M+Na)$^+$, 435 and 433 (M+Na)$^+$, 413 and 412 (M+H)$^+$
$^1$H NMR (DMSO-d$_6$, δ): 0.71 (6H, d, J=6.60 Hz), 4.89 (1H, 7-plet, J=6.60 Hz), 7.06 (1H, d, J=9.72 Hz), 7.26-7.37 (1H, m), 7.46-7.50 (2H, m), 7.64 (1H, d, J=7.86 Hz), 7.74 (2H, brs), 7.94 (1H, d, J=9.72 Hz)

EXAMPLE 198

A solution of 3-amino-5-(2-bromophenyl)-6-(1-isopropyl-6-oxo-1,6-dihydro-3-pyridazinyl)-2-pyrazinecarboxamide (695 mg) in a mixture of 5N aq. NaOH (4 ml) and EtOH (4 ml) was refluxed for 4 hours. After removal of EtOH by evaporation, the mixture was adjusted to pH 4 with 1N HCl to give a precipitate. The precipitate was collected by filtration and dried under reduced pressure to give 3-amino-5-(2-bromophenyl)-6-(1-isopropyl-6-oxo-1,6-dihydro-3-pyridazinyl)-2-pyrazinecarboxylic acid (664 mg).

m.p.: 237° C. (dec.)
IR (KBr): 3415, 3271, 1714, 1643, 1606, 1574 cm$^{-1}$
Mass (ESI): 454 and 452 (M+Na)$^+$
$^1$H NMR (DMSO-d$_6$, δ): 0.72 (6H, d, J=6.60 Hz), 4.90 (1H, 7-plet, J=6.60 Hz), 6.98 (1H, d, J=9.62 Hz), 7.29-7.38 (1H, m), 7.43-7.55 (2H, m), 7.65 (1H, d, J=7.86 Hz), 7.79 (2H, brs), 8.12 (1H, d, J=9.62 Hz), 13.3 (1H, br-peak)

EXAMPLE 199

A mixture of 3-amino-5-(2-bromophenyl)-6-(1-isopropyl-6-oxo-1,6-dihydro-3-pyridazinyl)-2-pyrazinecarboxylic acid (601 mg) in 1,2-dichlorobenzene (3 ml) was refluxed for 2 hours. After cooling, the mixture was purified by column chromatography on silica gel (EtOAc only) to give a solid. The solid was suspended with acetone and collected by filtration to give 6-[5-amino-3-(2-bromophenyl)-2-pyrazinyl]-2-isopropyl-3(2H)-pyridazinone as a solid (554 mg).

m.p.: 189-191° C.
IR (KBr): 3346, 3307, 3178, 1651, 1643, 1587, 1572, 1537 cm$^{-1}$
Mass (ESI): 410 and 408 (M+Na)$^+$, 388 and 386 (M+H)$^+$ $^1$H NMR (DMSO-d$_6$, δ): 0.71 (6H, d, J=6.62 Hz), 4.88 (1H, 7-plet, J=6.62 Hz), 6.92 (1H, d, J=9.66 Hz), 6.95 (2H, brs), 7.24-7.46 (3H, m), 7.59-7.64 (1H, m), 7.92 (1H, d, J=9.66 Hz), 7.99 (1H, s)

EXAMPLE 200

A mixture of N'-[6-chloro-3-cyano-5-(1-isopropyl-6-oxo-1,6-dihydro-3-pyridazinyl)-2-pyrazinyl]-N,N-dimethylimidoformamide (100 mg), 4-fluorophenylboronic acid (122 mg), tetrakistriphenylphosphine palladium (10 mg) and Na$_2$CO$_3$ (123 mg) in dioxane (5 ml) and water (1 ml) was stirred at 90° C. for 15 hours. Water and EtOAc were added to the reaction mixture. The organic layer was separated, and dried over MgSO$_4$. The solvent was removed in vacuo. The residue was purified by silica gel column chromatography eluted with a mixture of n-hexane and EtOAc. The fractions were concentrated in vacuo to obtain N'-[3-cyano-6-(4-fluorophenyl)-5-(1-isopropyl-6-oxo-1,6-dihydro-3-pyridazinyl)-2-pyrazinyl]-N,N-dimethylimidoformamide (121 mg) as white powder.
$^1$H NMR (DMSO-d$_6$, δ): 0.86 (6H, d, J=6.6 Hz), 3.21 (3H, s), 3.26 (3H, s), 5.09 (1H, 7-plet, J=6.6 Hz), 6.98 (1H, d, J=9.6 Hz), 7.0-7.5 (4H, m), 7.86 (1H, d, J=9.6 Hz), 8.72 (1H, s)
Mass (ESI): 406 (M+H)$^+$, 428 (M+Na)$^+$

EXAMPLE 201

A mixture of N'-[6-chloro-3-cyano-5-(1-isopropyl-6-oxo-1,6-dihydro-3-pyridazinyl)-2-pyrazinyl]-N,N-dimethylimidoformamide (200 mg), 3-fluorophenylboronic acid (243 mg), tetrakistriphenylphosphine palladium (20.1 mg) and Na$_2$CO$_3$(246 mg) indioxane (10 ml) and water (2 ml) was stirred at 90° C. for 15 hours. Water and EtOAc were added to the reaction mixture. The organic layer was separated, and dried over MgSO$_4$. The solvent was removed in vacuo. The residue was purified by silica gel column chromatography eluted with a mixture of n-hexane and EtOAc. The fractions were concentrated in vacuo to obtain N'-[3-cyano-6-(3-fluorophenyl)-5-(1-isopropyl-6-oxo-1,6-dihydro-3-pyridazinyl)-2-pyrazinyl]-N,N-dimethylimidoformamide (100 mg) as white powder.
$^1$H NMR (DMSO-d$_6$, δ): 0.85 (6H, d, J=6.6 Hz), 3.22 (3H, s), 3.26 (3H, s), 5.09 (1H, 7-plet, J=6.6 Hz), 6.99 (1H, d, J=9.6 Hz), 7.0-7.5 (4H, m), 7.89 (1H, d, J=9.6 Hz), 8.73(1H, s)
Mass (ESI): 406 (M+H)$^+$, 428 (M+Na)$^+$

The invention claimed is:
1. A pyrazine compound shown by the following formula (I):

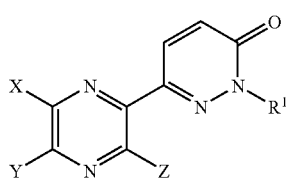

wherein
R$^1$ is hydrogen, lower alkyl or substituted lower alkyl
X is hydrogen, halogen, hydroxy, mercapto, cyano or acyl, or
lower alkyl, substituted lower alkyl, lower alkenyl, substituted lower alkenyl, lower alkynyl, substituted lower alkynyl, lower alkoxy, substituted lower alkoxy, cyclo (lower)alkoxy, lower alkylthio, aryloxy, arylthio, amino, substituted amino, aryl, substituted aryl, heterocyclic group, substituted heterocyclic group or heterocyclyloxy;
Y is hydrogen, halogen, hydroxy, mercapto, cyano, acyl or
lower alkyl, substituted lower alkyl, lower alkoxy, substituted lower alkoxy, lower alkylthio, amino, substituted amino, aryl, substituted aryl, or heteroaryl; and
Z is aryl, substituted aryl, or heteroaryl;
or a salt thereof
wherein substituted lower alkyl is substituted with a substituent selected from the group consisting of halogen, lower alkenyl, lower alkoxy, hydroxy, cyclo(lower)alkyl, amino, substituted amino, acylamino, aryl, substituted aryl, heterocyclic group and acyl;
wherein substituted lower alkenyl is substituted with a substituent selected from the group consisting of lower alkoxy, hydroxy, cyclo(lower)alkyl, amino, aryl, heterocyclic group and acyl;
wherein substituted lower alkynyl is substituted with a substituent selected from the group consisting of lower alkoxy, hydroxy, cyclo(lower)alkyl, amino, aryl, heterocyclic group and acyl;
wherein substituted lower alkoxy is substituted with a substituent selected from the group consisting of hydroxy, halogen, cyclo(lower)alkyl, lower alkoxy, amino, substituted amino, aryl, substituted aryl, heterocyclic group and acyl;
wherein substituted amino is substituted with a substituent selected from the group consisting of lower alkyl, acyl, sulfonyl, methylene, (dimethylamino)methylene and dimethylsulfanylidene;
wherein substituted aryl is substituted with a substituent selected from the group consisting of lower alkyl, lower alkoxy, hydroxyl and halogen; and
wherein substituted heterocyclic group is substituted with a substituent selected from the group consisting of lower alkyl, lower alkoxy, hydroxy, oxo, halogen, benzyl, amino, substituted amino and aryl.
2. A pyrazine compound of claim 1, wherein
R$^1$ is hydrogen or lower alkyl; and
Y is hydrogen, hydroxy, lower alkoxy, cyano, acyl or amino, substituted amino or a salt thereof
wherein substituted amino is substituted with a substituent selected from the group consisting of lower alkyl, acyl, sulfonyl, methylene, (dimethylamino)methylene and dimethylsulfanylidene.
3. A pyrazine compound of claim 2, wherein
R$^1$ is lower alkyl;
Y is hydrogen, amino or dimethylsulfanylideneamino; and
Z is phenyl, substituted phenyl, pyridyl or thienyl or a salt thereof
wherein substituted phenyl is substituted with a substituent selected from the group consisting of lower alkyl, lower alkoxy, hydroxy, halogen.
4. A pyrazine compound of claim 3, wherein
X is hydrogen, halogen, hydroxy, cyano, carboxy, lower alkyl carbonyl, lower alkoxy carbonyl, lower alkyl sulfinyl, lower alkyl sulfonyl;
or a salt thereof.
5. A pyrazine compound of claim 3, wherein
X is lower alkyl, substituted lower alkyl, lower alkoxy, substituted lower alkoxy, cyclo(lower)alkyl, lower alkylthio, carbamoyl, thiocarbamoyl, aryloxy, arylthio, amino, substituted amino, aryl, substituted aryl, heterocyclic group, substituted heterocyclic group or heterocyclyloxy;
or a salt thereof
wherein substituted lower alkyl is substituted with a substituent selected from the group consisting of halogen, lower alkenyl, lower alkoxy, hydroxy, cyclo(lower)alkyl, amino, substituted amino, acylamino, aryl, substituted aryl, heterocyclic group and acyl;
wherein substituted lower alkyl is substituted with a substituent selected from the group consisting of hydroxy, halogen, cyclo(lower)alkyl, lower alkoxy, amino, substituted amino, aryl, substituted aryl, heterocyclic group and acyl;
wherein substituted amino is substituted with a substituent selected from the group consisting of lower alkyl, acyl, sulfonyl, methylene, (dimethylamino)methylene and dimethylsulfanylidene;
wherein substituted aryl is substituted with a substituent selected from the group consisting of lower alkyl, lower alkoxy, hydroxyl and halogen; and
wherein substituted heterocyclic group is substituted with a substituent selected from the group consisting of lower alkyl, lower alkoxy, hydroxy, oxo, halogen, benzyl, amino, substituted amino and aryl.

6. A pyrazine compound of claim 3, wherein
Y is hydrogen or amino; and
Z is phenyl, substituted phenyl, or thienyl;
or a salt thereof
wherein substituted phenyl is substituted with a substituent selected from the group consisting of lower alkyl, lower alkoxy, hydroxyl and halogen.

7. A pyrazine compound of claim 6, wherein
X is hydrogen, chloro, bromo, hydroxy, cyano, methylcarbonyl, methylthio, carbamoyl, furyl, thienyl, pyrrolyl, pyrazolyl, triazolyl, phenoxy, fluorophenoxy, pyrrolidinyloxy, benzylpyrrolidinyloxy, thiazolyl, methylthiazolyl or phenylthiazolyl;
or a salt thereof.

8. A pyrazine compound of claim 6, wherein
X is amino, substituted amino, vinyl, substituted vinyl, ethynyl, substituted ethynyl, lower alkoxy, substituted lower alkoxy;
or a salt thereof
wherein substituted amino is substituted with a substituent selected from the group consisting of lower alkyl, acyl, sulfonyl, methylene, (dimethylamino)methylene and dimethylsulfanylidene;
wherein substituted vinyl is substituted with a substituent selected from the group consisting of lower alkoxy, hydroxy, cyclo(lower)alkyl, amino, aryl, heterocyclic group and acyl;
wherein substituted ethynyl is substituted with a substituent selected from the group consisting of lower alkoxy, hydroxy, cyclo(lower)alkyl, amino, aryl, heterocyclic group and acyl;
wherein substituted lower alkoxy is substituted with a substituent selected from the group consisting of hydroxy, halogen, cyclo(lower)alkyl, lower alkoxy, amino, substituted amino, aryl, substituted aryl, heterocyclic group and acyl; and
wherein substituted aryl is substituted with a substituent selected from the group consisting of lower alkyl, lower alkoxy, hydroxyl and halogen.

9. A pyrazine compound of claim 1, wherein
$R^1$ is methyl, ethyl or isopropyl;
X is hydrogen, chloro, bromo, hydroxy, cyano, methylcarbonyl, carbamoyl, pyrazolyl, triazolyl, methylthiazolyl, pyridylmethylamino, methoxyethylamino, furylmethylamino, cyclohexylethynyl, trifluoromethylmethoxy or butoxy;
Y is amino; and
Z is phenyl or fluorophenyl;
or a salt thereof.

10. A pyrazine compound of claim 1, wherein
$R^1$ is lower alkyl;
X is hydrogen, carbamoyl or triazolyl;
Y is amino; and
Z is phenyl;
or a salt thereof.

11. A pyrazine compound of claim 10, which is selected from the group consisting of
1) 3-amino-6-(1-isopropyl-6-oxo-1,6-dihydro-3-pyridazinyl)-5-phenyl-2-pyrazinecarboxamide,
2) 6-(5-amino-3-phenyl-2-pyrazinyl)-2-isopropyl-3(2H)-pyridazinone,
3) 3-amino-6-(1-ethyl-6-oxo-1,6-dihydro-3-pyridazinyl)-5-phenyl-2-pyrazinecarboxamide,
4) 3-amino-6-(1-methyl-6-oxo-1,6-dihydro-3-pyridazinyl)-5-phenyl-2-pyrazinecarboxamide,
5) 6-(5-amino-3-phenyl-2-pyrazinyl)-2-methyl-3(2H)-pyridazinone,
6) 6-(5-amino-3-phenyl-2-pyrazinyl)-2-ethyl-3(2H)-pyridazinone,
7) 6-[5-amino-3-phenyl-6-(1H-1,2,4-triazol-1-yl)-2-pyrazinyl]-2-isopropyl-3(2H)-pyridazinone,
8) 6-[5-amino-3-phenyl-6-(1H-1,2,4-triazol-1-yl)-2-pyrazinyl]-2-methyl-3(2H)-pyridazinone,
or a salt thereof.

12. A process for preparing the pyrazine compound of the following formula (I):

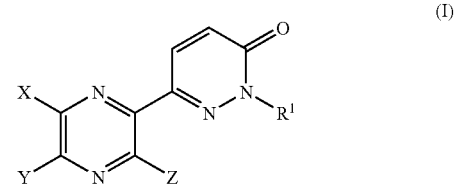

(I)

wherein $R^1$, X, Y and Z are each as defined in claim 1, or a salt thereof;
which comprises
(1) halogenation of a compound of the formula (Id):

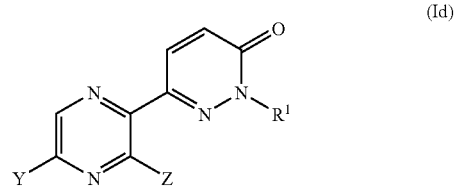

(Id)

wherein $R^1$, Y and Z are each as defined above, or a salt thereof with N-halosuccinimide to give a compound of the formula (Ie):

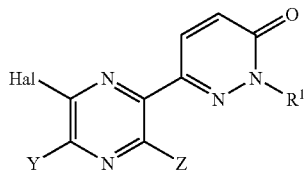

(Ie)

wherein R¹, Y, Z and Hal are each as defined above, or a salt thereof, (2) pyrazine ring-formation of a compound of the formula (V):

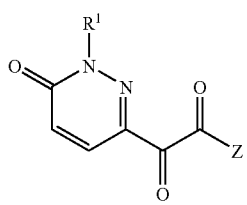

(V)

wherein R¹ and Z are each as defined above, or a salt thereof, which is prepared in two steps from a compound of the formula (XVII):

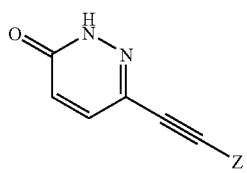

(XVII)

wherein Z is as defined above, or a salt thereof,
with 2,3-diamino-2-butenedinitrile,
to give a compound of the formula (If):

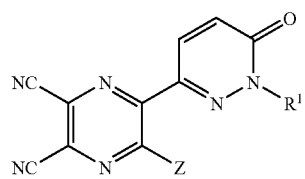

(If)

wherein R¹ and Z are each as defined above, or a salt thereof, (3) nucleophilic substitution of a compound of the formula (Ig):

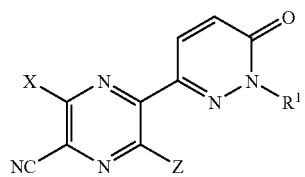

(Ig)

wherein R¹, X and Z are each as defined above, or a salt thereof,
with a compound of the formula (VI):

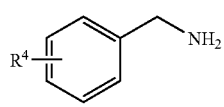

(VI)

wherein R⁴ is lower alkoxy;
or a salt thereof to give a compound of the formula (Ih):

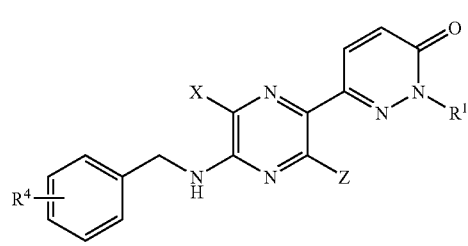

(Ih)

wherein R¹, R⁴, X and Z are each as defined above, or a salt thereof, (4) reacting a compound of the formula (VII):

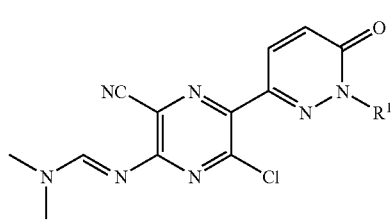

(VII)

wherein R¹ is as defined above, or a salt thereof, which is prepared in three steps from a compound of the formula (XXI):

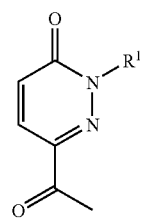

(XI)

wherein R¹ is as defined above, or a salt thereof,
with an organoboron compound of the formula (VIII):

Z—BW₂ (VIII)

wherein Z is as defined above; and
BW₂ is a constituent of boronic acid,
or a salt thereof, to give a compound of the formula (Ii):

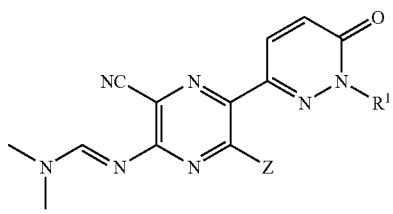

wherein R¹ and Z are each as defined above, or a salt thereof.

13. A pharmaceutical composition comprising the compound of claim 1 or a pharmaceutically acceptable salt thereof in admixture with a pharmaceutically acceptable carrier.

14. A method for treating a disease selected from the group consisting of depression, dementia, Parkinson's disease, anxiety, pain, hypertension, obesity, gout and bronchial asthma which comprises administering the compound of claim 1 or a pharmaceutically acceptable salt thereof to a human being or an animal.

15. A process for preparing a pharmaceutical composition which comprises admixing the compound of claim 1 or a pharmaceutically acceptable salt thereof with a pharmaceutically acceptable carrier.

* * * * *